(12) United States Patent
Kolczewski et al.

(10) Patent No.: US 8,163,740 B2
(45) Date of Patent: *Apr. 24, 2012

(54) 6-SUBSTITUTED BENZOXAZINES

(75) Inventors: Sabine Kolczewski, Loerrach (DE); Olivier Roche, Folgensbourg (FR); Lucinda Steward, Basel (CH); Juergen Wichmann, Steinen (DE); Thomas Woltering, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 151 days.

This patent is subject to a terminal disclaimer.

(21) Appl. No.: 12/549,745

(22) Filed: Aug. 28, 2009

(65) Prior Publication Data

US 2010/0063037 A1 Mar. 11, 2010

(30) Foreign Application Priority Data

Sep. 8, 2008 (EP) .................................... 08163833

(51) Int. Cl.
*C07D 265/02* (2006.01)
*C07D 413/04* (2006.01)
*A61K 31/536* (2006.01)

(52) U.S. Cl. ...................... 514/230.5; 544/90
(58) Field of Classification Search .................... 544/90; 514/230.5
See application file for complete search history.

(56) References Cited

FOREIGN PATENT DOCUMENTS

| WO | 03/045313 | 6/2003 |
|---|---|---|
| WO | WO 2004/096771 | 11/2004 |
| WO | 2007/022946 | 3/2007 |

OTHER PUBLICATIONS

Hoyer et al., Pharmacol. Rev. vol. 46, pp. 157-204 (1994).
Rees et al., FEBS Lett. vol. 355, pp. 242-246 (1994).
Francken et al., Eur. J. Pharmacol. vol. 361, pp. 299-309 (1998).
Noda et al., J. Neurochem. vol. 84, pp. 222-232 (2003).
Thomas, D. R., Pharmacol. Ther. vol. 111(3) pp. 707-714 (2006).
Doly et al., The Journal of Comparative Neurology vol. 476 pp. 316-329 (2004).
Dubertret et al., J. of Psychiatric Research vol. 35 pp. 371-376 (2004).

*Primary Examiner* — Kahsay T Habte
(74) *Attorney, Agent, or Firm* — George W. Johnston; Patricia S. Rocha-Tramaloni; Kimberly J. Prior

(57) ABSTRACT

The present invention is concerned with 6-substituted benzoxazine derivatives of formula (I)

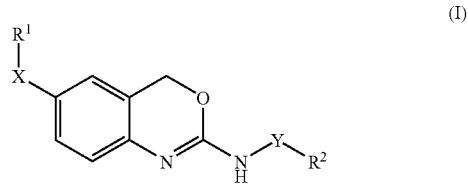

wherein X, Y, $R^1$ and $R^2$ are as described herein, their manufacture, and pharmaceutical compositions containing them. The active compounds of the present invention are $5-HT_{5A}$ receptor antagonists, useful in the prevention and/or treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, abuse of drugs, motor disorders, Parkinson's disease, psychiatric disorders or gastrointestinal disorders.

49 Claims, No Drawings

6-SUBSTITUTED BENZOXAZINES

PRIORITY OF RELATED APPLICATION(S)

This application claims the benefit of European Patent Application No. 08163833.0, filed Sep. 8, 2008, which is hereby incorporated by reference in its entirety.

BACKGROUND OF THE INVENTION

The neurotransmitter 5-hydroxytryptamine (5-HT, serotonin) modulates a wide range of physiological and pathological processes in the central nervous system and periphery, including anxiety, sleep regulation, aggression, feeding and depression (Hoyer et al., *Pharmacol. Rev.* 46, 157-204, 1994). Both pharmacological characterization and molecular cloning of several 5-HT receptor genes has revealed that 5-HT mediates its diverse physiological actions through a multiplicity of receptor subtypes. These receptors belong to at least two different protein superfamilies: ligand-gated ion channel receptor ($5-HT_3$) and the G-protein-coupled 7-transmembrane receptors (thirteen distinct receptors cloned to date). In addition, within the G-protein-coupled receptors, serotonin exerts its actions through a multiplicity of signal transduction mechanisms.

The cloning and characterization of the human $5-HT_{5A}$ serotonin receptor has been described in *FEBS Letters,* 355, 242-246 (1994). The sequence is not closely related to that of any previously known serotonin receptor, with the best homology being 35% to the human $5-HT_{1B}$ receptor. It encodes a predicted 357 amino-acid protein, with seven putative transmembrane domains, consistent with that of a G-protein coupled receptor. The sequence is characterized by containing an intron between transmembrane domains V and VI. More recently coupling to Gi/o α mechanisms has been demonstrated with the inhibition of forskolin stimulated cAMP and also evidence for more complicated G-protein mediated coupling mechanisms have been proposed (Francken et al. *Eur. J. Pharmacol.* 361, 299-309, 1998; Noda et al., *J. Neurochem.* 84, 222-232, 2003). Furthermore, in WO 2004/096771 it is described the use of compounds, which are active on the $5-HT_{5A}$ serotonin receptor for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

The *Pharmacology & Therapeutics,* 111, 707-714 (2006) describes potential therapeutic utility of $5-HT_{5A}$ receptor ligands for the treatment of circadian rhythm, sleep disturbances, mood disorders, schizophrenia, cognitive disorders and autism. The *Journal of Comparative Neurology,* 476, 316-329 (2004) suggests based on the localisation pattern of the $5-HT_{5A}$ receptor in the rat spinal cord that $5-HT_{5A}$ receptors may play a role in central motor control, nociception and autonomic function such as stress induced urinary incontinence and overactive bladder. The *Journal of Psychiatric Research,* 38, 371-376 (2004) describes evidence for a potential significant role of the $5-HT_{5A}$ gene in schizophrenia and more specifically in patients with later age at onset.

SUMMARY OR THE INVENTION

The present invention provides 6-substituted benzoxazine derivatives as $5-HT_{5A}$ receptor antagonists, methods for their manufacture, pharmaceutical compositions containing them and their use for the prevention and/or treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, abuse of drugs, motor disorders, Parkinson's disease, psychiatric disorders or gastrointestinal disorders.

In particular, the present invention provides compounds of the general formula (I)

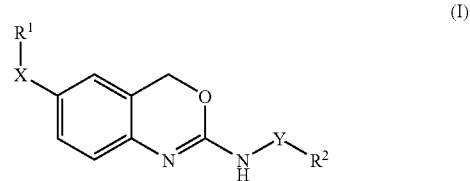

(I)

wherein
X is a bond, —NH—, —NH—S(O)$_2$—, —NH—CH$_2$—, —CH$_2$—, —NH—C(O)—, —CH$_2$—NH—C(O)—, —NH—C(O)—CH$_2$—, —NH—C(O)—CH$_2$—NH—, —NR$^a$—C(O)—NR$^b$—, or —NH—S(O)$_2$—NH—;
R$^1$ is halo;
C$_{1-7}$-alkyl, optionally substituted by OH, C$_{1-7}$ alkoxy or CN;
C$_{1-7}$-alkoxy;
NR$^a$R$^b$;
—C(NH$_2$)N(OH);
cyano;
nitro;
cycloalkyl;
heterocycloalkyl;
aryl;
heteroaryl; or
vinyl;
wherein each of said cycloalkyl, heterocycloalkyl, aryl and heteroaryl is optionally substituted by one or more halo, cyano, nitro, C$_{1-7}$-alkyl, C$_{1-7}$-haloalkyl, C$_{1-7}$-hydroxyalkyl, C$_{1-7}$-cyanoalkyl, C$_{1-7}$-alkoxy, C$_{1-7}$-alkoxy-alkyl, —NR$^a$R$^b$, or 3- to 7-membered monocyclic cycloalkyl; and
wherein said vinyl is optionally substituted by phenyl or a 5- or 6-membered monocyclic heteroaryl;
Y is a bond, —CH$_2$— or —CH$_2$—CH$_2$—O—;
R$^2$ is cycloalkyl;
heterocycloalkyl;
aryl;
heteroaryl; or
5- or 6-membered cycloalkyl or heterocycloalkyl, anellated with a benzo ring;
wherein each of said cycloalkyl, heterocycloalkyl, aryl, heteroaryl, 5- or 6-membered cycloalkyl or heterocycloalkyl anellated with a benzo ring is optionally substituted by one or more halo, hydroxyl, C$_{1-7}$-alkyl, C$_{1-7}$-alkoxy, or 3- to 7-membered monocyclic cycloalkyl; and
R$^a$ and R$^b$ are each independently hydrogen or C$_{1-7}$-alkyl;
or a pharmaceutically acceptable salt or ester thereof.

The compounds of formula (I) can contain asymmetric carbon atoms. Accordingly, the present invention includes all stereoisomeric forms of the compounds of formula (I), including each of the individual enantiomers and mixtures thereof, i.e. their individual optical isomers and mixtures thereof.

Compounds of formula (I) have good activity on the 5-HT$_{5A}$ receptor. Therefore, the invention provides compounds of formula (I) or pharmaceutically acceptable salts thereof as well as their use in the manufacture of medicaments for the treatment of depression (which term includes bipolar depression, unipolar depression, single or recurrent major depressive episodes with or without psychotic features, catatonic features, melancholic features, atypical features or postpartum onset, seasonal affective disorders and dysthymia, depressive disorders resulting from a general medical condition including, but not limited to, myocardial infarction, diabetes, miscarriage or abortion), anxiety disorders, (which includes generalized anxiety and social anxiety disorder, panic disorders, agoraphobia, social phobia, obsessive compulsive disorders, post-traumatic stress disorders), psychotic disorders (which includes schizophrenia, schizoaffective disorders, bipolar disease, mania, psychotic depression, and other psychoses involving paranoia and delusions), pain (particularly neuropathic pain), memory disorders (including dementia, amnesic disorders and age-associated memory impairment), disorders of eating behaviors (including nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, nicotine, benzodiazepines, alcohol (ethanol), caffeine, phencyclidine and phencyclidine-like compounds, opiates such as cannabis, heroin, morphine, sedative hypnotic, amphetamine or amphetamine-related drugs), motor disorders such as Parkinson's disease, dementia in Parkinson's disease, neuroleptic-induced Parkinsonism and tardive dyskinesias, as well as other psychiatric disorders and gastrointestinal disorders such as irritable bowel syndrome (WO 2004/096771).

The preferred indications with regard to the present invention are the treatment of anxiety, depression, sleep disorders and schizophrenia.

DETAILED DESCRIPTION OF THE INVENTION

Unless otherwise indicated, the following definitions are set forth to illustrate and define the meaning and scope of the various terms used to describe the invention herein. It must be noted that, as used in the specification and the appended claims, the singular forms "a", "an," and "the" include plural forms unless the context clearly dictates otherwise.

The following definitions of the general terms apply irrespective of whether the terms in question appear alone or in combination.

As used herein, the term "$C_{1-7}$-alkyl" denotes monovalent linear or branched saturated hydrocarbon moiety, consisting solely of carbon and hydrogen atoms, having from 1 to 7 carbon atoms, for example, methyl, ethyl, propyl, isopropyl, n-butyl, iso-butyl, sec-butyl, tert-butyl and the like. Preferred alkyl groups are groups with 1, 2, 3 or 4 carbon atoms. Particularly preferred are methyl, ethyl, isopropyl and 2-methyl-propyl.

The term "$C_{1-7}$-alkoxy" denotes a group —O—R' wherein R' is $C_{1-7}$-alkyl as defined above, preferably methoxy.

The term "$C_{1-7}$-alkoxy-alkyl" denotes a group —R"—O—R' wherein R' and R" are independently $C_{1-7}$-alkyl as defined above, preferably methoxy-methyl and methoxy-ethyl.

The term "halo or halogen" denotes chloro, iodo, fluoro and bromo. Preferred halo are fluoro, chloro and bromo.

The term "$C_{1-7}$-haloalkyl" denotes an alkyl group as defined above wherein at least one of the hydrogen atoms of the alkyl group is replaced by a halogen atom, preferably fluoro or chloro, most preferably fluoro. Examples of $C_{1-7}$-haloalkyl include but are not limited to methyl, ethyl, propyl, isopropyl, isobutyl, sec-butyl, tert-butyl, pentyl or n-hexyl wherein one or more hydrogen atoms are replaced by Cl, F, Br or I atom(s), as well as those $C_{1-7}$-haloalkyl groups specifically illustrated by the examples herein below. Among the preferred $C_{1-7}$-haloalkyl groups are monofluoro-, difluoro- or trifluoro-methyl, -ethyl or -propyl, particularly preferred examples are trifluoro-methyl and 2,2,2-trifluoro-ethyl.

The term "$C_{1-7}$-hydroxyalkyl" denotes an alkyl group as defined above wherein at least one of the hydrogen atoms of the alkyl group is replaced by a hydroxy group. Examples of $C_{1-7}$-hydroxyalkyl include but are not limited to methyl, ethyl, propyl, isopropyl, isobutyl, sec-butyl, tert-butyl, pentyl or n-hexyl wherein one or more hydrogen atoms are replaced by OH, as well as those $C_{1-7}$-hydroxyalkyl groups specifically illustrated by the examples herein below. Particularly preferred are hydroxy-methyl, hydroxy-ethyl and 2-hydroxy-2-methyl-propyl.

The term "$C_{1-7}$-cyanoalkyl" denotes an alkyl group as defined above wherein at least one of the hydrogen atoms of the alkyl group is replaced by a cyano group. Examples of $C_{1-7}$-cyanoalkyl include but are not limited to methyl, ethyl, propyl, isopropyl, isobutyl, sec-butyl, tert-butyl, pentyl or n-hexyl wherein one or more hydrogen atoms are replaced by cyano, as well as those $C_{1-7}$-cyanoalkyl groups specifically illustrated by the examples herein below.

The term "cycloalkyl" refers to a monovalent saturated monocyclic or bicyclic hydrocarbon radical of 3 to 8 ring carbon atoms. Bicyclic means consisting of two saturated carbocycles having two carbon atoms in common, i.e. the bridge separating the two rings is either a single bond or a chain of preferably one or two carbon atoms. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, and bicyclo[2.2.2]octanyl. Preferred cycloalkyl is a monocyclic hydrocarbon radical of 3 to 8 ring carbon atoms, and preferred examples are cyclopropyl, cyclopentyl, cyclohexyl, cycloheptyl and cyclooctyl.

The term "heterocycloalkyl" refers to a monovalent saturated 5- to 9-membered monocyclic or bicyclic ring system containing one, two or three ring heteroatoms selected from N, O and S, the remaining ring atoms being carbon atoms. In case of monocyclic heterocycloalkyl, the ring is preferably 5- or 6-membered, in case of bicyclic heterocycloalkyl, the bicyclic ring is preferably 7-, 8- or 9-membered. "Heterocycloalkyl" can be unsubstituted or substituted as described herein. Examples for substituents on heterocycloalkyl are independently selected from $C_{1-7}$-alkyl, hydroxy, $C_{1-7}$-hydroxyalkyl, benzyl, oxo, —C(O)O—$C_{1-7}$-alkyl, cycloalkyl, alkylene-O—$C_{1-7}$-alkyl, —C(O)—$C_{1-7}$-haloalkyl, —C(O)-alkylene-O—$C_{1-7}$-alkyl, $C_{1-7}$-cyanoalkyl, alkylene-S(O)$_x$—$C_{1-7}$-alkyl, -alkylene-C(O)N($C_{1-7}$-alkyl)$_2$, halo, $C_{1-7}$-haloalkyl, $C_{1-7}$-alkoxy or $C_{1-7}$-alkoxy-$C_{1-7}$-alkyl, wherein x is 0, 1, or 2. Particularly preferred examples are piperidinyl, piperazinyl, morpholinyl, thiomorpholinyl, 1,1-dioxo-1$\lambda^6$-thiomorpholinyl, 8-aza-bicyclo[3.2.1]oct-3-yl, 3-oxa-9-aza-bicyclo[3.3.1]non-7-yl and 3-oxa-7,9-diaza-bicyclo[3.3.1]non-7-yl.

The term "5- or 6-membered heterocycloalkyl" refers to a monovalent saturated monocycle as defined above. Preferably, 5- or 6-membered heterocycloalkyl is a monovalent saturated monocyclic ring containing one or two ring heteroatoms selected from N, O, and S. Examples for 5- or 6-membered heterocycloalkyl moieties are tetrahydropyranyl, tetrahydrothiopyranyl, tetrahydrofuranyl, tetrahydrothiophenyl, pyrrolidinyl, imidazolidinyl, morpholinyl, thiomorpholinyl, piperidinyl, and piperazinyl. Preferred examples are morpholinyl, thiomorpholinyl, piperidinyl or piperazinyl. The 5- or 6-membered heterocycloalkyl moiety is optionally substituted as described herein.

The term "aryl" denotes a monovalent cyclic aromatic hydrocarbon moiety consisting of a mono- or bicyclic aromatic ring, for example phenyl or naphthyl. Aryl is optionally substituted as described herein. Particularly preferred is phenyl.

The term "aromatic" means the presence of an electron sextet in a ring, according to Hückel's rule.

The term "heteroaryl" denotes an aromatic monocyclic or bicyclic ring system containing one, two, three or four heteroatoms selected from N, O, and S, the remaining ring atoms being C. Preferably, the monocyclic heteroaryl ring is 5 or 6 membered and the bicyclic heteroaryl ring is 9 or 10 membered. The one, two, three or four heteroatoms of the bicyclic heteroaryl moiety are located in either one or both rings. Examples for 5- or 6-membered monocyclic heteroaryl include but are not limited to pyridinyl, pyridazinyl, pyrimidinyl, pyrazinyl, pyrrolyl, furanyl, thiophenyl, pyrazolyl, imidazolyl, oxazolyl, isoxazolyl, thiazolyl, isothiazolyl, oxadiazolyl, or tetrazolyl. Examples for 9- or 10-membered bicyclic heteroaryl include but are not limited to indolyl, benzofuranyl, benzothiophenyl, benzimidazolyl, benzoxyzolyl, benzoisoxazolyl, benzothiazolyl, benzoisothiazolyl, benzotriazolyl, purinyl, quinolinyl, isoquinolinyl, cinnolinyl, quinazolinyl, quinoxalinyl, phtalazinyl, or pteridinyl. Preferred examples for 5- or 6-membered monocyclic heteroaryl are imidazolyl, furanyl, oxazolyl, isoxazolyl, thiazolyl, [1,2,4]-oxadiazolyl, [1,3,4]-oxadiazolyl, tetrazolyl, pyridinyl, or pyrimidinyl. A preferred example for a 9-membered bicyclic heteroaryl is benzoxazolyl. Heteroaryl is optionally substituted as described herein.

The term "5- or 6-membered cycloalkyl or heterocycloalkyl, anellated with a benzo ring" means that the attachment to the 6-substituted benzoxazine derivative is on the 5- or 6-membered cycloalkyl or heterocycloalkyl ring, such as shown in formula G:

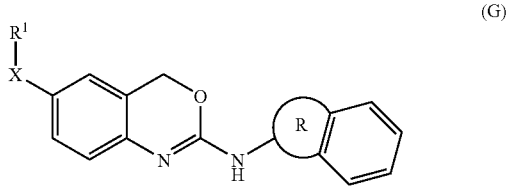

(G)

wherein R denotes the 5- or 6-membered cycloalkyl or heterocycloalkyl ring. Particularly preferred is indanyl, 1,2,3,4-tetrahydro-naphthalenyl, 2,3-dihydro-benzofuranyl and chromanyl.

The term "anellated" denotes the attachment of a further ring to an existing ring via a common single or double bond, i.e. both rings share one single or double bond. Annular residues are hence constructed from side-on condensed cyclic segments.

The term "vinyl" denotes a monovalent unsaturated hydrocarbon moiety, consisting of two carbon, bound together via double bond, and up to three hydrogen atoms. Vinyl can optionally be substituted by aryl or heteroaryl. Preferred vinyl groups are vinyl, styryl and pyridinyl-vinyl.

The term "substituted", unless specifically defined otherwise, means that the specified group or moiety can bear 1, 2, 3, 4, 5 or 6 substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents. Thereby, one, two or three substituents are preferred.

The term "pharmaceutically acceptable," such as pharmaceutically acceptable carrier, excipient, etc., means pharmacologically acceptable and substantially non-toxic to the subject to which the particular compound is administered.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) which comprise an acidic group, such as e.g. a COOH group, can further form salts with bases. Examples of such salts are alkaline, earth-alkaline and ammonium salts such as e.g. Na—, K—, Ca— and trimethylammoniumsalt. The term "pharmaceutically acceptable salts" also refers to such salts.

The term "pharmaceutically acceptable esters" embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

The term "therapeutically effective amount" means an amount that is effective to prevent, alleviate or ameliorate symptoms of disease or prolong the survival of the subject being treated.

In detail, the present invention provides compounds of formula (I)

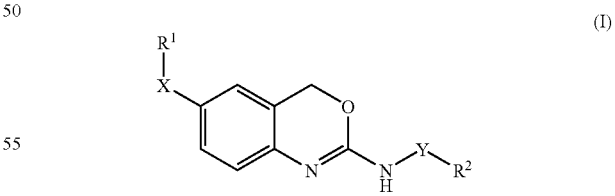

(I)

wherein
X is a bond, —NH—, —NH—S(O)$_2$—, —NH—CH$_2$—, —CH$_2$—, —NH—C(O)—, —CH$_2$—NH—C(O)—, —NH—C(O)—CH$_2$—, —NH—C(O)—CH$_2$—NH—, —NR$^a$—C(O)—NR$^b$—, or —NH—S(O)$_2$—NH—;
R$^1$ is halo;
C$_{1-7}$-alkyl, optionally substituted by OH, C$_{1-7}$ alkoxy or CN;
C$_{1-7}$-alkoxy;
NR$^a$R$^b$;

—C(NH$_2$)N(OH);
cyano;
nitro;
cycloalkyl;
heterocycloalkyl;
aryl;
heteroaryl; or
vinyl;
wherein each of said cycloalkyl, heterocycloalkyl, aryl and heteroaryl is optionally substituted by one or more halo, cyano, nitro, C$_{1-7}$-alkyl, C$_{1-7}$-haloalkyl, C$_{1-7}$-hydroxyalkyl, C$_{1-7}$-cyanoalkyl, C$_{1-7}$-alkoxy, C$_{1-7}$-alkoxy-alkyl, —NR$^a$R$^b$, or 3- to 7-membered monocyclic cycloalkyl; and
wherein said vinyl is optionally substituted by phenyl or a 5- or 6-membered monocyclic heteroaryl;
Y is a bond, —CH$_2$— or —CH$_2$—CH$_2$—O—;
R$^2$ is cycloalkyl;
heterocycloalkyl;
aryl;
heteroaryl; or
5- or 6-membered cycloalkyl or heterocycloalkyl, anellated with a benzo ring;
wherein each of said cycloalkyl, heterocycloalkyl, aryl, heteroaryl, 5- or 6-membered cycloalkyl or heterocycloalkyl anellated with a benzo ring is optionally substituted by one or more halo, hydroxyl, C$_{1-7}$-alkyl, C$_{1-7}$-alkoxy, or 3- to 7-membered monocyclic cycloalkyl; and
R$^a$ and R$^b$ are each independently hydrogen or C$_{1-7}$-alkyl;
or a pharmaceutically acceptable salt or ester thereof.

In certain embodiments of the compound of formula (I),
X is a bond, —NH—, —NH—S(O)$_2$—, —NH—CH$_2$—, —CH$_2$—, —NH—C(O)—, —CH$_2$—NH—C(O)—, —NH—C(O)—CH$_2$—, —NH—C(O)—CH$_2$NH—, —NR$^a$—C(O)—NR$^b$—, or —NH—S(O)$_2$—NH—;
R$^1$ is halo;
C$_{1-7}$-alkyl, optionally substituted by OH or CN;
C$_{1-7}$-alkoxy;
—NR$^a$R$^b$;
—C(NH$_2$)N(OH);
cyano;
nitro;
cycloalkyl;
heterocycloalkyl;
aryl;
heteroaryl; or
vinyl;
wherein each of said cycloalkyl, heterocycloalkyl, aryl and heteroaryl is optionally substituted by one or more halo, cyano, nitro, C$_{1-7}$-alkyl, C$_{1-7}$-haloalkyl, C$_{1-7}$-hydroxyalkyl, C$_{1-7}$-cyanoalkyl, C$_{1-7}$-alkoxy, —NR$^a$R$^b$, or 3- to 7-membered monocyclic cycloalkyl; and
wherein said vinyl is optionally substituted by phenyl or a 5- or 6-membered monocyclic heteroaryl;
Y is a bond, —CH$_2$— or —CH$_2$—CH$_2$—O—;
R$^2$ is cycloalkyl;
heterocycloalkyl;
aryl;
heteroaryl; or
5- or 6-membered cycloalkyl or heterocycloalkyl, anellated with a benzo ring;
wherein each of said cycloalkyl, heterocycloalkyl, aryl, heteroaryl, 5- or 6-membered cycloalkyl or heterocycloalkyl anellated with a benzo ring is optionally substituted by one or more halo, hydroxyl, C$_{1-7}$-alkyl, C$_{1-7}$-alkoxy, or 3- to 7-membered monocyclic cycloalkyl; and
R$^a$ and R$^b$ is each independently hydrogen or C$_{1-7}$-alkyl.

Preferred compounds of formula (I) are compounds of formula (Ia):

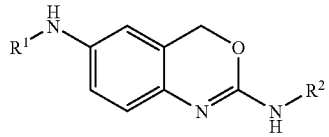

(Ia)

wherein
R$^1$ is heteroaryl, optionally substituted by one or more C$_{1-7}$-alkyl, C$_{1-7}$-haloalkyl and cyclopropyl;
R$^2$ is 5- or 6-membered cycloalkyl or heterocycloalkyl anellated with a benzo ring, optionally substituted by one or more halo and C$_{1-7}$-alkoxy;
or a pharmaceutically acceptable salt thereof.

Even more preferred are compounds of formula (Ia) wherein
R$^1$ is heteroaryl selected from the group consisting of pyridinyl, pyrimidinyl, [1,3,4]oxadiazolyl, and 2H-tetrazolyl; wherein said heteroaryl is optionally substituted by one or more C$_{1-7}$-alkyl, C$_{1-7}$-haloalkyl and cyclopropyl;
R$^2$ is

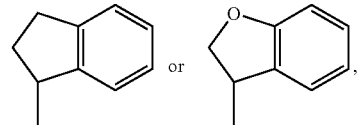

wherein said radicals are optionally substituted by one or more halo and C$_{1-7}$-alkoxy;
or a pharmaceutically acceptable salt thereof.

Special preference is given to the following compounds of formula (Ia):
N$^2$-(R)-Indan-1-yl-N$^6$-(6-trifluoromethyl-pyridin-2-yl)-4H-benzo[d][1,3]oxazine-2,6-diamine,
N$^2$-(R)-Indan-1-yl-N$^6$-(4-trifluoromethyl-pyrimidin-2-yl)-4H-benzo[d][1,3]oxazine-2,6-diamine,
N$^6$-(4,6-Dimethyl-pyrimidin-2-yl)-N$^2$-(R)-indan-1-yl-4H-benzo[d][1,3]oxazine-2,6-diamine,
rac-N$^2$-(5-Fluoro-indan-1-yl)-N$^6$-(6-trifluoromethyl-pyridin-2-yl)-4H-benzo[d][1,3]oxazine-2,6-diamine,
rac-N$^2$-(5-Fluoro-indan-1-yl)-N$^6$-(4-trifluoromethyl-pyrimidin-2-yl)-4H-benzo[d][1,3]oxazine-2,6-diamine,
rac-N$^2$-(4-Methoxy-2,3-dihydro-benzofuran-3-yl)-N$^6$-(6-trifluoromethyl-pyridin-2-yl)-4H-benzo[d][1,3]oxazine-2,6-diamine,
rac-N$^2$-(4-Methoxy-2,3-dihydro-benzofuran-3-yl)-N$^6$-(4-trifluoromethyl-pyrimidin-2-yl)-4H-benzo[d][1,3]oxazine-2,6-diamine,
rac-N$^2$-(7-Methoxy-indan-1-yl)-N$^6$-(6-trifluoromethyl-pyridin-2-yl)-4H-benzo[d][1,3]-oxazine-2,6-diamine,
rac-N$^2$-(7-Methoxy-indan-1-yl)-N$^6$-(4-trifluoromethyl-pyrimidin-2-yl)-4H-benzo[d][1,3]oxazine-2,6-diamine,
N$^2$-(7-Methoxy-indan-1-yl)-N$^6$-(5-methyl-[1,3,4]oxadiazol-2-yl)-4H-benzo[d][1,3]oxazine-2,6-diamine,
rac-N$^2$-(5-Fluoro-indan-1-yl)-N$^6$-(5-methyl-[1,3,4]oxadiazol-2-yl)-4H-benzo[d][1,3]oxazine-2,6-diamine,
rac-N$^2$-(4-Methoxy-2,3-dihydro-benzofuran-3-yl)-N$^6$-(5-methyl-[1,3,4]oxadiazol-2-yl)-4H-benzo[d][1,3]oxazine-2,6-diamine, N⁶-(5-Cyclopropyl-[1,3,4]oxadiazol-2-yl)-N²-(7-methoxy-indan-1-yl)-4H-benzo[d][1,3]oxazine-2,6-diamine,
N⁶-(2-tert-Butyl-2H-tetrazol-5-yl)-N²-(7-methoxy-indan-1-yl)-4H-benzo[d][1,3]oxazine-2,6-diamine,
N²-(R)-Indan-1-yl-N⁶-(5-methyl-[1,3,4]oxadiazol-2-yl)-4H-benzo[d][1,3]oxazine-2,6-diamine,
N²-(R)-Indan-1-yl-N⁶-(5-trifluoromethyl-[1,3,4]oxadiazol-2-yl)-4H-benzo[d][1,3]oxazine-2,6-diamine,
N²-(7-Methoxy-indan-1-yl)-N⁶-(5-trifluoromethyl-[1,3,4]oxadiazol-2-yl)-4H-benzo[d][1,3]oxazine-2,6-diamine,
N²-(4-Methoxy-2,3-dihydro-benzofuran-3-yl)-N⁶-(5-trifluoromethyl-[1,3,4]oxadiazol-2-yl)-4H-benzo[d][1,3]oxazine-2,6-diamine, and
N²-(5-Fluoro-indan-1-yl)-N⁶-(5-trifluoromethyl-[1,3,4]oxadiazol-2-yl)-4H-benzo[d][1,3]oxazine-2,6-diamine.

Preferred compounds of formula (I) are compounds of formula (Ib):

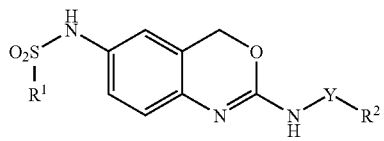
(Ib)

wherein
R¹ is C₁₋₇-alkyl;
—NRᵃRᵇ;
cycloalkyl;
heterocycloalkyl; or
aryl;
wherein each of said cycloalkyl, heterocycloalkyl and aryl is optionally substituted by one or more C₁₋₇-alkyl;
Y is a bond or —CH₂—CH₂—O—;
R² is cycloalkyl;
aryl; or
5- or 6-membered cycloalkyl or heterocycloalkyl, anellated with a benzo ring;
wherein each of said 5- or 6-membered cycloalkyl or heterocycloalkyl anellated with a benzo ring is optionally substituted by one or more halo, C₁₋₇-alkoxy and cyclopropyl; and
Rᵃ and Rᵇ is each independently hydrogen or C₁₋₇-alkyl;
or a pharmaceutically acceptable salt thereof.

Even more preferred are compounds of formula (Ib) wherein
R¹ is methyl;
—N(CH₃)₂;
cyclopropyl;
phenyl; or
heterocycloalkyl, selected from the group consisting of

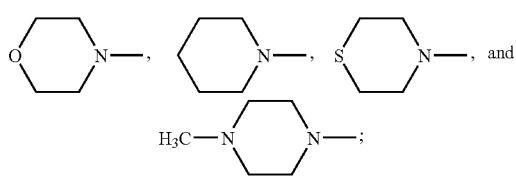

Y is a bond or —CH₂—CH₂—O—;
R² is cyclooctyl;
phenyl, optionally substituted by cyclopropyl; or
a 5- or 6-membered cycloalkyl or heterocycloalkyl, anellated with a benzo ring selected from the group consisting of

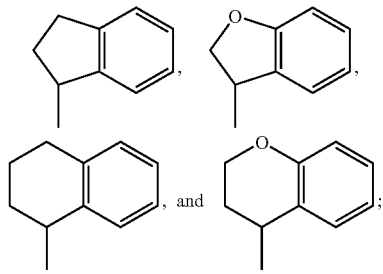

wherein each of said 5- or 6-membered cycloalkyl or heterocycloalkyl anellated with a benzo ring is optionally substituted by one or more halo, C₁₋₇-alkoxy and cyclopropyl;
or a pharmaceutically acceptable salt thereof.

Special preference is given to the following compounds of formula (Ib):
N,N-(Dimethyl)-N'-{2-((R)-indan-1-ylamino)-4H-benzo[d][1,3]oxazin-6-yl}-sulfamide,
Piperidine-1-sulfonic acid [2-((R)-indan-1-ylamino)-4H-benzo[d][1,3]oxazin-6-yl]-amide,
Morpholine-4-sulfonic acid [2-((R)-indan-1-ylamino)-4H-benzo[d][1,3]oxazin-6-yl]-amide,
rac-N,N-(Dimethyl)-N'-{2-(4-methoxy-2,3-dihydro-benzofuran-3-ylamino)-4H-benzo[d][1,3]oxazin-6-yl}-sulfamide,
Piperidine-1-sulfonic acid [2-(4-methoxy-2,3-dihydro-benzofuran-3-ylamino)-4H-benzo[d][1,3]oxazin-6-yl]-amide,
rac-N,N-(Dimethyl)-N'-{2-(7-Methoxy-indan-1-ylamino)-4H-benzo[d][1,3]oxazin-6-yl}-sulfamide,
rac-Piperidine-1-sulfonic acid [2-(7-methoxy-indan-1-ylamino)-4H-benzo[d][1,3]oxazin-6-yl]-amide,
rac-Morpholine-4-sulfonic acid [2-(7-methoxy-indan-1-ylamino)-4H-benzo[d][1,3]oxazin-6-yl]-amide,
rac-N,N-(Dimethyl)-N'-{2-(5-Fluoro-indan-1-ylamino)-4H-benzo[d][1,3]oxazin-6-yl}-sulfamide,
4-Methyl-piperazine-1-sulfonic acid {2-[(R)-(1,2,3,4-tetrahydro-naphthalen-1-yl)amino]-4H-benzo[d][1,3]oxazin-6-yl}-amide,
4-Methyl-piperazine-1-sulfonic acid [2-((R)-indan-1-ylamino)-4H-benzo[d][1,3]oxazin-6-yl]-amide,
N-[2-((R)-Indan-1-ylamino)-4H-benzo[d][1,3]oxazin-6-yl]-methanesulfonamide,
Cyclopropanesulfonic acid [2-((R)-indan-1-ylamino)-4H-benzo[d][1,3]oxazin-6-yl]-amide
N-[2-((R)-Indan-1-ylamino)-4H-benzo[d][1,3]oxazin-6-yl]-benzenesulfonamide,
rac-N,N-(Dimethyl)-N'-{2-(Chroman-4-ylamino)-4H-benzo[d][1,3]oxazin-6-yl}-sulfamide,
Cyclopropanesulfonic acid (2-cycloheptylamino-4H-benzo[d][1,3]oxazin-6-yl)-amide,
N,N-(Dimethyl)-N'-{2-cycloheptylamino-4H-benzo[d][1,3]oxazin-6-yl-}-sulfamide,
N-(2-Cycloheptylamino-4H-benzo[d][1,3]oxazin-6-yl)-benzenesulfonamide,
rac-N-[2-(7-Methoxy-indan-1-ylamino)-4H-benzo[d][1,3]oxazin-6-yl]-methanesulfonamide,
rac-Cyclopropanesulfonic acid [2-(7-methoxy-indan-1-ylamino)-4H-benzo[d][1,3]oxazin-6-yl]-amide,
rac-N-[2-(7-Methoxy-indan-1-ylamino)-4H-benzo[d][1,3]oxazin-6-yl]-benzenesulfonamide,
Cyclopropanesulfonic acid [2-(2-phenoxy-ethylamino)-4H-benzo[d][1,3]oxazin-6-yl]-amide, N-[2-(2-Phenoxy-ethylamino)-4H-benzo[d][1,3]oxazin-6-yl]-benzenesulfonamide,
N,N-(Dimethyl)-N'-{2-(2-Phenoxy-ethylamino)-4H-benzo[d][1,3]oxazin-6-yl}-sulfamide,
Cyclopropanesulfonic acid [2-(4-methoxy-2,3-dihydro-benzofuran-3-ylamino)-4H-benzo[d][1,3]oxazin-6-yl]-amide,
N-[2-(4-Methoxy-2,3-dihydro-benzofuran-3-ylamino)-4H-benzo[d][1,3]oxazin-6-yl]-methanesulfonamide,
N-[2-(4-Methoxy-2,3-dihydro-benzofuran-3-ylamino)-4H-benzo[d][1,3]oxazin-6-yl]-benzenesulfonamide,
Cyclopropanesulfonic acid [2-(3-cyclopropyl-phenylamino)-4H-benzo[d][1,3]oxazin-6-yl]-amide, and
N-[2-(3-Cyclopropyl-phenylamino)-4H-benzo[d][1,3]oxazin-6-yl]-benzenesulfonamide.

Preferred compounds of formula (I) are compounds of formula (Ic):

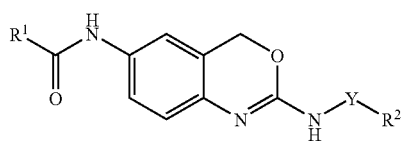

(Ic)

wherein
R$^1$ is C$_{1-7}$-alkyl or cycloalkyl;
Y is a bond, —CH$_2$— or —CH$_2$—CH$_2$—O—;
R$^2$ is cycloalkyl;
aryl;
heteroaryl; or
5- or 6-membered cycloalkyl or heterocycloalkyl, anellated with a benzo ring;
wherein each of said cycloalkyl, aryl, heteroaryl, 5- or 6-membered cycloalkyl or heterocycloalkyl anellated with a benzo ring is optionally substituted by one or more halo, C$_{1-7}$-alkoxy and cyclopropyl;
or a pharmaceutically acceptable salt thereof.

Even more preferred are compounds of formula (Ic) wherein
R$^1$ is methyl or cyclopropyl;
Y is a bond, —CH$_2$— or —CH$_2$—CH$_2$—O—;
R$^2$ is cyclooctyl;
phenyl, optionally substituted by one or more C$_{1-7}$-alkoxy and cyclopropyl;
furanyl; or
a 5- or 6-membered cycloalkyl or heterocycloalkyl, anellated with a benzo ring selected from the group consisting of

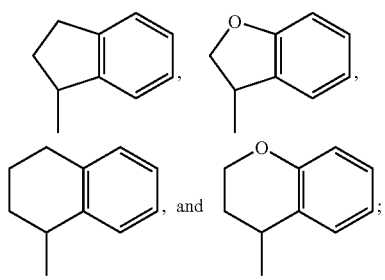

wherein each of said 5- or 6-membered cycloalkyl or heterocycloalkyl anellated with a benzo ring is optionally substituted by one or more halo and cyclopropyl;
or a pharmaceutically acceptable salt thereof.

Special preference is given to the following compounds of formula (Ic):
Cyclopropanecarboxylic acid [2-(2-methoxy-benzylamino)-4H-benzo[d][1,3]oxazin-6-yl]-amide,
Cyclopropanecarboxylic acid [2-((R)-indan-1-ylamino)-4H-benzo[d][1,3]oxazin-6-yl]-amide,
rac-Cyclopropanecarboxylic acid [2-(5-fluoro-indan-1-ylamino)-4H-benzo[d][1,3]oxazin-6-yl]-amide,
rac-Cyclopropanecarboxylic acid [2-(8-methoxy-1,2,3,4-tetrahydro-naphthalen-1-ylamino)-4H-benzo[d][1,3]oxazin-6-yl]-amide,
Cyclopropanecarboxylic acid [2-(7-methoxy-indan-1-ylamino)-4H-benzo[d][1,3]oxazin-6-yl]-amide,
N-[2-((R)-Indan-1-ylamino)-4H-benzo[d][1,3]oxazin-6-yl]-acetamide,
N-[2-(4-Methoxy-2,3-dihydro-benzofuran-3-ylamino)-4H-benzo[d][1,3]oxazin-6-yl]-acetamide,
N-[2-(7-Methoxy-indan-1-ylamino)-4H-benzo[d][1,3]oxazin-6-yl]-acetamide,
Cyclopropanecarboxylic acid {2-[(5-methyl-furan-2-ylmethyl)-amino]-4H-benzo[d][1,3]oxazin-6-yl}-amide,
rac-Cyclopropanecarboxylic acid [2-(chroman-4-ylamino)-4H-benzo[d][1,3]oxazin-6-yl]-amide,
Cyclopropanecarboxylic acid (2-cycloheptylamino-4H-benzo[d][1,3]oxazin-6-yl)-amide,
Cyclopropanecarboxylic acid [2-(2-phenoxy-ethylamino)-4H-benzo[d][1,3]oxazin-6-yl]-amide,
Cyclopropanecarboxylic acid [2-(3-cyclopropyl-phenylamino)-4H-benzo[d][1,3]oxazin-6-yl]-amide, and
Cyclopropanecarboxylic acid (2-cyclooctylamino-4H-benzo[d][1,3]oxazin-6-yl)-amide.

Preferred compounds of formula (I) are compounds of formula (Id):

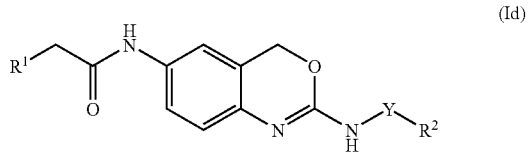

(Id)

wherein
R$^1$ is halo;
C$_{1-7}$-alkoxy;
heterocycloalkyl; or
heteroaryl;
wherein each of said heterocycloalkyl and heteroaryl is optionally substituted by one or more C$_{1-7}$-alkyl, C$_{1-7}$-alkoxy, C$_{1-7}$-haloalkyl and C$_{1-7}$-hydroxyalkyl;
Y is a bond, —CH$_2$— or —CH$_2$—CH$_2$—O—;
R$^2$ is cycloalkyl;
aryl;
heteroaryl; or
5- or 6-membered cycloalkyl or heterocycloalkyl, anellated with a benzo ring;
wherein each of said cycloalkyl, aryl, heteroaryl, 5- or 6-membered cycloalkyl or heterocycloalkyl anellated with a benzo ring is optionally substituted by one or more halo, C$_{1-7}$-alkyl, C$_{1-7}$-alkoxy and cyclopropyl;
or a pharmaceutically acceptable salt thereof.

Even more preferred are compounds of formula (Id) wherein
R$^1$ is halo;
methoxy;
imidazolyl; or heterocycloalkyl, selected from the group consisting of 9-methyl-3-oxa-7,9-diaza-bicyclo[3.3.1]non-7-yl, 9-methyl-3-oxa-9-aza-bicyclo[3.3.1]non-7-yl,

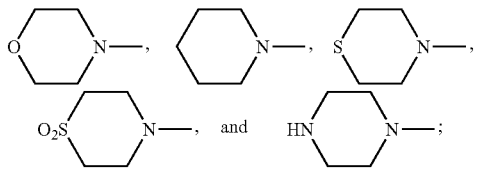

wherein each of said heterocycloalkyl is optionally substituted by one or more $C_{1-7}$-alkyl, $C_{1-7}$-alkoxy, $C_{1-7}$-haloalkyl and $C_{1-7}$-hydroxyalkyl;

Y is a bond, —CH$_2$— or —CH$_2$—CH$_2$—O—;

$R^2$ is cyclooctyl;

phenyl, optionally substituted by one or more $C_{1-7}$-alkoxy and cyclopropyl;

furanyl, optionally substituted by methyl; or a 5- or 6-membered cycloalkyl or heterocycloalkyl, anellated with a benzo ring, selected from the group consisting of

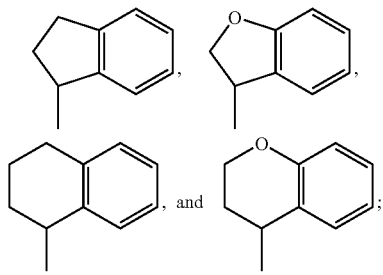

wherein each of said 5- or 6-membered cycloalkyl or heterocycloalkyl anellated with a benzo ring is optionally substituted by one or more halo and $C_{1-7}$-alkoxy;

or a pharmaceutically acceptable salt thereof.

Special preference is given to the following compounds of formula (Id):

N-[2-((R)-Indan-1-ylamino)-4H-benzo[d][1,3]oxazin-6-yl]-2-(4-methyl-piperazin-1-yl)-acetamide, rac-2-Chloro-N-[2-(4-methoxy-2,3-dihydro-benzofuran-3-ylamino)-4H-benzo[d][1,3]oxazin-6-yl]-acetamide, rac-N-[2-(4-Methoxy-2,3-dihydro-benzofuran-3-ylamino)-4H-benzo[d][1,3]oxazin-6-yl]-2-(4-methyl-piperazin-1-yl)-acetamide, rac-2-(4-Isopropyl-piperazin-1-yl)-N-[2-(4-methoxy-2,3-dihydro-benzofuran-3-ylamino)-4H-benzo[d][1,3]oxazin-6-yl]-acetamide, rac-N-[2-(4-Methoxy-2,3-dihydro-benzofuran-3-ylamino)-4H-benzo[d][1,3]oxazin-6-yl]-2-morpholin-4-yl-acetamide, rac-2-Methoxy-N-[2-(4-methoxy-2,3-dihydro-benzofuran-3-ylamino)-4H-benzo[d][1,3]oxazin-6-yl]-acetamide, N-[2-((R)-Indan-1-ylamino)-4H-benzo[d][1,3]oxazin-6-yl]-2-methoxy-acetamide, rac-N-[2-(5-Fluoro-indan-1-ylamino)-4H-benzo[d][1,3]oxazin-6-yl]-2-methoxy-acetamide, rac-2-Methoxy-N-[2-(7-methoxy-indan-1-ylamino)-4H-benzo[d][1,3]oxazin-6-yl]-acetamide, N-[2-(2-Methoxy-benzylamino)-4H-benzo[d][1,3]oxazin-6-yl]-2-(4-methyl-piperazin-1-yl)-acetamide, 2-[4-(2-Hydroxy-ethyl)-piperazin-1-yl]-N-[2-(2-methoxy-benzylamino)-4H-benzo[d][1,3]oxazine-6-yl]-acetamide, 2-(4-Isopropyl-piperazin-1-yl)-N-[2-(2-methoxy-benzylamino)-4H-benzo[d][1,3]oxazin-6-yl]-acetamide, N-[2-((R)-Indan-1-ylamino)-4H-benzo[d][1,3]oxazin-6-yl]-2-morpholin-4-yl-acetamide, 2-(4-Methyl-piperazin-1-yl)-N-{2-[(R)-(1,2,3,4-tetrahydro-naphthalen-1-yl)amino]-4H-benzo[d][1,3]oxazin-6-yl}-acetamide, 2-Morpholin-4-yl-N-{2-[(R)-(1,2,3,4-tetrahydro-naphthalen-1-yl)amino]-4H-benzo[d][1,3]oxazin-6-yl}-acetamide, rac-N-[2-(6-Fluoro-2,3-dihydro-benzofuran-3-ylamino)-4H-benzo[d][1,3]oxazin-6-yl]-2-(4-methyl-piperazin-1-yl)-acetamide, rac-N-[2-(6-Fluoro-2,3-dihydro-benzofuran-3-ylamino)-4H-benzo[d][1,3]oxazin-6-yl]-2-morpholin-4-yl-acetamide, rac-N-[2-(7-Methoxy-indan-1-ylamino)-4H-benzo[d][1,3]oxazin-6-yl]-2-morpholin-4-yl-acetamide, rac-N-[2-(5-Fluoro-indan-1-ylamino)-4H-benzo[d][1,3]oxazin-6-yl]-2-morpholin-4-yl-acetamide, N-[2-((R)-Indan-1-ylamino)-4H-benzo[d][1,3]oxazin-6-yl]-2-thiomorpholin-4-yl-acetamide, 2-(1,1-Dioxo-1$\lambda^6$-thiomorpholin-4-yl)-N-[2-((R)-indan-1-ylamino)-4H-benzo[d][1,3]oxazin-6-yl]-acetamide, 2-Imidazol-1-yl-N-[2-((R)-indan-1-ylamino)-4H-benzo[d][1,3]oxazin-6-yl]-acetamide, N-[2-((R)-Indan-1-ylamino)-4H-benzo[d][1,3]oxazin-6-yl]-2-[4-(2,2,2-trifluoro-ethyl)-piperazin-1-yl]-acetamide, N-{2-[(5-Methyl-furan-2-ylmethyl)-amino]-4H-benzo[d][1,3]oxazin-6-yl}-2-(4-methyl-piperazin-1-yl)-acetamide, N-{2-[(5-Methyl-furan-2-ylmethyl)-amino]-4H-benzo[d][1,3]oxazin-6-yl}-2-morpholin-4-yl-acetamide, rac-N-[2-(7-Methoxy-indan-1-ylamino)-4H-benzo[d][1,3]oxazin-6-yl]-2-(4-methyl-piperazin-1-yl)-acetamide, N-(2-Cycloheptylamino-4H-benzo[d][1,3]oxazin-6-yl)-2-(4-methyl-piperazin-1-yl)-acetamide, 2-(3-Hydroxymethyl-4-methyl-piperazin-1-yl)-N-[2-(7-methoxy-indan-1-ylamino)-4H-benzo[d][1,3]oxazin-6-yl]-acetamide, rac-N-[2-(Chroman-4-ylamino)-4H-benzo[d][1,3]oxazin-6-yl]-2-(4-methyl-piperazin-1-yl)-acetamide, rac-N-[2-(Chroman-4-ylamino)-4H-benzo[d][1,3]oxazin-6-yl]-2-morpholin-4-yl-acetamide, 2-(4-Methyl-piperazin-1-yl)-N-[2-(2-phenoxy-ethylamino)-4H-benzo[d][1,3]oxazin-6-yl]-acetamide, 2-Morpholin-4-yl-N-[2-(2-phenoxy-ethylamino)-4H-benzo[d][1,3]oxazin-6-yl]-acetamide, N-[2-(3-Cyclopropyl-phenylamino)-4H-benzo[d][1,3]oxazin-6-yl]-2-(4-methyl-piperazin-1-yl)-acetamide, N-[2-(7-Methoxy-indan-1-ylamino)-4H-benzo[d][1,3]oxazin-6-yl]-2-(3-methoxymethyl-4-methyl-piperazin-1-yl)-acetamide, N-[2-((R)-Indan-1-ylamino)-4H-benzo[d][1,3]oxazin-6-yl]-2-(3-methoxymethyl-4-methyl-piperazin-1-yl)-acetamide, N-(2-Cyclooctylamino-4H-benzo[d][1,3]oxazin-6-yl)-2-(4-methyl-piperazin-1-yl)-acetamide, endo-N-[2-((R)-Indan-1-ylamino)-4H-benzo[d][1,3]oxazin-6-yl]-2-(9-methyl-3-oxa-9-aza-bicyclo[3.3.1]non-7-yl)-acetamide, 2-((3SR,5SR)-3,5-Bis-(methoxymethyl)-4-methyl-piperazin-1-yl)-N-[2-((R)-indan-1-ylamino)-4H-benzo[d][1,3]oxazin-6-yl]-acetamide, and N-[2-((R)-Indan-1-ylamino)-4H-benzo[d][1,3]oxazin-6-yl]-2-(9-methyl-3-oxa-7,9-diaza-bicyclo[3.3.1]non-7-yl)-acetamide.

In certain embodiments of the compound of formula (I), X is a bond, —CH$_2$—, —CH$_2$—NH—C(O)—, —NH—, —NH—C(O)—, —NH—C(O)—CH$_2$—, —NH—C(O)—CH$_2$—NH—, —NH—CH$_2$—, —NH—S(O)$_2$— or —NR$^a$—C(O)—NR$^b$—, wherein R$^a$ and R$^b$ are either H or C$_{1-7}$ alkyl. Even more preferred compounds of the present invention are those, wherein X is a bond, —NH—, —NH—C(O)—, —NH—C(O)—CH$_2$—, —NH—CH$_2$—, —NH—S(O)$_2$— or —NR$^a$—C(O)—NR$^b$—, wherein R$^a$ and R$^b$ are either H or methyl.

In certain embodiments of the compound of formula (I), R$^1$ is:
halo;
C$_{1-7}$-alkyl, optionally substituted by OH or C$_{1-7}$ alkoxy;
C$_{1-7}$-alkoxy;
—NR$^a$R$^b$, wherein R$^a$ and R$^b$ are either H or C$_{1-7}$ alkyl;
—C(NH$_2$)N(OH);
cyano;
nitro;
cycloalkyl;
heterocycloalkyl, optionally substituted by one or more C$_{1-7}$-alkyl, C$_{1-7}$-haloalkyl, C$_{1-7}$-hydroxyalkyl, C$_{1-7}$-alkoxyalkyl, 5- to 9-membered monocyclic or bicyclic heterocycloalkyl;
aryl, optionally substituted by one or more halo;
heteroaryl, optionally substituted by one or more C$_{1-7}$-alkyl, C$_{1-7}$-haloalkyl, 3- to 7-membered monocyclic cycloalkyl; or
vinyl; optionally substituted by phenyl or a 5- or 6-membered monocyclic heteroaryl.

Even more preferred compounds of the present invention are those, wherein R$^1$ is:
halo;
C$_{1-7}$-alkyl;
—NR$^a$R$^b$, wherein R$^a$ and R$^b$ are either H or C$_{1-7}$ alkyl;
cycloalkyl;
heterocycloalkyl, optionally substituted by one or more C$_{1-7}$-alkyl; or
heteroaryl, optionally substituted by one or more C$_{1-7}$-alkyl, 3- to 7-membered monocyclic cycloalkyl.

Most preferred are compounds wherein R$^1$ is isopropyl, NH$_2$, cyclopropyl, piperazinyl substituted by methyl, [1,3,4]oxadiazolyl substituted by methyl or cyclopropyl, pyridinyl or thiazolyl.

In certain embodiments of the compound of formula (I), Y is a bond, CH$_2$— or —CH$_2$—CH$_2$—O—. Even more preferred compounds of the present invention are those, wherein Y is a bond.

In certain embodiments of the compound of formula (I), R$^2$ is:
cycloalkyl;
aryl, optionally substituted by one or more C$_{1-7}$-alkoxy or 3- to 7-membered monocyclic cycloalkyl;
heteroaryl, optionally substituted by one or more C$_{1-7}$-alkyl; or
5- or 6-membered cycloalkyl or heterocycloalkyl, anellated with a benzo ring, optionally substituted by one or more halo, C$_{1-7}$-alkyl or C$_{1-7}$-alkoxy.

Even more preferred compounds of the present invention are those, wherein R$^2$ is:
cycloalkyl; or
5- or 6-membered cycloalkyl, anellated with a benzo ring, optionally substituted by one or more halo or C$_{1-7}$-alkoxy.

Most preferred are compounds wherein R$^2$ is cycloheptyl, cyclooctyl, 1,2,3,4-tetrahydro-naphthalenyl substituted by one methoxy, indanyl optionally substituted by one fluoro or one methoxy.

Preferred compounds of present invention are those wherein R$^2$ is

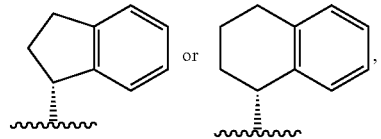

each optionally substituted by one or more halo or C$_{1-7}$-alkoxy, and wherein R$^2$ is present as (R)-stereoisomer.

In particular, preferred compounds are the compounds of formula (I) described in the examples as individual compounds as well as pharmaceutically acceptable salts as well as pharmaceutically acceptable esters thereof. Furthermore, the substituents as found in the specific examples described below, individually constitute separate preferred embodiments of the present invention.

Preferred compounds of formula (I) include but are not limited to:
(2-Methoxy-benzyl)-(6-nitro-4H-benzo[d][1,3]oxazin-2-yl)-amine,
(R)-N$^2$-Indan-1-yl-4H-benzo[d][1,3]oxazine-2,6-diamine,
N-[2-((R)-Indan-1-ylamino)-4H-benzo[d][1,3]oxazin-6-yl]-2-(4-methyl-piperazin-1-yl)-acetamide,
N$^2$-(2-Methoxy-benzyl)-4H-benzo[d][1,3]oxazine-2,6-diamine,
rac-(4-Methoxy-2,3-dihydro-benzofuran-3-yl)-(6-nitro-4H-benzo[d][1,3]oxazin-2-yl)-amine,
rac-N$^2$-(4-Methoxy-2,3-dihydro-benzofuran-3-yl)-4H-benzo[d][1,3]oxazine-2,6-diamine,
Cyclopropanecarboxylic acid [2-(2-methoxy-benzylamino)-4H-benzo[d][1,3]oxazin-6-yl]-amide,
rac-2-Chloro-N-[2-(4-methoxy-2,3-dihydro-benzofuran-3-ylamino)-4H-benzo[d][1,3]oxazin-6-yl]-acetamide,
rac-N-[2-(4-Methoxy-2,3-dihydro-benzofuran-3-ylamino)-4H-benzo[d][1,3]oxazin-6-yl]-2-(4-methyl-piperazin-1-yl)-acetamide,
rac-N$^2$-(7-Methoxy-indan-1-yl)-4H-benzo[d][1,3]oxazine-2,6-diamine,
rac-N$^2$-(5-Fluoro-indan-1-yl)-4H-benzo[d][1,3]oxazine-2,6-diamine,
rac-2-(4-Isopropyl-piperazin-1-yl)-N-[2-(4-methoxy-2,3-dihydro-benzofuran-3-ylamino)-4H-benzo[d][1,3]oxazin-6-yl]-acetamide,
rac-N-[2-(4-Methoxy-2,3-dihydro-benzofuran-3-ylamino)-4H-benzo[d][1,3]oxazin-6-yl]-2-morpholin-4-yl-acetamide,
rac-1-(1-Isopropyl-piperidin-4-yl)-3-[2-(4-methoxy-2,3-dihydro-benzofuran-3-ylamino)-4H-benzo[d][1,3]oxazin-6-yl]-urea,
rac-1-(1-Isopropyl-piperidin-4-yl)-3-[2-(4-methoxy-2,3-dihydro-benzofuran-3-ylamino)-4H-benzo[d][1,3]oxazin-6-yl]-1-methyl-urea,
rac-1-Isopropyl-3-[2-(4-methoxy-2,3-dihydro-benzofuran-3-ylamino)-4H-benzo[d][1,3]oxazine-6-yl]-urea,
rac-2-Methoxy-N-[2-(4-methoxy-2,3-dihydro-benzofuran-3-ylamino)-4H-benzo[d][1,3]oxazin-6-yl]-acetamide,
Cyclopropanecarboxylic acid [2-((R)-indan-1-ylamino)-4H-benzo[d][1,3]oxazin-6-yl]-amide, N-[2-((R)-Indan-1-ylamino)-4H-benzo[d][1,3]oxazin-6-yl]-2-methoxy-acetamide,
rac-Cyclopropanecarboxylic acid [2-(5-fluoro-indan-1-ylamino)-4H-benzo[d][1,3]oxazin-6-yl]-amide,
rac-N-[2-(5-Fluoro-indan-1-ylamino)-4H-benzo[d][1,3]oxazin-6-yl]-2-methoxy-acetamide,
rac-$N^2$-(8-Methoxy-1,2,3,4-tetrahydro-naphthalen-1-yl)-4H-benzo[d][1,3]oxazine-2,6-diamine,
rac-Cyclopropanecarboxylic acid [2-(8-methoxy-1,2,3,4-tetrahydro-naphthalen-1-ylamino)-4H-benzo[d][1,3]oxazin-6-yl]-amide,
rac-2-Methoxy-N-[2-(7-methoxy-indan-1-ylamino)-4H-benzo[d][1,3]oxazin-6-yl]-acetamide,
Cyclopropanecarboxylic acid [2-(7-methoxy-indan-1-ylamino)-4H-benzo[d][1,3]oxazin-6-yl]-amide,
N-[2-(2-Methoxy-benzylamino)-4H-benzo[d][1,3]oxazin-6-yl]-2-(4-methyl-piperazin-1-yl)-acetamide,
N,N-(Dimethyl)-N'-{2-((R)-indan-1-ylamino)-4H-benzo[d][1,3]oxazin-6-yl}-sulfamide,
2-[4-(2-Hydroxy-ethyl)-piperazin-1-yl]-N-[2-(2-methoxy-benzylamino)-4H-benzo[d][1,3]oxazin-6-yl]-acetamide,
2-(4-Isopropyl-piperazin-1-yl)-N-[2-(2-methoxy-benzylamino)-4H-benzo[d][1,3]oxazin-6-yl]-acetamide,
Piperidine-1-sulfonic acid [2-((R)-indan-1-ylamino)-4H-benzo[d][1,3]oxazin-6-yl]-amide,
Morpholine-4-sulfonic acid [2-((R)-indan-1-ylamino)-4H-benzo[d][1,3]oxazin-6-yl]-amide,
(6-Bromo-4H-benzo[d][1,3]oxazin-2-yl)-(R)-indan-1-yl-amine,
(R)-$N^2$-(1,2,3,4-Tetrahydro-naphthalen-1-yl)-4H-benzo[d][1,3]oxazine-2,6-diamine,
rac-$N^2$-(6-Fluoro-2,3-dihydro-benzofuran-3-yl)-4H-benzo[d][1,3]oxazine-2,6-diamine,
$N^2$-(R)-Indan-1-yl-$N^6$-(6-trifluoromethyl-pyridin-2-yl)-4H-benzo[d][1,3]oxazine-2,6-diamine,
N-[2-((R)-Indan-1-ylamino)-4H-benzo[d][1,3]oxazin-6-yl]-2-morpholin-4-yl-acetamide,
2-(4-Methyl-piperazin-1-yl)-N-{2-[(R)-(1,2,3,4-tetrahydro-naphthalen-1-yl)amino]-4H-benzo[d][1,3]oxazin-6-yl}-acetamide,
2-Morpholin-4-yl-N-{2-[(R)-(1,2,3,4-tetrahydro-naphthalen-1-yl)amino]-4H-benzo[d][1,3]oxazin-6-yl}-acetamide,
2-(2-Methoxy-ethylamino)-N-{2-[(R)-(1,2,3,4-tetrahydro-naphthalen-1-yl)amino]-4H-benzo[d][1,3]oxazin-6-yl}-acetamide,
2-(2-Hydroxy-2-methyl-propylamino)-N-{2-[(R)-(1,2,3,4-tetrahydro-naphthalen-1-yl)amino]-4H-benzo[d][1,3]oxazin-6-yl}-acetamide,
rac-N-[2-(6-Fluoro-2,3-dihydro-benzofuran-3-ylamino)-4H-benzo[d][1,3]oxazin-6-yl]-2-(2-methoxy-ethylamino)-acetamide,
rac-N-[2-(6-Fluoro-2,3-dihydro-benzofuran-3-ylamino)-4H-benzo[d][1,3]oxazin-6-yl]-2-(2-hydroxy-2-methyl-propylamino)-acetamide,
rac-N-[2-(6-Fluoro-2,3-dihydro-benzofuran-3-ylamino)-4H-benzo[d][1,3]oxazin-6-yl]-2-(4-methyl-piperazin-1-yl)-acetamide,
rac-N-[2-(6-Fluoro-2,3-dihydro-benzofuran-3-ylamino)-4H-benzo[d][1,3]oxazin-6-yl]-2-morpholin-4-yl-acetamide,
$N^2$-(R)-Indan-1-yl-$N^6$-(4-trifluoromethyl-pyrimidin-2-yl)-4H-benzo[d][1,3]oxazine-2,6-diamine,
$N^6$-(4,6-Dimethyl-pyrimidin-2-yl)-$N^2$-(R)-indan-1-yl-4H-benzo[d][1,3]oxazine-2,6-diamine,
N-[2-((R)-Indan-1-ylamino)-4H-benzo[d][1,3]oxazin-6-yl]-acetamide,
rac-N,N-(Dimethyl)-N'-{2-(4-methoxy-2,3-dihydro-benzofuran-3-ylamino)-4H-benzo[d][1,3]oxazin-6-yl}-sulfamide,
Piperidine-1-sulfonic acid [2-(4-methoxy-2,3-dihydro-benzofuran-3-ylamino)-4H-benzo[d][1,3]oxazin-6-yl]-amide,
N-[2-(4-Methoxy-2,3-dihydro-benzofuran-3-ylamino)-4H-benzo[d][1,3]oxazin-6-yl]-acetamide,
N-[2-(7-Methoxy-indan-1-ylamino)-4H-benzo[d][1,3]oxazin-6-yl]-acetamide,
rac-(6-Bromo-4H-benzo[d][1,3]oxazin-2-yl)-(5-fluoro-indan-1-yl)-amine,
rac-(6-Bromo-4H-benzo[d][1,3]oxazin-2-yl)-(4-methoxy-2,3-dihydro-benzofuran-3-yl)-amine,
rac-N-[2-(7-Methoxy-indan-1-ylamino)-4H-benzo[d][1,3]oxazin-6-yl]-2-morpholin-4-yl-acetamide,
rac-N-[2-(5-Fluoro-indan-1-ylamino)-4H-benzo[d][1,3]oxazin-6-yl]-2-morpholin-4-yl-acetamide,
rac-$N^2$-(5-Fluoro-indan-1-yl)-$N^6$-(6-trifluoromethyl-pyridin-2-yl)-4H-benzo[d][1,3]oxazine-2,6-diamine,
rac-$N^2$-(5-Fluoro-indan-1-yl)-$N^6$-(4-trifluoromethyl-pyrimidin-2-yl)-4H-benzo[d][1,3]oxazine-2,6-diamine,
rac-$N^2$-(4-Methoxy-2,3-dihydro-benzofuran-3-yl)-$N^6$-(6-trifluoromethyl-pyridin-2-yl)-4H-benzo[d][1,3]oxazine-2,6-diamine,
rac-$N^2$-(4-Methoxy-2,3-dihydro-benzofuran-3-yl)-$N^6$-(4-trifluoromethyl-pyrimidin-2-yl)-4H-benzo[d][1,3]oxazine-2,6-diamine,
rac-N,N-(Dimethyl)-N'-{2-(7-Methoxy-indan-1-ylamino)-4H-benzo[d][1,3]oxazin-6-yl}-sulfamide,
rac-Piperidine-1-sulfonic acid [2-(7-methoxy-indan-1-ylamino)-4H-benzo[d][1,3]oxazin-6-yl]-amide,
rac-Morpholine-4-sulfonic acid [2-(7-methoxy-indan-1-ylamino)-4H-benzo[d][1,3]oxazin-6-yl]-amide,
rac-N,N-(Dimethyl)-N'-{2-(5-Fluoro-indan-1-ylamino)-4H-benzo[d][1,3]oxazin-6-yl}-sulfamide,
N-[2-((R)-Indan-1-ylamino)-4H-benzo[d][1,3]oxazin-6-yl]-2-thiomorpholin-4-yl-acetamide,
2-(1,1-Dioxo-1$\lambda^6$-thiomorpholin-4-yl)-N-[2-((R)-indan-1-ylamino)-4H-benzo[d][1,3]oxazin-6-yl]-acetamide,
2-Imidazol-1-yl-N-[2-((R)-indan-1-ylamino)-4H-benzo[d][1,3]oxazin-6-yl]-acetamide,
2-(2-Hydroxy-2-methyl-propylamino)-N-[2-((R)-indan-1-ylamino)-4H-benzo[d][1,3]oxazin-6-yl]-acetamide,
N-[2-((R)-Indan-1-ylamino)-4H-benzo[d][1,3]oxazin-6-yl]-2-(2-methoxy-ethylamino)-acetamide,
N-[2-((R)-Indan-1-ylamino)-4H-benzo[d][1,3]oxazin-6-yl]-2-[4-(2,2,2-trifluoro-ethyl)-piperazin-1-yl]-acetamide,
4-Methyl-piperazine-1-sulfonic acid {2-[(R)-(1,2,3,4-tetrahydro-naphthalen-1-yl)amino]-4H-benzo[d][1,3]oxazin-6-yl}-amide,
4-Methyl-piperazine-1-sulfonic acid [2-((R)-indan-1-ylamino)-4H-benzo[d][1,3]oxazin-6-yl]-amide,
2-((exo)-8-Isopropyl-8-aza-bicyclo[3.2.1]oct-3-ylamino)-N-{2-[(R)-(1,2,3,4-tetrahydro-naphthalen-1-yl)amino]-4H-benzo[d][1,3]oxazin-6-yl}-acetamide,
rac-(6-Bromo-4H-benzo[d][1,3]oxazin-2-yl)-(7-methoxy-indan-1-yl)-amine,
rac-$N^2$-Chroman-4-yl-4H-benzo[d][1,3]oxazine-2,6-diamine,
N-[2-((R)-Indan-1-ylamino)-4H-benzo[d][1,3]oxazin-6-yl]-2-((exo)-8-isopropyl-8-aza-bicyclo[3.2.1]oct-3-ylamino)-acetamide,
$N^2$-(5-Methyl-furan-2-ylmethyl)-4H-benzo[d][1,3]oxazine-2,6-diamine,
N-[2-((R)-Indan-1-ylamino)-4H-benzo[d][1,3]oxazin-6-yl]-methanesulfonamide, Cyclopropanesulfonic acid [2-((R)-indan-1-ylamino)-4H-benzo[d][1,3]oxazin-6-yl]-amide,
rac-$N^2$-(7-Methoxy-indan-1-yl)-$N^6$-(6-trifluoromethyl-pyridin-2-yl)-4H-benzo[d][1,3]oxazine-2,6-diamine,
rac-$N^2$-(7-Methoxy-indan-1-yl)-$N^6$-(4-trifluoromethyl-pyrimidin-2-yl)-4H-benzo[d][1,3]oxazine-2,6-diamine,
Cyclopropanecarboxylic acid {2-[(5-methyl-furan-2-ylmethyl)-amino]-4H-benzo[d][1,3]oxazin-6-yl}-amide,
N-[2-((R)-Indan-1-ylamino)-4H-benzo[d][1,3]oxazin-6-yl]-benzenesulfonamide,
N-{2-[(5-Methyl-furan-2-ylmethyl)-amino]-4H-benzo[d][1,3]oxazin-6-yl}-2-(4-methyl-piperazin-1-yl)-acetamide,
N-{2-[(5-Methyl-furan-2-ylmethyl)-amino]-4H-benzo[d][1,3]oxazin-6-yl}-2-morpholin-4-yl-acetamide,
rac-N-[2-(7-Methoxy-indan-1-ylamino)-4H-benzo[d][1,3]oxazin-6-yl]-2-(4-methyl-piperazin-1-yl)-acetamide,
$N^2$-(2-Phenoxy-ethyl)-4H-benzo[d][1,3]oxazine-2,6-diamine,
$N^2$-(R)-Indan-1-yl-$N^6$-pyridin-3-ylmethyl-4H-benzo[d][1,3]oxazine-2,6-diamine,
$N^2$-(R)-Indan-1-yl-$N^6$-thiazol-2-ylmethyl-4H-benzo[d][1,3]oxazine-2,6-diamine,
rac-Cyclopropanecarboxylic acid [2-(chroman-4-ylamino)-4H-benzo[d][1,3]oxazin-6-yl]-amide,
rac-N,N-(Dimethyl)-N'-{2-(Chroman-4-ylamino)-4H-benzo[d][1,3]oxazin-6-yl}-sulfamide,
$N^2$-Cycloheptyl-4H-benzo[d][1,3]oxazine-2,6-diamine,
N-(2-Cycloheptylamino-4H-benzo[d][1,3]oxazin-6-yl)-2-(4-methyl-piperazin-1-yl)-acetamide,
$N^6$-Benzyl-$N^2$-cycloheptyl-4H-benzo[d][1,3]oxazine-2,6-diamine,
Cyclopropanecarboxylic acid (2-cycloheptylamino-4H-benzo[d][1,3]oxazin-6-yl)-amide,
Cyclopropanecarboxylic acid [2-(2-phenoxy-ethylamino)-4H-benzo[d][1,3]oxazin-6-yl]-amide,
Cyclopropanesulfonic acid (2-cycloheptylamino-4H-benzo[d][1,3]oxazin-6-yl)-amide,
$N^2$-Cycloheptyl-$N^6$-thiazol-2-ylmethyl-4H-benzo[d][1,3]oxazine-2,6-diamine,
N,N-(Dimethyl)-N'-{2-cycloheptylamino-4H-benzo[d][1,3]oxazin-6-yl-}-sulfamide,
N-(2-Cycloheptylamino-4H-benzo[d][1,3]oxazin-6-yl)-benzenesulfonamide,
$N^2$-(7-Methoxy-indan-1-yl)-$N^6$-(5-methyl-[1,3,4]oxadiazol-2-yl)-4H-benzo[d][1,3]oxazine-2,6-diamine,
rac-N-[2-(7-Methoxy-indan-1-ylamino)-4H-benzo[d][1,3]oxazin-6-yl]-methanesulfonamide,
rac-Cyclopropanesulfonic acid [2-(7-methoxy-indan-1-ylamino)-4H-benzo[d][1,3]oxazin-6-yl]-amide,
rac-N-[2-(7-Methoxy-indan-1-ylamino)-4H-benzo[d][1,3]oxazin-6-yl]-benzenesulfonamide,
$N^2$-Cycloheptyl-$N^6$-(1H-imidazol-2-ylmethyl)-4H-benzo[d][1,3]oxazine-2,6-diamine,
rac-$N^2$-(5-Fluoro-indan-1-yl)-$N^6$-(5-methyl-[1,3,4]oxadiazol-2-yl)-4H-benzo[d][1,3]oxazine-2,6-diamine,
rac-$N^2$-(4-Methoxy-2,3-dihydro-benzofuran-3-yl)-$N^6$-(5-methyl-[1,3,4]oxadiazol-2-yl)-4H-benzo[d][1,3]oxazine-2,6-diamine,
Cyclopropanesulfonic acid [2-(2-phenoxy-ethylamino)-4H-benzo[d][1,3]oxazin-6-yl]-amide,
N-[2-(2-Phenoxy-ethylamino)-4H-benzo[d][1,3]oxazin-6-yl]-benzenesulfonamide,
N,N-(Dimethyl)-N'-{2-(2-Phenoxy-ethylamino)-4H-benzo[d][1,3]oxazin-6-yl}-sulfamide,
$N^6$-(5-Cyclopropyl-[1,3,4]oxadiazol-2-yl)-$N^2$-(7-methoxy-indan-1-yl)-4H-benzo[d][1,3]oxazine-2,6-diamine,
$N^6$-(2-tert-Butyl-2H-tetrazol-5-yl)-$N^2$-(7-methoxy-indan-1-yl)-4H-benzo[d][1,3]oxazine-2,6-diamine,
Cyclopropanesulfonic acid [2-(4-methoxy-2,3-dihydro-benzofuran-3-ylamino)-4H-benzo[d][1,3]oxazin-6-yl]-amide,
N-[2-(4-Methoxy-2,3-dihydro-benzofuran-3-ylamino)-4H-benzo[d][1,3]oxazin-6-yl]-methanesulfonamide,
N-[2-(4-Methoxy-2,3-dihydro-benzofuran-3-ylamino)-4H-benzo[d][1,3]oxazin-6-yl]-benzenesulfonamide,
2-(3-Hydroxymethyl-4-methyl-piperazin-1-yl)-N-[2-(7-methoxy-indan-1-ylamino)-4H-benzo[d][1,3]oxazin-6-yl]-acetamide,
2-((R)-Indan-1-ylamino)-4H-benzo[d][1,3]oxazine-6-carbonitrile,
$N^2$-(R)-Indan-1-yl-$N^6$-(5-methyl-[1,3,4]oxadiazol-2-yl)-4H-benzo[d][1,3]oxazine-2,6-diamine,
$N^2$-(3-Cyclopropyl-phenyl)-4H-benzo[d][1,3]oxazine-2,6-diamine,
rac-N-[2-(Chroman-4-ylamino)-4H-benzo[d][1,3]oxazin-6-yl]-2-(4-methyl-piperazin-1-yl)-acetamide,
rac-N-[2-(Chroman-4-ylamino)-4H-benzo[d][1,3]oxazin-6-yl]-2-morpholin-4-yl-acetamide,
2-(4-Methyl-piperazin-1-yl)-N-[2-(2-phenoxy-ethylamino)-4H-benzo[d][1,3]oxazin-6-yl]-acetamide,
2-Morpholin-4-yl-N-[2-(2-phenoxy-ethylamino)-4H-benzo[d][1,3]oxazin-6-yl]-acetamide,
1-(2-Cycloheptylamino-4H-benzo[d][1,3]oxazin-6-yl)-3-(1-isopropyl-piperidin-4-yl)-urea,
$N^2$-(3-Cyclopropyl-phenyl)-$N^6$-(1H-imidazol-2-ylmethyl)-4H-benzo[d][1,3]oxazine-2,6-diamine,
N-[2-(3-Cyclopropyl-phenylamino)-4H-benzo[d][1,3]oxazin-6-yl]-2-(4-methyl-piperazin-1-yl)-acetamide,
$N^2$-(3-Cyclopropyl-phenyl)-$N^6$-thiazol-2-ylmethyl-4H-benzo[d][1,3]oxazine-2,6-diamine,
Cyclopropanecarboxylic acid [2-(3-cyclopropyl-phenylamino)-4H-benzo[d][1,3]oxazin-6-yl]-amide,
(6-Aminomethyl-4H-benzo[d][1,3]oxazin-2-yl)-(R)-indan-1-yl-amine,
N-Hydroxy-2-((R)-indan-1-ylamino)-4H-benzo[d][1,3]oxazine-6-carboxamidine,
$N^2$-(2,2-Dimethyl-2,3-dihydro-benzofuran-7-yl)-$N^6$-(1H-imidazol-2-ylmethyl)-4H-benzo[d][1,3]oxazine-2,6-diamine,
4-Fluoro-N-[2-((R)-indan-1-ylamino)-4H-benzo[d][1,3]oxazin-6-ylmethyl]-benzamide,
(R)-Indan-1-yl-[6-(5-methyl-[1,2,4]oxadiazol-3-yl)-4H-benzo[d][1,3]oxazin-2-yl]-amine,
(R)-Indan-1-yl-(6-vinyl-4H-benzo[d][1,3]oxazin-2-yl)-amine,
N'-{2-[(3-cyclopropylphenyl)amino]-4H-benzo[d][1,3]oxazin-6-yl}-N,N-dimethylsulfamide,
$N^6$-Benzyl-$N^2$-(3-cyclopropyl-phenyl)-4H-benzo[d][1,3]oxazine-2,6-diamine,
1-[2-(3-Cyclopropyl-phenylamino)-4H-benzo[d][1,3]oxazin-6-yl]-3-(1-isopropyl-piperidin-4-yl)-urea,
$N^2$-(R)-Indan-1-yl-$N^6$-(5-trifluoromethyl-[1,3,4]oxadiazol-2-yl)-4H-benzo[d][1,3]oxazine-2,6-diamine,
1-[2-(2,2-Dimethyl-2,3-dihydro-benzofuran-7-ylamino)-4H-benzo[d][1,3]oxazin-6-yl]-3-isopropyl-urea,
(R)-Indan-1-yl-[6-((E)-styryl)-4H-benzo[d][1,3]oxazin-2-yl]-amine,
rac-2-(4-Methoxy-2,3-dihydro-benzofuran-3-ylamino)-4H-benzo[d][1,3]oxazine-6-carbonitrile,
rac-2-(7-Methoxy-indan-1-ylamino)-4H-benzo[d][1,3]oxazine-6-carbonitrile,
(R)-Indan-1-yl-[6-((E)-2-pyridin-3-yl-vinyl)-4H-benzo[d][1,3]oxazin-2-yl]-amine, $N^2$-(7-Methoxy-indan-1-yl)-$N^6$-(5-trifluoromethyl-[1,3,4] oxadiazol-2-yl)-4H-benzo[d][1,3]oxazine-2,6-diamine, $N^2$-(4-Methoxy-2,3-dihydro-benzofuran-3-yl)-$N^6$-(5-trifluoromethyl-[1,3,4]oxadiazol-2-yl)-4H-benzo[d][1,3]oxazine-2,6-diamine, N-[2-(7-Methoxy-indan-1-ylamino)-4H-benzo[d][1,3]oxazin-6-yl]-2-(3-methoxymethyl-4-methyl-piperazin-1-yl)-acetamide, N-[2-((R)-Indan-1-ylamino)-4H-benzo[d][1,3]oxazin-6-yl]-2-(3-methoxymethyl-4-methyl-piperazin-1-yl)-acetamide, $N^2$-(5-Fluoro-indan-1-yl)-$N^6$-(5-trifluoromethyl-[1,3,4]oxadiazol-2-yl)-4H-benzo[d][1,3]oxazine-2,6-diamine, Cyclopropanesulfonic acid [2-(3-cyclopropyl-phenylamino)-4H-benzo[d][1,3]oxazin-6-yl]-amide, N-[2-(3-Cyclopropyl-phenylamino)-4H-benzo[d][1,3]oxazin-6-yl]-benzenesulfonamide, 1-[2-(3-Cyclopropyl-phenylamino)-4H-benzo[d][1,3]oxazin-6-yl]-3-isopropyl-urea, (6-Cyclopropyl-4H-benzo[d][1,3]oxazin-2-yl)-(R)-indan-1-yl-amine, $N^2$-Cyclooctyl-4H-benzo[d][1,3]oxazine-2,6-diamine, 1-(2-Cycloheptylamino-4H-benzo[d][1,3]oxazin-6-yl)-3-isopropyl-urea, Cyclopropanecarboxylic acid (2-cyclooctylamino-4H-benzo[d][1,3]oxazin-6-yl)-amide, N-(2-Cyclooctylamino-4H-benzo[d][1,3]oxazin-6-yl)-2-(4-methyl-piperazin-1-yl)-acetamide, endo-N-[2-((R)-Indan-1-ylamino)-4H-benzo[d][1,3]oxazin-6-yl]-2-(9-methyl-3oxa-9-aza-bicyclo[3.3.1]non-7-yl)-acetamide, 2-((3SR,5SR)-3,5-Bis-(methoxymethyl)-4-methyl-piperazin-1-yl)-N-[2-((R)-indan-1-ylamino)-4H-benzo[d][1,3]oxazin-6-yl]-acetamide, and N-[2-((R)-Indan-1-ylamino)-4H-benzo[d][1,3]oxazin-6-yl]-2-(9-methyl-3-bicyclo[3.3.1]non-7-yl)-acetamide.

Even more preferred compounds of formula (I) of present invention are those selected from the group consisting of:

Cyclopropanecarboxylic acid [2-((R)-indan-1-ylamino)-4H-benzo[d][1,3]oxazin-6-yl]-amide, (R)-$N^2$-indan-1-yl-4-H-benzo[d][1,3]oxazine-2,6-diamine, Cyclopropanecarboxylic acid [2-(7-methoxy-indan-1-ylamino)-4H-benzo[d][1,3]oxazin-6-yl]-amide, N2-(R)-Indan-1-yl-$N^6$-thiazol-2-ylmethyl-4H-benzo[d][1,3]oxazine-2,6-diamine, N2-(7-Methoxy-indan-1-yl)-4H-benzo[d][1,3]oxazine-2,6-diamine, N2-(5-Fluoro-indan-1-yl)-4H-benzo[d][1,3]oxazine-2,6-diamine, Cyclopropanecarboxylic acid (2-cyclooctylamino-4H-benzo[d][1,3]oxazin-6-yl)-amide, Cyclopropanecarboxylic acid [2-(5-fluoro-indan-1-ylamino)-4H-benzo[d][1,3]oxazin-6-yl]-amide, N2-(R)-Indan-1-yl-$N^6$-(5-methyl-[1,3,4]oxadiazol-2-yl)-4H-benzo[d][1,3]oxazine-2,6-diamine, N-[2-(7-Methoxy-indan-1-ylamino)-4H-benzo[d][1,3]oxazin-6-yl]-2-(4-methyl-piperazin-1-yl)-acetamide, $N^6$-(5-Cyclopropyl-[1,3,4]oxadiazol-2-yl)-$N^2$-(7-methoxy-indan-1-yl)-4H-benzo[d][1,3]oxazine-2,6-diamine, $N^2$-(R)-Indan-1-yl-$N^6$-pyridin-3-ylmethyl-4H-benzo[d][1,3]oxazine-2,6-diamine, Cyclopropanesulfonic acid [2-((R)-indan-1-ylamino)-4H-benzo[d][1,3]oxazin-6-yl]-amide, N-[2-((R)-Indan-1-ylamino)-4H-benzo[d][1,3]oxazin-6-yl]-2-(4-methyl-piperazin-1-yl)-acetamide, Cyclopropanecarboxylic acid [2-(8-methoxy-1,2,3,4-tetrahydro-naphthalen-1-ylamino)-4H-benzo[d][1,3]oxazin-6-yl]-amide, and 1-(2-Cycloheptylamino-4H-benzo[d][1,3]oxazin-6-yl)-3-isopropyl-urea, or a pharmaceutically acceptable salt or ester thereof.

The present compounds of formula (I), their starting materials, their pharmaceutically acceptable salts, and their optical isomers can be prepared by methods known in the art. For example, a process to synthesize representative compounds of formula (I), wherein $R^1$, $R^2$, X and Y are as defined above, can be used which comprises one of the following steps:

a) protecting the alcohol function of compound (1),

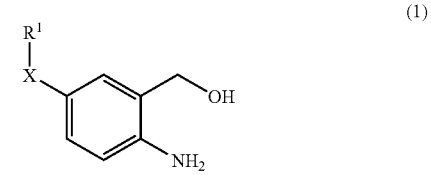
(1)

preferably by reacting compound (1) with a silyl group containing compound, more preferably tert-butyldimethylsilyl or tert-butyldiphenylsilyl, to yield compound (2)

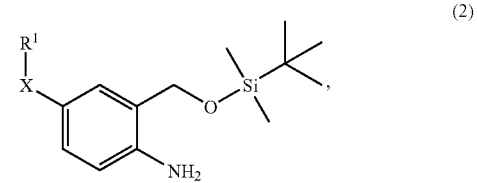
(2)

wherein the alcohol function is protected with a silyl protecting group, b) transforming the amino group of compound (2) into an isothiocyanate, preferably by reacting compound (2) with thiophosgene in the presence of sodium hydrogen carbonate in a chlorinated solvent, more preferably dichloromethane or chloroform, to yield compound (3)

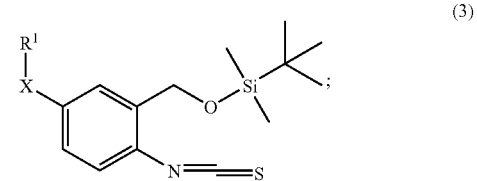
(3)

c) reacting compound (3) with an amine $H_2N-Y-R^2$ to yield compound (4)

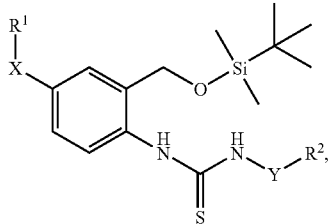

(4)

wherein the reaction between the isothiocyanate function of compound (3) and the amino function of H$_2$N—Y—R$^2$ form a thiourea function in compound (4);

d) removing the alcohol function protecting group of compound (4), preferably by reacting compound (4) with a fluoride compound, more preferably tetrabutylammonium fluoride to yield the (2-hydroxymethyl-phenyl)-thiourea of general formula (5)

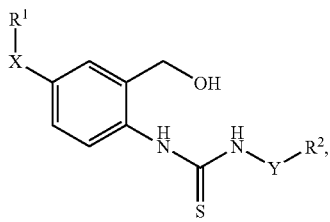

(5)

e) and reacting the (2-hydroxymethyl-phenyl)-thiourea of general formula (5) with a carbodiimide reagent, preferably 1-(3-dimethylaminopropyl)-3-ethylcarbodiimide hydrochloride, dicyclohexylcarbodiimide or diisopropylcarbodiimide to yield the 4H-benzo[d][1,3]oxazin-2yl-amine of general formula (I).

Scheme 1

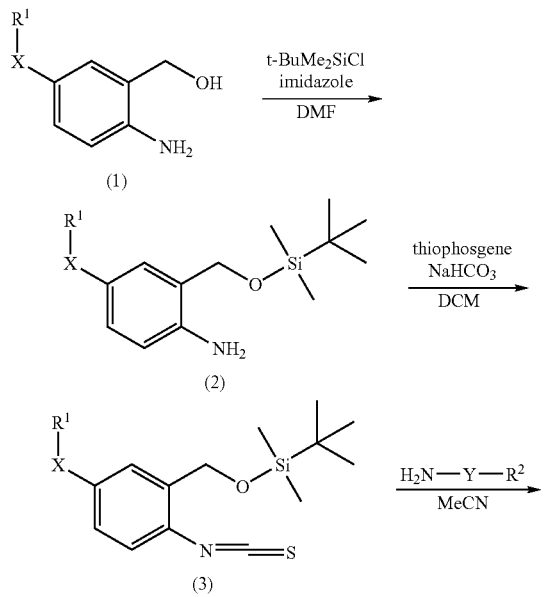

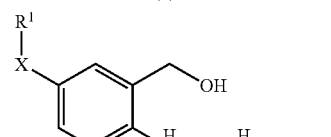

(4)

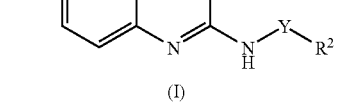

(5)

wherein X, Y, R$^1$ and R$^2$ are as defined above.

In accordance with scheme 1, compounds of formula (I) can be prepared as shown in the following description of the general synthesis of 4H-benzo[d][1,3]oxazin-2yl-amines:

The alcohol function of a 2-aminobenzyl alcohol with the general formula (1) substituted in 5-position with X—R$^1$ in which X and R$^1$ are defined as described above is protected with a silyl protecting group, like e.g. tert-butyldimethylsilyl or tert-butyldiphenylsilyl, by reaction with the corresponding chlorosilane, like e.g. tert-butyldimethyl(chloro)silane (t-BuMe$_2$SiCl) or tert-butyldiphenyl(chloro)silane, in the presence of a base, like e.g. imidazole or the combination of either triethylamine or diisopropylethylamine with 4-dimethylaminopyridine or imidazole, in an organic solvent, like e.g. dimethylformamide (DMF), dimethylacetamide or N-methylpyrrolidinone, at temperatures between 0 and 40° C. to produce compounds of general formula (2). The amino group of compounds of general formula (2) is transformed into an isothiocyanate of general formula (3) by reaction with e.g. thiophosgene in the presence of sodium hydrogen carbonate in a chlorinated solvent, like e.g. dichloromethane (DCM) or chloroform, at temperatures between 0 and 35° C. as e.g. described in *Tetrahedron Letters* 2006, 47, 3953. The isothiocyanate of general formula (3) is then reacted with an amine of general formula R$^2$—Y—NH$_2$ in which Y and R$^2$ are defined as described above in an organic solvent, like e.g. acetonitrile (MeCN) or tetrahydrofuran, at temperatures between −20 and 50° C. to produce thioureas of general formula (4). The silyl protecting group in compounds of general formula (4) is then removed by treatment with a fluoride source, like e.g. tetrabutylammonium fluoride (TBAF), in an organic solvent, like e.g. acetonitrile, tetrahydrofuran or dichloromethane, at temperatures between −20 and 35° C. to give compounds of the general formula (5). These (2-hydroxymethyl-phenyl)-thioureas of general formula (5) are then treated with a carbodiimide reagent, like e.g. 1-(3-dimethylaminopropyl)-3-ethylcarbodiimide hydrochloride (EDC.HCl), dicyclohexylcarbodiimide (DCC) or diisopropylcarbodiimide, in an organic solvent, like e.g. acetonitrile or tetrahydrofuran, at temperatures between 50 and 90° C. to yield the desired 4H-benzo[d][1,3]oxazin-2yl-amines of general formula (I). A similar procedure for this cyclization can be found in *Bulletin of the Korean Chemical Society* 2001, 22(11), 1270. The steps reacting the isothiocyanate of general formula (3) with an amine of general formula $R^2$—Y—$NH_2$— until the final isolation of the desired 4H-benzo[d][1,3]oxazin-2yl-amines of general formula (I) can be performed in one reaction vessel by successive addition of the reagents as described above. Experimental details can be found in the corresponding examples.

The corresponding salts with acids can be obtained by standard methods known to the person skilled in the art, e.g. by dissolving the compound of formula (I) in a suitable solvent such as e.g. dioxan or THF and adding an appropriate amount of the corresponding acid. The products can usually be isolated by filtration or by chromatography. The conversion of a compound of formula (I) into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

It will be appreciated that the compounds of general formula (I) in this invention can be derivatized at functional groups to provide derivatives which are capable of conversion back to the parent compound in vivo.

As mentioned earlier, the compounds of formula (I) and their pharmaceutically acceptable addition salts possess valuable pharmaceutical properties. It has been found that the compounds of the present invention are active on the $5\text{-}HT_{5A}$ receptor and therefore suitable for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders, Parkinson's disease, psychiatric disorders or gastrointestinal disorders.

The invention likewise embraces a compound of formula (I) for the use as a medicament.

The invention therefore also relates to a pharmaceutical composition comprising at least one compound of formula (I) and a pharmaceutically acceptable excipient, especially for the use in the prevention or treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders, Parkinson's disease, psychiatric disorders or gastrointestinal disorders.

The invention likewise embraces a compound of formula (I) for use as therapeutically active substances, especially as therapeutically active substances for the treatment or prevention of diseases which are related to the $5\text{-}HT_{5A}$ receptor, particularly for the treatment or prevention of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders, Parkinson's disease, psychiatric disorders or gastrointestinal disorders.

In another preferred embodiment, the invention relates to a method for the treatment or prevention of diseases which are related to the $5\text{-}HT_{5A}$ receptor, particularly for the treatment or prevention of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders, Parkinson's disease, psychiatric disorders or gastrointestinal disorders, which method comprises administering a compound as defined above to a human being or animal.

The treatment or prevention of depression, anxiety, sleep disorders and schizophrenia is preferred.

The compounds were investigated in accordance with the test given hereinafter:

Test Description

A [$^3$H]LSD radioligand binding assay was used to determine the affinity of the compounds for the recombinant human $5\text{-}HT_{5A}$ receptor, in membranes from transiently (cDNA) expressed $5\text{-}HT_{5A}$ receptors in Human Embryonic Kidney-EBNA (HEK-EBNA) cells. Assay buffer consisted of Tris (50 mM) buffer containing 1 mM EGTA, 10 mM $MgCl_2$ (pH 7.4) and 10 µM pargyline. The binding assay was carried out in 96-well-plates in the presence of [$^3$H]LSD (approximately 1 nM), approximately 2 µg/well of membrane protein, and 0.5 mg of Ysi-poly-1-lysine SPA beads in a final volume of 200 µl of buffer. Non-specific binding was defined using methiothepin 2 µM. Compounds were tested at 10 concentrations. All assays were conducted in duplicate and repeated at least two times. Assay plates were incubated for 120 min at room temperature before centrifugation. Bound ligand was determined using a Packard Topcount scintillation counter. $IC_{50}$ values were calculated using a non-linear curve fitting program and Ki values calculated using the Cheng-Prussoff equation.

The activity of the compounds according to the invention is exemplified in the Table below:

| Ex. | Systematic Name | $K_i/\mu M$ |
| --- | --- | --- |
| 1 | (2-Methoxy-benzyl)-(6-nitro-4H-benzo[d][1,3]oxazin-2-yl)-amine | 0.39023 |
| 2 | (R)—$N^2$-Indan-1-yl-4H-benzo[d][1,3]oxazine-2,6-diamine | 0.00104 |
| 3 | N-[2-((R)-Indan-1-ylamino)-4H-benzo[d][1,3]oxazin-6-yl]-2-(4-methyl-piperazin-1-yl)-acetamide | 0.00184 |
| 4 | $N^2$-(2-Methoxy-benzyl)-4H-benzo[d][1,3]oxazine-2,6-diamine | 0.00605 |

-continued

| Ex. | Systematic Name | $K_i/\mu M$ |
|---|---|---|
| 5 | rac-(4-Methoxy-2,3-dihydro-benzofuran-3-yl)-(6-nitro-4H-benzo[d][1,3]oxazin-2-yl)-amine | 0.36812 |
| 6 | rac-$N^2$-(4-Methoxy-2,3-dihydro-benzofuran-3-yl)-4H-benzo[d][1,3]oxazine-2,6-diamine | 0.00783 |
| 7 | Cyclopropanecarboxylic acid [2-(2-methoxy-benzylamino)-4H-benzo[d][1,3]oxazin-6-yl]-amide | 0.00298 |
| 8 | rac-2-Chloro-N-[2-(4-methoxy-2,3-dihydro-benzofuran-3-ylamino)-4H-benzo[d][1,3]oxazin-6-yl]-acetamide | 0.02065 |
| 9 | rac-N-[2-(4-Methoxy-2,3-dihydro-benzofuran-3-ylamino)-4H-benzo[d][1,3]oxazin-6-yl]-2-(4-methyl-piperazin-1-yl)-acetamide | 0.00569 |
| 10 | rac-$N^2$-(7-Methoxy-indan-1-yl)-4H-benzo[d][1,3]oxazine-2,6-diamine | 0.0012 |
| 11 | rac-$N^2$-(5-Fluoro-indan-1-yl)-4H-benzo[d][1,3]oxazine-2,6-diamine | 0.00126 |
| 12 | rac-2-(4-Isopropyl-piperazin-1-yl)-N-[2-(4-methoxy-2,3-dihydro-benzofuran-3-ylamino)-4H-benzo[d][1,3]oxazin-6-yl]-acetamide | 0.00928 |
| 13 | rac-N-[2-(4-Methoxy-2,3-dihydro-benzofuran-3-ylamino)-4H-benzo[d][1,3]oxazin-6-yl]-2-morpholin-4-yl-acetamide | 0.0406 |
| 14 | rac-1-(1-Isopropyl-piperidin-4-yl)-3-[2-(4-methoxy-2,3-dihydro-benzofuran-3-ylamino)-4H-benzo[d][1,3]oxazin-6-yl]-urea | 0.00437 |
| 15 | rac-1-(1-Isopropyl-piperidin-4-yl)-3-[2-(4-methoxy-2,3-dihydro-benzofuran-3-ylamino)-4H-benzo[d][1,3]oxazin-6-yl]-1-methyl-urea | 0.00608 |
| 16 | rac-1-Isopropyl-3-[2-(4-methoxy-2,3-dihydro-benzofuran-3-ylamino)-4H-benzo[d][1,3]oxazin-6-yl]-urea | 0.00293 |
| 17 | rac-2-Methoxy-N-[2-(4-methoxy-2,3-dihydro-benzofuran-3-ylamino)-4H-benzo[d][1,3]oxazin-6-yl]-acetamide | 0.02609 |
| 18 | Cyclopropanecarboxylic acid [2-((R)-indan-1-ylamino)-4H-benzo[d][1,3]oxazin-6-yl]-amide | 0.00083 |
| 19 | N-[2-((R)-Indan-1-ylamino)-4H-benzo[d][1,3]oxazin-6-yl]-2-methoxy-acetamide | 0.0041 |
| 20 | rac-Cyclopropanecarboxylic acid [2-(5-fluoro-indan-1-ylamino)-4H-benzo[d][1,3]oxazin-6-yl]-amide | 0.00136 |
| 21 | rac-N-[2-(5-Fluoro-indan-1-ylamino)-4H-benzo[d][1,3]oxazin-6-yl]-2-methoxy-acetamide | 0.0055 |
| 22 | rac-$N^2$-(8-Methoxy-1,2,3,4-tetrahydro-naphthalen-1-yl)-4H-benzo[d][1,3]oxazine-2,6-diamine | 0.00772 |
| 23 | rac-Cyclopropanecarboxylic acid [2-(8-methoxy-1,2,3,4-tetrahydro-naphthalen-1-ylamino)-4H-benzo[d][1,3]oxazin-6-yl]-amide | 0.00185 |
| 24 | rac-2-Methoxy-N-[2-(7-methoxy-indan-1-ylamino)-4H-benzo[d][1,3]oxazin-6-yl]-acetamide | 0.00483 |
| 25 | Cyclopropanecarboxylic acid [2-(7-methoxy-indan-1-ylamino)-4H-benzo[d][1,3]oxazin-6-yl]-amide | 0.00106 |
| 26 | N-[2-(2-Methoxy-benzylamino)-4H-benzo[d][1,3]oxazin-6-yl]-2-(4-methyl-piperazin-1-yl)-acetamide | 0.00612 |
| 27 | N,N-(Dimethyl)-N'-{2-((R)-indan-1-ylamino)-4H-benzo[d][1,3]oxazin-6-yl}-sulfamide | 0.00236 |
| 28 | 2-[4-(2-Hydroxy-ethyl)-piperazin-1-yl]-N-[2-(2-methoxy-benzylamino)-4H-benzo[d][1,3]oxazin-6-yl]-acetamide | 0.01024 |
| 29 | 2-(4-Isopropyl-piperazin-1-yl)-N-[2-(2-methoxy-benzylamino)-4H-benzo[d][1,3]oxazin-6-yl]-acetamide | 0.01093 |
| 30 | Piperidine-1-sulfonic acid [2-((R)-indan-1-ylamino)-4H-benzo[d][1,3]oxazin-6-yl]-amide | 0.0042 |
| 31 | Morpholine-4-sulfonic acid [2-((R)-indan-1-ylamino)-4H-benzo[d][1,3]oxazin-6-yl]-amide | 0.00438 |
| 32 | (6-Bromo-4H-benzo[d][1,3]oxazin-2-yl)-(R)-indan-1-yl-amine | 0.02524 |
| 33 | (R)—$N^2$-(1,2,3,4-Tetrahydro-naphthalen-1-yl)-4H-benzo[d][1,3]oxazine-2,6-diamine | 0.00785 |
| 34 | rac-$N^2$-(6-Fluoro-2,3-dihydro-benzofuran-3-yl)-4H-benzo[d][1,3]oxazine-2,6-diamine | 0.00426 |
| 35 | $N^2$—(R)-Indan-1-yl-$N^6$-(6-trifluoromethyl-pyridin-2-yl)-4H-benzo[d][1,3]oxazine-2,6-diamine | 0.00616 |
| 37 | N-[2-((R)-Indan-1-ylamino)-4H-benzo[d][1,3]oxazin-6-yl]-2-morpholin-4-yl-acetamide | 0.00874 |
| 38 | 2-(4-Methyl-piperazin-1-yl)-N-{2-[(R)-(1,2,3,4-tetrahydro-naphthalen-1-yl)amino]-4H-benzo[d][1,3]oxazin-6-yl}-acetamide | 0.00316 |
| 39 | 2-Morpholin-4-yl-N-{2-[(R)-(1,2,3,4-tetrahydro-naphthalen-1-yl)amino]-4H-benzo[d][1,3]oxazin-6-yl}-acetamide | 0.02282 |
| 40 | 2-(2-Methoxy-ethylamino)-N-{2-[(R)-(1,2,3,4-tetrahydro-naphthalen-1-yl)amino]-4H-benzo[d][1,3]oxazin-6-yl}-acetamide | 0.03298 |
| 41 | 2-(2-Hydroxy-2-methyl-propylamino)-N-{2-[(R)-(1,2,3,4-tetrahydro-naphthalen-1-yl)amino]-4H-benzo[d][1,3]oxazin-6-yl}-acetamide | 0.033 |
| 42 | rac-N-[2-(6-Fluoro-2,3-dihydro-benzofuran-3-ylamino)-4H-benzo[d][1,3]oxazin-6-yl]-2-(2-methoxy-ethylamino)-acetamide | 0.0564 |
| 43 | rac-N-[2-(6-Fluoro-2,3-dihydro-benzofuran-3-ylamino)-4H-benzo[d][1,3]oxazin-6-yl]-2-(2-hydroxy-2-methyl-propylamino)-acetamide | 0.05032 |
| 44 | rac-N-[2-(6-Fluoro-2,3-dihydro-benzofuran-3-ylamino)-4H-benzo[d][1,3]oxazin-6-yl]-2-(4-methyl-piperazin-1-yl)-acetamide | 0.0065 |

-continued

| Ex. | Systematic Name | $K_i/\mu M$ |
|---|---|---|
| 45 | rac-N-[2-(6-Fluoro-2,3-dihydro-benzofuran-3-ylamino)-4H-benzo[d][1,3]oxazin-6-yl]-2-morpholin-4-yl-acetamide | 0.04074 |
| 46 | $N^2$—(R)-Indan-1-yl-$N^6$-(4-trifluoromethyl-pyrimidin-2-yl)-4H-benzo[d][1,3]oxazine-2,6-diamine | 0.0071 |
| 47 | $N^6$-(4,6-Dimethyl-pyrimidin-2-yl)-$N^2$—(R)-indan-1-yl-4H-benzo[d][1,3]oxazine-2,6-diamine | 0.00356 |
| 48 | N-[2-((R)-Indan-1-ylamino)-4H-benzo[d][1,3]oxazin-6-yl]-acetamide | 0.00363 |
| 49 | rac-N,N-(Dimethyl)-N'-{2-(4-methoxy-2,3-dihydro-benzofuran-3-ylamino)-4H-benzo[d][1,3]oxazin-6-yl}-sulfamide | 0.0211 |
| 50 | Piperidine-1-sulfonic acid [2-(4-methoxy-2,3-dihydro-benzofuran-3-ylamino)-4H-benzo[d][1,3]oxazin-6-yl]-amide | 0.02687 |
| 51 | N-[2-(4-Methoxy-2,3-dihydro-benzofuran-3-ylamino)-4H-benzo[d][1,3]oxazin-6-yl]-acetamide | 0.02367 |
| 52 | N-[2-(7-Methoxy-indan-1-ylamino)-4H-benzo[d][1,3]oxazin-6-yl]-acetamide | 0.00498 |
| 53 | rac-(6-Bromo-4H-benzo[d][1,3]oxazin-2-yl)-(5-fluoro-indan-1-yl)-amine | 0.04364 |
| 54 | rac-(6-Bromo-4H-benzo[d][1,3]oxazin-2-yl)-(4-methoxy-2,3-dihydro-benzofuran-3-yl)-amine | 0.12466 |
| 55 | rac-N-[2-(7-Methoxy-indan-1-ylamino)-4H-benzo[d][1,3]oxazin-6-yl]-2-morpholin-4-yl-acetamide | 0.0103 |
| 56 | rac-N-[2-(5-Fluoro-indan-1-ylamino)-4H-benzo[d][1,3]oxazin-6-yl]-2-morpholin-4-yl-acetamide | 0.01303 |
| 57 | rac-$N^2$-(5-Fluoro-indan-1-yl)-$N^6$-(6-trifluoromethyl-pyridin-2-yl)-4H-benzo[d][1,3]oxazine-2,6-diamine | 0.00606 |
| 58 | rac-$N^2$-(5-Fluoro-indan-1-yl)-$N^6$-(4-trifluoromethyl-pyrimidin-2-yl)-4H-benzo[d][1,3]oxazine-2,6-diamine | 0.0068 |
| 59 | rac-$N^2$-(4-Methoxy-2,3-dihydro-benzofuran-3-yl)-$N^6$-(6-trifluoromethyl-pyridin-2-yl)-4H-benzo[d][1,3]oxazine-2,6-diamine | 0.00782 |
| 60 | rac-$N^2$-(4-Methoxy-2,3-dihydro-benzofuran-3-yl)-$N^6$-(4-trifluoromethyl-pyrimidin-2-yl)-4H-benzo[d][1,3]oxazine-2,6-diamine | 0.01254 |
| 61 | rac-N,N-(Dimethyl)-N'-{2-(7-Methoxy-indan-1-ylamino)-4H-benzo[d][1,3]oxazin-6-yl}-sulfamide | 0.0026 |
| 62 | rac-Piperidine-1-sulfonic acid [2-(7-methoxy-indan-1-ylamino)-4H-benzo[d][1,3]oxazin-6-yl]-amide | 0.00326 |
| 63 | rac-Morpholine-4-sulfonic acid [2-(7-methoxy-indan-1-ylamino)-4H-benzo[d][1,3]oxazin-6-yl]-amide | 0.00332 |
| 64 | rac-N,N-(Dimethyl)-N'-{2-(5-Fluoro-indan-1-ylamino)-4H-benzo[d][1,3]oxazin-6-yl}-sulfamide | 0.00408 |
| 65 | N-[2-((R)-Indan-1-ylamino)-4H-benzo[d][1,3]oxazin-6-yl]-2-thiomorpholin-4-yl-acetamide | 0.00762 |
| 66 | 2-(1,1-Dioxo-1$\lambda^6$-thiomorpholin-4-yl)-N-[2-((R)-indan-1-ylamino)-4H-benzo[d][1,3]oxazin-6-yl]-acetamide | 0.01598 |
| 67 | 2-Imidazol-1-yl-N-[2-((R)-indan-1-ylamino)-4H-benzo[d][1,3]oxazin-6-yl]-acetamide | 0.00742 |
| 68 | 2-(2-Hydroxy-2-methyl-propylamino)-N-[2-((R)-indan-1-ylamino)-4H-benzo[d][1,3]oxazin-6-yl]-acetamide | 0.00923 |
| 69 | N-[2-((R)-Indan-1-ylamino)-4H-benzo[d][1,3]oxazin-6-yl]-2-(2-methoxy-ethylamino)-acetamide | 0.00834 |
| 70 | N-[2-((R)-Indan-1-ylamino)-4H-benzo[d][1,3]oxazin-6-yl]-2-[4-(2,2,2-trifluoro-ethyl)-piperazin-1-yl]-acetamide | 0.03301 |
| 71 | 4-Methyl-piperazine-1-sulfonic acid {2-[(R)-(1,2,3,4-tetrahydro-naphthalen-1-yl)amino]-4H-benzo[d][1,3]oxazin-6-yl}-amide | 0.13815 |
| 72 | 4-Methyl-piperazine-1-sulfonic acid [2-((R)-indan-1-ylamino)-4H-benzo[d][1,3]oxazin-6-yl]-amide | 0.02859 |
| 73 | 2-((exo)-8-Isopropyl-8-aza-bicyclo[3.2.1]oct-3-ylamino)-N-{2-[(R)-(1,2,3,4-tetrahydro-naphthalen-1-yl)amino]-4H-benzo[d][1,3]oxazin-6-yl}-acetamide | 0.06134 |
| 74 | rac-(6-Bromo-4H-benzo[d][1,3]oxazin-2-yl)-(7-methoxy-indan-1-yl)-amine | 0.01384 |
| 75 | rac-$N^2$-Chroman-4-yl-4H-benzo[d][1,3]oxazine-2,6-diamine | 0.01628 |
| 76 | N-[2-((R)-Indan-1-ylamino)-4H-benzo[d][1,3]oxazin-6-yl]-2-((exo)-8-isopropyl-8-aza-bicyclo[3.2.1]oct-3-ylamino)-acetamide | 0.01345 |
| 77 | $N^2$-(5-Methyl-furan-2-ylmethyl)-4H-benzo[d][1,3]oxazine-2,6-diamine | 0.01354 |
| 78 | N-[2-((R)-Indan-1-ylamino)-4H-benzo[d][1,3]oxazin-6-yl]-methanesulfonamide | 0.00444 |
| 79 | Cyclopropanesulfonic acid [2-((R)-indan-1-ylamino)-4H-benzo[d][1,3]oxazin-6-yl]-amide | 0.00181 |
| 80 | rac-$N^2$-(7-Methoxy-indan-1-yl)-$N^6$-(6-trifluoromethyl-pyridin-2-yl)-4H-benzo[d][1,3]oxazine-2,6-diamine | 0.00426 |
| 81 | rac-$N^2$-(7-Methoxy-indan-1-yl)-$N^6$-(4-trifluoromethyl-pyrimidin-2-yl)-4H-benzo[d][1,3]oxazine-2,6-diamine | 0.00716 |
| 82 | Cyclopropanecarboxylic acid {2-[(5-methyl-furan-2-ylmethyl)-amino]-4H-benzo[d][1,3]oxazin-6-yl}-amide | 0.01172 |

| Ex. | Systematic Name | $K_i/\mu M$ |
|---|---|---|
| 83 | N-[2-((R)-Indan-1-ylamino)-4H-benzo[d][1,3]oxazin-6-yl]-benzenesulfonamide | 0.00369 |
| 84 | N-{2-[(5-Methyl-furan-2-ylmethyl)-amino]-4H-benzo[d][1,3]oxazin-6-yl}-2-(4-methyl-piperazin-1-yl)-acetamide | 0.02677 |
| 85 | N-{2-[(5-Methyl-furan-2-ylmethyl)-amino]-4H-benzo[d][1,3]oxazin-6-yl}-2-morpholin-4-yl-acetamide | 0.25145 |
| 86 | rac-N-[2-(7-Methoxy-indan-1-ylamino)-4H-benzo[d][1,3]oxazin-6-yl]-2-(4-methyl-piperazin-1-yl)-acetamide | 0.00143 |
| 87 | $N^2$-(2-Phenoxy-ethyl)-4H-benzo[d][1,3]oxazine-2,6-diamine | 0.0036 |
| 88 | $N^2$—(R)-Indan-1-yl-$N^6$-pyridin-3-ylmethyl-4H-benzo[d][1,3]oxazine-2,6-diamine | 0.00168 |
| 89 | $N^2$—(R)-Indan-1-yl-$N^6$-thiazol-2-ylmethyl-4H-benzo[d][1,3]oxazine-2,6-diamine | 0.00118 |
| 90 | rac-Cyclopropanecarboxylic acid [2-(chroman-4-ylamino)-4H-benzo[d][1,3]oxazin-6-yl]-amide | 0.00828 |
| 91 | rac-N,N-(Dimethyl)-N'-{2-(Chroman-4-ylamino)-4H-benzo[d][1,3]oxazin-6-yl}-sulfamide | 0.0525 |
| 92 | $N^2$-Cycloheptyl-4H-benzo[d][1,3]oxazine-2,6-diamine | 0.01674 |
| 93 | N-(2-Cycloheptylamino-4H-benzo[d][1,3]oxazin-6-yl)-2-(4-methyl-piperazin-1-yl)-acetamide | 0.01084 |
| 94 | $N^6$-Benzyl-$N^2$-cycloheptyl-4H-benzo[d][1,3]oxazine-2,6-diamine | 0.06351 |
| 95 | Cyclopropanecarboxylic acid (2-cycloheptylamino-4H-benzo[d][1,3]oxazin-6-yl)-amide | 0.00553 |
| 96 | Cyclopropanecarboxylic acid [2-(2-phenoxy-ethylamino)-4H-benzo[d][1,3]oxazin-6-yl]-amide | 0.0033 |
| 97 | Cyclopropanesulfonic acid (2-cycloheptylamino-4H-benzo[d][1,3]oxazin-6-yl)-amide | 0.03861 |
| 98 | $N^2$-Cycloheptyl-$N^6$-thiazol-2-ylmethyl-4H-benzo[d][1,3]oxazine-2,6-diamine | 0.01927 |
| 99 | N,N-(Dimethyl)-N'-{2-cycloheptylamino-4H-benzo[d][1,3]oxazin-6-yl-}-sulfamide | 0.04762 |
| 100 | N-(2-Cycloheptylamino-4H-benzo[d][1,3]oxazin-6-yl)-benzenesulfonamide | 0.07473 |
| 101 | $N^2$-(7-Methoxy-indan-1-yl)-$N^6$-(5-methyl-[1,3,4]oxadiazol-2-yl)-4H-benzo[d][1,3]oxazine-2,6-diamine | 0.00241 |
| 102 | rac-N-[2-(7-Methoxy-indan-1-ylamino)-4H-benzo[d][1,3]oxazin-6-yl]-methanesulfonamide | 0.00836 |
| 103 | rac-Cyclopropanesulfonic acid [2-(7-methoxy-indan-1-ylamino)-4H-benzo[d][1,3]oxazin-6-yl]-amide | 0.00282 |
| 104 | rac-N-[2-(7-Methoxy-indan-1-ylamino)-4H-benzo[d][1,3]oxazin-6-yl]-benzenesulfonamide | 0.00868 |
| 105 | $N^2$-Cycloheptyl-$N^6$-(1H-imidazol-2-ylmethyl)-4H-benzo[d][1,3]oxazine-2,6-diamine | 0.03162 |
| 106 | rac-$N^2$-(5-Fluoro-indan-1-yl)-$N^6$-(5-methyl-[1,3,4]oxadiazol-2-yl)-4H-benzo[d][1,3]oxazine-2,6-diamine | 0.00294 |
| 107 | rac-$N^2$-(4-Methoxy-2,3-dihydro-benzofuran-3-yl)-$N^6$-(5-methyl-[1,3,4]oxadiazol-2-yl)-4H-benzo[d][1,3]oxazine-2,6-diamine | 0.01011 |
| 108 | Cyclopropanesulfonic acid [2-(2-phenoxy-ethylamino)-4H-benzo[d][1,3]oxazin-6-yl]-amide | 0.02906 |
| 109 | N-[2-(2-Phenoxy-ethylamino)-4H-benzo[d][1,3]oxazin-6-yl]-benzenesulfonamide | 0.03227 |
| 110 | N,N-(Dimethyl)-N'-{2-(2-Phenoxy-ethylamino)-4H-benzo[d][1,3]oxazin-6-yl}-sulfamide | 0.02412 |
| 111 | $N^6$-(5-Cyclopropyl-[1,3,4]oxadiazol-2-yl)-$N^2$-(7-methoxy-indan-1-yl)-4H-benzo[d][1,3]oxazine-2,6-diamine | 0.00165 |
| 112 | $N^6$-(2-tert-Butyl-2H-tetrazol-5-yl)-$N^2$-(7-methoxy-indan-1-yl)-4H-benzo[d][1,3]oxazine-2,6-diamine | 0.00456 |
| 113 | Cyclopropanesulfonic acid [2-(4-methoxy-2,3-dihydro-benzofuran-3-ylamino)-4H-benzo[d][1,3]oxazin-6-yl]-amide | 0.01256 |
| 114 | N-[2-(4-Methoxy-2,3-dihydro-benzofuran-3-ylamino)-4H-benzo[d][1,3]oxazin-6-yl]-methanesulfonamide | 0.03039 |
| 115 | N-[2-(4-Methoxy-2,3-dihydro-benzofuran-3-ylamino)-4H-benzo[d][1,3]oxazin-6-yl]-benzenesulfonamide | 0.0209 |
| 116 | 2-(3-Hydroxymethyl-4-methyl-piperazin-1-yl)-N-[2-(7-methoxy-indan-1-ylamino)-4H-benzo[d][1,3]oxazin-6-yl]-acetamide | 0.00289 |
| 117 | 2-((R)-Indan-1-ylamino)-4H-benzo[d][1,3]oxazine-6-carbonitrile | 0.01567 |
| 118 | $N^2$—(R)-Indan-1-yl-$N^6$-(5-methyl-[1,3,4]oxadiazol-2-yl)-4H-benzo[d][1,3]oxazine-2,6-diamine | 0.0014 |
| 119 | $N^2$-(3-Cyclopropyl-phenyl)-4H-benzo[d][1,3]oxazine-2,6-diamine | 0.03782 |
| 120 | rac-N-[2-(Chroman-4-ylamino)-4H-benzo[d][1,3]oxazin-6-yl]-2-(4-methyl-piperazin-1-yl)-acetamide | 0.01432 |
| 121 | rac-N-[2-(Chroman-4-ylamino)-4H-benzo[d][1,3]oxazin-6-yl]-2-morpholin-4-yl-acetamide | 0.13545 |
| 122 | 2-(4-Methyl-piperazin-1-yl)-N-[2-(2-phenoxy-ethylamino)-4H-benzo[d][1,3]oxazin-6-yl]-acetamide | 0.00511 |
| 123 | 2-Morpholin-4-yl-N-[2-(2-phenoxy-ethylamino)-4H-benzo[d][1,3]oxazin-6-yl]-acetamide | 0.0414 |

-continued

| Ex. | Systematic Name | $K_i/\mu M$ |
|---|---|---|
| 124 | 1-(2-Cycloheptylamino-4H-benzo[d][1,3]oxazin-6-yl)-3-(1-isopropyl-piperidin-4-yl)-urea | 0.00332 |
| 125 | $N^2$-(3-Cyclopropyl-phenyl)-$N^6$-(1H-imidazol-2-ylmethyl)-4H-benzo[d][1,3]oxazine-2,6-diamine | 0.03719 |
| 126 | N-[2-(3-Cyclopropyl-phenylamino)-4H-benzo[d][1,3]oxazin-6-yl]-2-(4-methyl-piperazin-1-yl)-acetamide | 0.03769 |
| 127 | $N^2$-(3-Cyclopropyl-phenyl)-$N^6$-thiazol-2-ylmethyl-4H-benzo[d][1,3]oxazine-2,6-diamine | 0.03794 |
| 128 | Cyclopropanecarboxylic acid [2-(3-cyclopropyl-phenylamino)-4H-benzo[d][1,3]oxazin-6-yl]-amide | 0.02351 |
| 129 | (6-Aminomethyl-4H-benzo[d][1,3]oxazin-2-yl)-(R)-indan-1-yl-amine | 0.01332 |
| 130 | N-Hydroxy-2-((R)-indan-1-ylamino)-4H-benzo[d][1,3]oxazine-6-carboxamidine | 0.01163 |
| 131 | $N^2$-(2,2-Dimethyl-2,3-dihydro-benzofuran-7-yl)-$N^6$-(1H-imidazol-2-ylmethyl)-4H-benzo[d][1,3]oxazine-2,6-diamine | 0.01792 |
| 132 | 4-Fluoro-N-[2-((R)-indan-1-ylamino)-4H-benzo[d][1,3]oxazin-6-ylmethyl]-benzamide | 0.04798 |
| 133 | (R)-Indan-1-yl-[6-(5-methyl-[1,2,4]oxadiazol-3-yl)-4H-benzo[d][1,3]oxazin-2-yl]-amine | 0.0757 |
| 134 | (R)-Indan-1-yl-(6-vinyl-4H-benzo[d][1,3]oxazin-2-yl)-amine | 0.01353 |
| 135 | N'-{2-[(3-cyclopropylphenyl)amino]-4H-benzo[d][1,3]oxazin-6-yl}-N,N-dimethylsulfamide | 0.07168 |
| 136 | $N^6$-Benzyl-$N^2$-(3-cyclopropyl-phenyl)-4H-benzo[d][1,3]oxazine-2,6-diamine | 0.0613 |
| 137 | 1-[2-(3-Cyclopropyl-phenylamino)-4H-benzo[d][1,3]oxazin-6-yl]-3-(1-isopropyl-piperidin-4-yl)-urea | 0.00532 |
| 138 | $N^2$—(R)-Indan-1-yl-$N^6$-(5-trifluoromethyl-[1,3,4]oxadiazol-2-yl)-4H-benzo[d][1,3]oxazine-2,6-diamine | 0.00876 |
| 139 | 1-[2-(2,2-Dimethyl-2,3-dihydro-benzofuran-7-ylamino)-4H-benzo[d][1,3]oxazin-6-yl]-3-isopropyl-urea | 0.24106 |
| 140 | (R)-Indan-1-yl-[6-((E)-styryl)-4H-benzo[d][1,3]oxazin-2-yl]-amine | 0.01764 |
| 141 | rac-2-(4-Methoxy-2,3-dihydro-benzofuran-3-ylamino)-4H-benzo[d][1,3]oxazine-6-carbonitrile | 0.1597 |
| 142 | rac-2-(7-Methoxy-indan-1-ylamino)-4H-benzo[d][1,3]oxazine-6-carbonitrile | 0.02704 |
| 143 | (R)-Indan-1-yl-[6-((E)-2-pyridin-3-yl-vinyl)-4H-benzo[d][1,3]oxazin-2-yl]-amine | 0.00762 |
| 144 | $N^2$-(7-Methoxy-indan-1-yl)-$N^6$-(5-trifluoromethyl-[1,3,4]oxadiazol-2-yl)-4H-benzo[d][1,3]oxazine-2,6-diamine | 0.00844 |
| 145 | $N^2$-(4-Methoxy-2,3-dihydro-benzofuran-3-yl)-$N^6$-(5-trifluoromethyl-[1,3,4]oxadiazol-2-yl)-4H-benzo[d][1,3]oxazine-2,6-diamine | 0.0402 |
| 146 | N-[2-(7-Methoxy-indan-1-ylamino)-4H-benzo[d][1,3]oxazin-6-yl]-2-(3-methoxymethyl-4-methyl-piperazin-1-yl)-acetamide | 0.0037 |
| 147 | N-[2-((R)-Indan-1-ylamino)-4H-benzo[d][1,3]oxazin-6-yl]-2-(3-methoxymethyl-4-methyl-piperazin-1-yl)-acetamide | 0.00355 |
| 148 | $N^2$-(5-Fluoro-indan-1-yl)-$N^6$-(5-trifluoromethyl-[1,3,4]oxadiazol-2-yl)-4H-benzo[d][1,3]oxazine-2,6-diamine | 0.01409 |
| 149 | Cyclopropanesulfonic acid [2-(3-cyclopropyl-phenylamino)-4H-benzo[d][1,3]oxazin-6-yl]-amide | 0.13774 |
| 150 | N-[2-(3-Cyclopropyl-phenylamino)-4H-benzo[d][1,3]oxazin-6-yl]-benzenesulfonamide | 0.29932 |
| 151 | 1-[2-(3-Cyclopropyl-phenylamino)-4H-benzo[d][1,3]oxazin-6-yl]-3-isopropyl-urea | 0.11376 |
| 152 | (6-Cyclopropyl-4H-benzo[d][1,3]oxazin-2-yl)-(R)-indan-1-yl-amine | 0.02734 |
| 153 | $N^2$-Cyclooctyl-4H-benzo[d][1,3]oxazine-2,6-diamine | 0.01188 |
| 154 | 1-(2-Cycloheptylamino-4H-benzo[d][1,3]oxazin-6-yl)-3-isopropyl-urea | 0.00186 |
| 155 | Cyclopropanecarboxylic acid (2-cyclooctylamino-4H-benzo[d][1,3]oxazin-6-yl)-amide | 0.0013 |
| 156 | N-(2-Cyclooctylamino-4H-benzo[d][1,3]oxazin-6-yl)-2-(4-methyl-piperazin-1-yl)-acetamide | 0.00216 |
| 157 | endo-N-[2-((R)-Indan-1-ylamino)-4H-benzo[d][1,3]oxazin-6-yl]-2-(9-methyl-3-oxa-9-aza-bicyclo[3.3.1]non-7-yl)-acetamide | 0.00298 |
| 158 | 2-((3SR,5SR)-3,5-Bis-(methoxymethyl)-4-methyl-piperazin-1-yl)-N-[2-((R)-indan-1-ylamino)-4H-benzo[d][1,3]oxazin-6-yl]-acetamide | 0.01606 |
| 159 | N-[2-((R)-Indan-1-ylamino)-4H-benzo[d][1,3]oxazin-6-yl]-2-(9-methyl-3-oxa-7,9-diaza-bicyclo[3.3.1]non-7-yl)-acetamide | 0.0189 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include disorders of the central nervous system, for example the treatment of anxiety, depression, sleep disorders and schizophrenia.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula (I) or of the corresponding amount of a pharmaceutically acceptable salt thereof. The daily dosage at which compounds of the invention can be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula (I) | 5 | 25 | 100 | 500 |
| 2. | Anhydrous Lactose | 125 | 105 | 30 | 150 |
| 3. | Corn Starch | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The following examples are provided for illustration of the invention. They should not be considered as limiting the scope of the invention, but merely as being representative thereof.

NMR: $^1$H NMR spectra were recorded on a Bruker AC-300 spectrometer at 25° C. with TMS (tetramethylsilane) or residual $^1$H of the given deuterated solvents as internal standards.

MS: Mass spectra (MS) were measured either with ion spray positive or negative (ISP or ISN) method on a Perkin-Elmer SCIEX API 300 or with electron impact method (EI, 70 eV) on a Finnigan MAT SSQ 7000 spectrometer.

HPLC: Analytic was performed on an Agilent 1100 series HPLC with a Macherey-Nagel EC 50/46 Nucleodur 100-3 C18 ec column using a 5 uM filter plate for column protection and a gradient of acetonitrile/H$_2$O (+0.05% formic acid)/(15: 85→98:2 within 5 min, then 1 min at 98:2) at a flow of 2.5 mL/min at 30° C. [injection volume 10 uL, detection at 254 nm].

EXAMPLE A1

(2-Amino-5-nitro-phenyl)-methanol CAS-No. [77242-30-9]

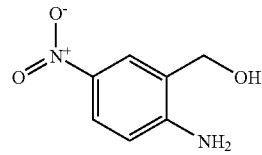

To a solution of commercially available 5-nitroanthranilic acid (28.37 g, 156 mmol; HPLC 1.428 min) in tetrahydrofuran (900 mL) at 0° C. was cannulated a 1 M sol. of borane-tetrahydrofuran complex (500 mL, 500 mmol) [gas evolution!, but almost no exothermic reaction]. The cooling bath was removed and the mixture was stirred at 23° C. for 16 h. Then water (142 mL) was added [strong gas evolution upon addition of the first ca. 30 mL!] followed by 1 M HCl (71 mL) and the resulting yellow mixture was stirred at 23° C. for 1 h. Then a 1 M solution of potassium carbonate in water (35 mL) was added and the entire reaction mixture was concentrated in vacuum on a rotary evaporator to remove all tetrahydrofuran, the resulting yellow precipitate was diluted with ice water (~100 mL), the precipitate was filtered off, washed with ice water and dried in vacuum to give a yellow solid (19.0 g, 73%;

HPLC 0.998 min 100%). $^1$H NMR (300 MHz, DMSO-$d_6$) δ=4.39 (d, $^3$J(H,H)=5.4 Hz, 2H, CH$_2$OH), 5.32 (t, $^3$J(H,H)= 5.4 Hz, 1H, OH), 6.46 (bs, 2H, NH$_2$), 6.65 (d, $^4$J(H,H)=9.0 Hz, 1H, H3), 7.89 (dd, $^{4,5}$J(H,H)=8.7, 2,7 Hz, 1H, H4), 8.05 (d, $^5$J(H,H)=2.7 Hz, H6); MS (ISN) m/e=167.1 [(M−H)$^-$].

EXAMPLE B1

2-(tert-Butyl-dimethyl-silanyloxymethyl)-4-nitro-phenylamine

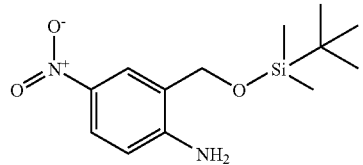

To a mixture of (2-amino-5-nitro-phenyl)-methanol (Example A1) (22.7 g, 135 mmol; HPLC 0.998 min) and imidazole (28.5 g, 419 mmol) in N,N-dimethylformamide (68 mL) at 0° C. was added tert-butyl(chloro)dimethylsilane (33.6 g, 223 mmol) and the mixture was stirred and allowed to reach 23° C. overnight. Poured onto water (plus little NaH$_2$PO$_4$-buffer, pH 4), extracted twice with tert-butylmethyl ether, washed with sat. NaCl-sol., dried over sodium sulfate, filtered off and evaporated to give a brown liquid, which was purified by a silica gel column chromatography with heptane/ethyl acetate 1:4 to give a yellow solid (38.02 g, 99%; HPLC 3.200 min 100%). $^1$H NMR (300 MHz, CDCl$_3$) δ=0.10 (s, 6H, 2×CH$_3$), 0.92 (s, 9H, C(CH$_3$)$_3$), 4.72 (s, 2H, CH$_2$), 5.03 (bs, 2H, NH$_2$), 6.62 (d, $^4$J(H,H)=9.0 Hz, 1H, H3), 7.97 (d, $^5$J(H, H)=2.7 Hz, H6), 8.03 (dd, $^{4,5}$J(H,H)=8.7, 2,7 Hz, 1H, H4); MS (ISN) m/e=281.2 [(M−H)$^-$].

EXAMPLE C1 tert-Butyl-(2-isothiocyanato-5-nitro-benzyloxy)-dimethyl-silane

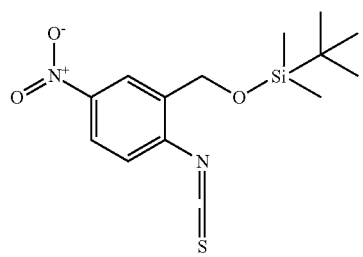

To a mixture of 2-(tert-butyl-dimethyl-silanyloxymethyl)-4-nitro-phenylamine (Example B1) (38.0 g, 135 mmol; HPLC 3.200 min) and solid sodium hydrogen carbonate (56.5 g, 673 mmol) in methylene chloride (650 mL) at 0° C. was added thiophosgene (90%, 12.4 mL, 145 mmol), the cooling bath was removed and the mixture was stirred at 23° C. for 16 h. Poured into ice water (300 mL), separated phases, dried organic layer over sodium sulfate. Removal of the solvent in vacuum left a light yellow solid (40.81 g, 93%; HPLC 4.45 min 100%). [procedure according to Tetr. Lett. 2006, 47, 3953.] $^1$H NMR (300 MHz, CDCl$_3$) δ=0.18 (s, 6H, 2×CH$_3$), 0.99 (s, 9H, C(CH$_3$)$_3$), 4.85 (s, 2H, CH), 7.36 (d, $^4$J(H,H)=9.0 Hz, 1H, H3), 8.14 (dd, $^{4,5}$J(H,H)=8.7, 2,7 Hz, 1H, H4), 8.43 (d, $^5$J(H,H)=2.7 Hz, H6), MS (ISP) m/e=342.2 [(M+NH$_4$)$^+$].

EXAMPLE 1

(2-Methoxy-benzyl)-(6-nitro-4H-benzo[d][1,3]oxazin-2-yl)-amine

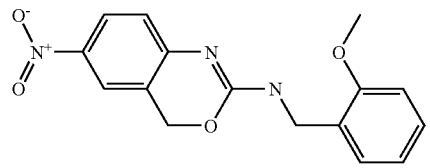

To a stirred solution of tert-butyl-(2-isothiocyanato-5-nitro-benzyloxy)-dimethyl-silane (Example C1) (2.0 g, 6.0 mmol; HPLC: 4.446 min) in acetonitrile (30 mL) at 23° C. was added 2-methoxybenzylamine (0.82 ml, 6.0 mmol; HPLC: 1.773 min) and the mixture was stirred at 23° C. for 15 min (HPLC: 3.487 min 100%). Added tetrabutylammonium fluoride trihydrate (TBAF.3H$_2$O) (1.945 g, 6.0 mmol) and stirred at 23° C. for 1 h (HPLC: 2.188 min 100%). Added 1-(3-dimethylaminopropyl)-3-ethylcarbodiimide hydrochloride (EDC.HCl) (1.772 g, 9.0 mmol) and stirred at 90° C. for 4 to 18 h (HPLC product at 1.667 min, 1-(3-dimethylaminopropyl)-3-ethyl-thiourea at 0.31 min). Cooled to rt, diluted with ethyl acetate and water, added little 1 M NaH$_2$PO$_4$.2H$_2$O solution to achieve pH 4, separated phases, washed organic layer with brine and dried over sodium sulfate. Removal of the solvent in vacuum left a yellow foam, which was purified by flash chromatography on silica gel with n-heptane and ethyl acetate to give the title compound as a yellow foam (1.43 g, 74%), MS (ISP) m/e=288.8 [(M+H)$^+$].

EXAMPLE 2

(R)-N$^2$-Indan-1-yl-4H-benzo[d][1,3]oxazine-2,6-diamine

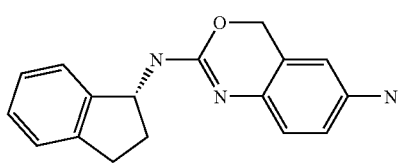

Step A: (R)-Indan-1-yl-(6-nitro-4H-benzo[d][1,3]oxazin-2-yl)-amine: Prepared from tert-butyl-(2-isothiocyanato-5-nitro-benzyloxy)-dimethyl-silane (Example C1) (3.89 g, 12.0 mmol; HPLC: 4.446 min) and commercially available (R)-(−)-1-aminoindane (1.54 mL, 12.0 mmol; HPLC 0.4 min) according to the procedure described for Example 1. Obtained the title compound as a yellow foam (3.45 g, 93%; HPLC 1.954 min), MS (ISN) m/e=308.5 [(M−H)$^-$].

Step B: (R)-N-2-Indan-1-yl-4H-benzo[d][1,3]oxazine-2,6-diamine: To a solution of the above described (R)-indan-1-yl-(6-nitro-4H-benzo[d][1,3]oxazin-2-yl)-amine (3.44 g, 11.1 mmol; HPLC 1.954 min) in tetrahydrofuran (85 mL) at 23° C. were added three Pasteur pipettes of Raney-Nickel (ready to use 10% suspension in water) and the mixture was vigourously stirred under an atmospheric pressure of hydrogen for 23 h. The catalyst was filtered off, washed with tetrahydrofuran, the solvent was removed in vacuum to give the title compound as a light yellow foam (3.19 g, 103%; HPLC 0.642 min 98%), MS (ISP) m/e=280.1 [(M+H)+].

EXAMPLE 3

N-[2-((R)-Indan-1-ylamino)-4H-benzo[d][1,3]oxazin-6-yl]-2-(4-methyl-piperazin-1-yl)-acetamide

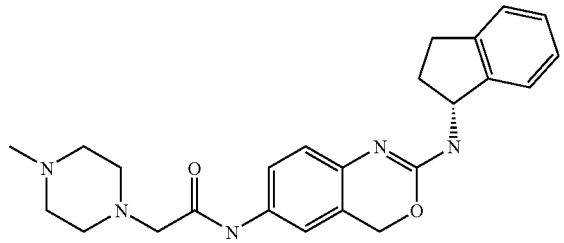

Step A: 2-Chloro-N-[2-((R)-indan-1-ylamino)-4H-benzo[d][1,3]oxazin-6-yl]-acetamide: A mixture of (R)-N-2-indan-1-yl-4H-benzo[d][1,3]oxazine-2,6-diamine (Example 2) (1 g, 3.579 mmol) and sodium carbonate (759 mg, 7.159 mmol) in acetone (40 ml) and was stirred at 23° C. for 10 min, then cooled to −78° C. A of a 0.5 M solution of chloroacetyl chloride (300 ul, 3.759 mmol) in acetone (8 ml) was dropwise added and the mixture was stirred at −78° C. for 30 min. Poured onto water and extracted twice with ethyl acetate, dried the combined organic layers over sodium sulfate, filtered off and evaporated totally to give the crude product which was purified by silica gel column chromatography with ethyl acetate to give the title compound as a light brown foam (1.27 g, 100%), MS (ISP) m/e=356.1 [(M+H)+] and 358 [(M+2+H)+].

Step B: N-[2-((R)-Indan-1-ylamino)-4H-benzo[d][1,3]oxazin-6-yl]-2-(4-methyl-piperazin-1-yl)-acetamide: A mixture of the above described 2-chloro-N-[2-((R)-indan-1-ylamino)-4H-benzo[d][1,3]oxazin-6-yl]-acetamide (800 mg, 2.248 mmol) and 1-methylpiperazine (5 ml, 45 mmol) was stirred at 23° C. for 18 h. Diluted with ethyl acetate, washed with sat. sodium hydrogen carbonate-solution, dried the organic layer over sodium sulfate. Filtration and removal of the solvent in vacuum left a crude product which was purified by silica gel column chromatography with ethyl acetate to ethyl acetate +10% methanol-ammonium hydroxide (10:1) and trituration with diethyl ether to give the title compound as a white foam (320 mg, 34%), MS (ISP) m/e=420.2 [(M+H)+].

EXAMPLE 4

N²-(2-Methoxy-benzyl)-4H-benzo[d][1,3]oxazine-2,6-diamine

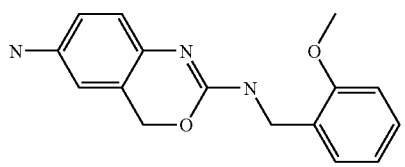

Prepared from (2-methoxy-benzyl)-(6-nitro-4H-benzo[d][1,3]oxazin-2-yl)-amine (Example 1) (1.43 g, 5 mmol; HPLC 1.667 min) according to the procedure described for Example 2 step B. Obtained the title compound as a yellow foam (1.30 g, 100%; HPLC 0.650 min), MS (ISP) m/e=284.1 [(M+H)+].

EXAMPLE 5 rac-(4-Methoxy-2,3-dihydro-benzofuran-3-yl)-(6-nitro-4H-benzo[d][1,3]oxazin-2-yl)-amine

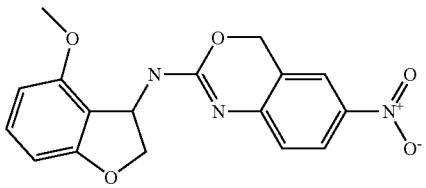

Step A: 4-Methoxy-benzofuran-3-one oxime: A mixture of 4-methoxy-benzofuran-3-one (CAS 7169-35-9) (30 g, 183 mmol; HPLC 1.241 min), sodium acetate (30.9 g, 375 mmol) and hydroxylamine hydrochloride (5.14 g, 57 mmol) in ethanol (310 ml) was refluxed for 4 h. Cooled to 23° C., filtered the precipitate off, washed with aqueous ethanol and dried in high vacuum to give the title compound as a light red solid (27.74 g, 88%; HPLC 1.448 min); MS (ISP) m/e=180.2 [(M+H)+].

Step B: rac-4-Methoxy-2,3-dihydro-benzofuran-3-ylamine: A mixture of the above described 4-methoxy-benzofuran-3-one oxime (27.7 g, 155 mmol; HPLC 1.448 min) and Raney-Nickel (13.85 g) in tetrahydrofuran (700 mL) and methanol (700 mL) was hydrogenated at 100 bar hydrogen-pressure at 100° C. for 22 h. Filtered the catalyst off, washed with methanol and tetrahydrofuran, all volatiles very removed in vacuum to give the title compound as a brown oil (24.7 g, 98%, HPLC 0.4 min), MS (ISP) m/e=166.2 [(M+H)+].

Step C: rac-(4-Methoxy-2,3-dihydro-benzofuran-3-yl)-(6-nitro-4H-[d][1,3]oxazin-2-yl)-amine: Prepared from tert-butyl-(2-isothiocyanato-5-nitro-benzyloxy)-dimethyl-silane (Example C1) (4.24 g, 13.1 mmol; HPLC: 4.446 min) and the above described rac-4-methoxy-2,3-dihydro-benzofuran-3-ylamine (2.16 g, 13.1 mmol; HPLC 0.4 min) according to the procedure described for Example 1. Obtained the title compound as a yellow foam (3.94 g, 88%; HPLC 1.999 min), MS (ISP) m/e=342.1 [(M+H)+].

EXAMPLE 6 rac-N²-(4-Methoxy-2,3-dihydro-benzofuran-3-yl)-4H-benzo[d][1,3]oxazine-2,6-diamine

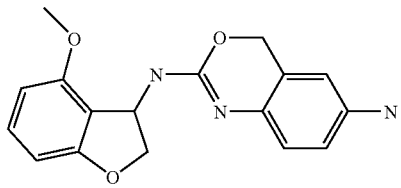

Prepared from rac-(4-methoxy-2,3-dihydro-benzofuran-3-yl)-(6-nitro-4H-benzo[d][1,3]oxazin-2-yl)-amine (Example 5) (3.93 g, 11.5 mmol; HPLC 1.999 min) according to the procedure described for Example 2 step B. Obtained the title compound as a light yellow foam (3.77 g, 106%; HPLC 0.580 min, 90% purity), MS (ISP) m/e=312.2 [(M+H)$^+$].

EXAMPLE 7

Cyclopropanecarboxylic acid [2-(2-methoxy-benzylamino)-4H-benzo[d][1,3]oxazin-6-yl]-amide

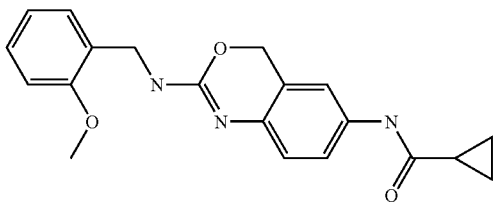

To a vigorously stirred solution of N$^2$-(2-methoxy-benzyl)-4H-benzo[d][1,3]oxazine-2,6-diamine (Example 4) (128 mg, 0.45 mmol; HPLC 0.41 min) in ethyl acetate (2 ml) and sat. sodium hydrogen carbonate-sol. (1.2 ml) at 23° C. was dropwise added cyclopropanecarbonyl chloride (50 ul, 0.54 mmol) and the mixture was stirred at 23° C. for 20 min. Diluted with ethyl acetate and water, separated phases, washed organic layer with brine and dried over sodium sulfate. Removal of the solvent in vacuum left an off-white solid which was purified by silica gel column chromatography with heptane/ethyl acetate 1:1 to 0:1 followed by trituration with diethyl ether to give the title compound as a white solid (95 mg, 55%, HPLC 0.998 min 100%), MS (ISP) m/e=352.3 [(M+H)$^+$].

EXAMPLE 8 rac-2-Chloro-N-[2-(4-methoxy-2,3-dihydro-benzofuran-3-ylamino)-4H-benzo[d][1,3]oxazin-6-yl]-acetamide

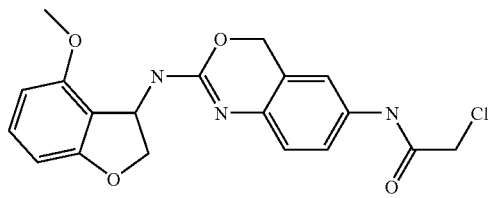

Prepared from rac-N$^2$-(4-methoxy-2,3-dihydro-benzofuran-3-yl)-4H-benzo[d][1,3]oxazine-2,6-diamine (Example 6) (320 mg, 1.03 mmol) and chloroacetyl chloride (85.8 ul, 1.08 mmol) according to the procedure described for Example 3 step A. Obtained the title compound as an off-white solid (380 mg, 95%), MS (ISP) m/e=388.2 [(M+H)$^+$] and 390 [(M+2+H)$^+$].

EXAMPLE 9 rac-N-[2-(4-Methoxy-2,3-dihydro-benzofuran-3-ylamino)-4H-benzo[d][1,3]oxazin-6-yl]-2-(4-methyl-piperazin-1-yl)-acetamide

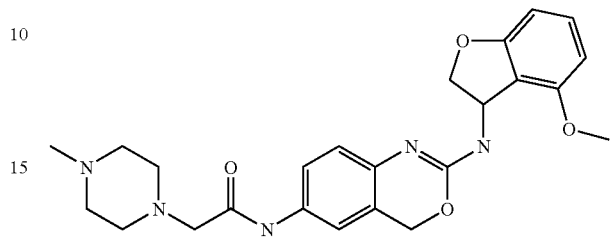

Prepared from rac-2-chloro-N-[2-(4-methoxy-2,3-dihydro-benzofuran-3-ylamino)-4H-benzo[d][1,3]oxazin-6-yl]-acetamide (Example 8) (370 mg, 0.95 mmol) and 1-methylpiperazine (2.12 ml, 19.08 mmol) according to the procedure described for Example 3 step B. Obtained the title compound as a white foam (340 mg, 79%), MS (ISP) m/e=452.3 [(M+H)$^+$].

EXAMPLE 10 rac-N$^2$-(7-Methoxy-indan-1-yl)-4H-benzo[d][1,3]oxazine-2,6-diamine

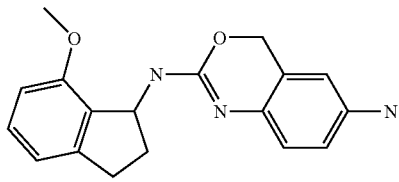

Step A: rac-7-Methoxy-indan-1-ylamine: A mixture of 7-methoxy-indan-1-one oxime (CAS 908108-58-7, (E)-oxime 179899-16-2) (22.3 g, 126 mmol)) and Raney-Nickel (11.26 g) in tetrahydrofuran (570 mL) and methanol (570 mL) was hydrogenated at 100 bar hydrogen-pressure at 60° C. for 22 h. Filtered the catalyst off, washed with methanol and tetrahydrofuran, all volatiles were removed in vacuum to give the title compound as a brown oil (19.95 g, 97%, HPLC 0.4 min), MS (ISP) m/e=164.2 [(M+H)$^+$].

Step B: rac-(7-Methoxy-indan-1-yl)-(6-nitro-4H-benzo[d][1,3]oxazin-2-yl)-amine: Prepared from tert-butyl-(2-isothiocyanato-5-nitro-benzyloxy)-dimethyl-silane (Example C1) (3.89 g, 12.0 mmol; HPLC: 4.446 min) and the above described rac-7-methoxy-indan-1-ylamine (1.96 g, 12.0 mmol; HPLC 0.4 min) according to the procedure described for Example 1. Obtained the title compound as a yellow solid (2.99 g, 73%; HPLC 1.683 min), MS (ISP) m/e=340.1 [(M+H)$^+$].

Step C: rac-N$^2$-(7-Methoxy-indan-1-yl)-4H-benzo[d][1,3]oxazine-2,6-diamine: Prepared from the above described rac-(7-methoxy-indan-1-yl)-(6-nitro-4H-benzo[d][1,3]oxazin-2-yl)-amine (2.97 g, 8.75 mmol; HPLC 1.683 min) according to the procedure described for Example 2 step B. Obtained the

EXAMPLE 11 rac-$N^2$-(5-Fluoro-indan-1-yl)-4H-benzo[d][1,3]oxazine-2,6-diamine

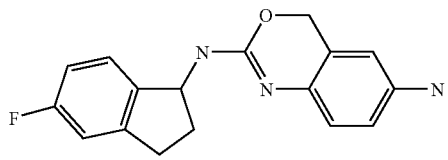

Step A: rac-(5-Fluoro-indan-1-yl)-(6-nitro-4H-benzo[d][1,3]oxazin-2-yl)-amine: Prepared from tert-butyl-(2-isothiocyanato-5-nitro-benzyloxy)-dimethyl-silane (Example C1) (1.22 g, 3.76 mmol; HPLC: 4.446 min) and rac-5-fluoro-indan-1-ylamine (CAS 148960-33-2) (568 mg, 3.76 mmol; HPLC 0.4 min) according to the procedure described for Example 1. Obtained the title compound as a yellow solid (0.93 g, 90%), MS (ISP) m/e=328.2 [(M+H)$^+$].

Step B: rac-$N^2$-(5-Fluoro-indan-1-yl)-4H-benzo[d][1,3]oxazine-2,6-diamine: Prepared from the above described rac-(5-fluoro-indan-1-yl)-(6-nitro-4H-benzo[d][1,3]oxazin-2-yl)-amine (930 mg, 2.84 mmol) according to the procedure described for Example 2 step B. Obtained the title compound as a light yellow foam (0.84 g, 99%), MS (ISP) m/e=298.2 [(M+H)$^+$].

EXAMPLE 12 rac-2-(4-Isopropyl-piperazin-1-yl)-N-[2-(4-methoxy-2,3-dihydro-benzofuran-3-ylamino)-4H-benzo[d][1,3]oxazin-6-yl]-acetamide

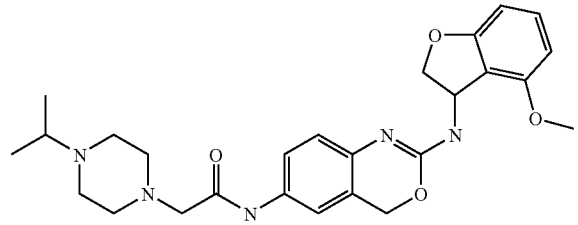

Prepared from rac-2-chloro-N-[2-(4-methoxy-2,3-dihydro-benzofuran-3-ylamino)-4H-benzo[d][1,3]oxazin-6-yl]-acetamide (Example 8) (50 mg, 0.129 mmol) and 1-(isopropyl)piperazine (330 mg, 2.578 mmol) according to the procedure described for Example 3 step B (here the reaction was sonicated for 2 min, which already lead to complete conversion). Obtained the title compound as a white solid (45 mg, 73%), MS (ISP) m/e=480.3 [(M+H)$^+$].

EXAMPLE 13 rac-N-[2-(4-Methoxy-2,3-dihydro-benzofuran-3-ylamino)-4H-benzo[d][1,3]oxazin-6-yl]-2-morpholin-4-yl-acetamide

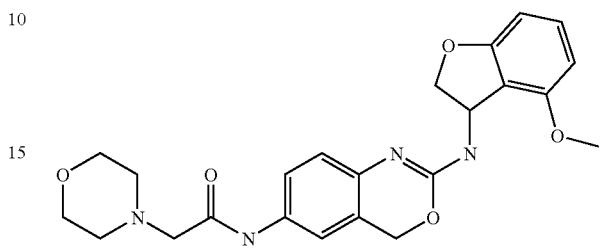

Prepared from rac-2-chloro-N-[2-(4-methoxy-2,3-dihydro-benzofuran-3-ylamino)-4H-benzo[d][1,3]oxazin-6-yl]-acetamide (Example 8) (50 mg, 0.129 mmol) and morpholine (225 ul, 2.578 mmol) according to the procedure described for Example 3 step B (here the reaction was sonicated for 2 min, which already lead to complete conversion). Obtained the title compound as a white solid (20 mg, 35%), MS (ISP) m/e=439.3 [(M+H)$^+$].

EXAMPLE 14 rac-1-(1-Isopropyl-piperidin-4-yl)-3-[2-(4-methoxy-2,3-dihydro-benzofuran-3-ylamino)-4H-benzo[d][1,3]oxazin-6-yl]-urea

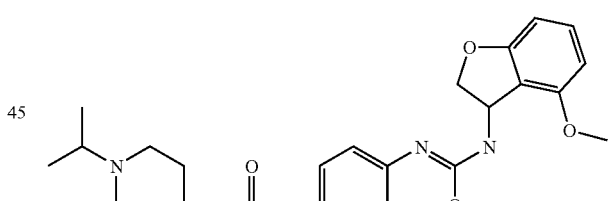

To a solution of rac-$N^2$-(7-methoxy-indan-1-yl)-4H-benzo[d][1,3]oxazine-2,6-diamine (Example 10) (156 mg, 0.5 mmol; HPLC 0.595 min) and pyridine (40 uL, 0.5 mmol) in dichloromethane (2 mL) at 0° C. was added 4-nitrophenyl chloroformate (101 mg, 0.5 mmol) and the mixture was stirred at 23° C. for 1.5 h resulting in a yellow suspension (HPLC 1.689 min). Added N-isopropyl-4-aminopiperidine (71.1 mg, 0.50 mmol) and diisopropylethyl amine (300 uL, 1.75 mmol) and dichloromethane (2 mL) and the clear solution was stirred at 23° C. for 18 h, then directly purified by flash chromatography on silica gel with dichloromethane/methanol/Et$_3$N to give the title compound as a light yellow oil (183 mg, 76%, HPLC 0.523 min), MS: m/e=480.4 (M+H$^+$).

EXAMPLE 15 rac-1-(1-Isopropyl-piperidin-4-yl)-3-[2-(4-methoxy-2,3-dihydro-benzofuran-3-ylamino)-4H-benzo[d][1,3]oxazin-6-yl]-1-methyl-urea

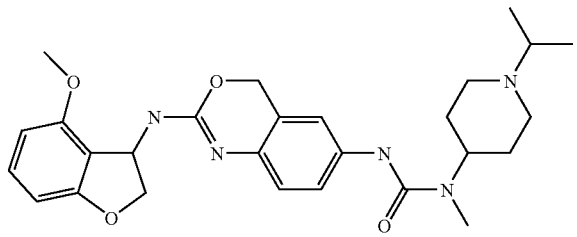

Prepared from rac-$N^2$-(7-methoxy-indan-1-yl)-4H-benzo[d][1,3]oxazine-2,6-diamine (Example 10) (156 mg, 0.5 mmol; HPLC 0.595 min), 4-nitrophenyl chloroformate (101 mg, 0.5 mmol) and (1-isopropyl-piperidin-4-yl)-methyl-amine dihydrochloride (CAS of free base 503126-34-9) (115 mg, 0.50 mmol) and diisopropylethyl amine (300 ul, 1.75 mmol) according to the procedure described for Example 14. Obtained the title compound as an off-white solid (28 mg, 11%, HPLC 0.522 min), MS (ISP) m/e=494.4 [(M+H)$^+$].

EXAMPLE 16 rac-1-Isopropyl-3-[2-(4-methoxy-2,3-dihydro-benzofuran-3-ylamino)-4H-benzo[d][1,3]oxazin-6-yl]-urea

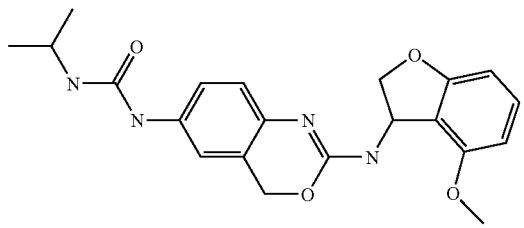

To a solution of rac-$N^2$-(7-methoxy-indan-1-yl)-4H-benzo[d][1,3]oxazine-2,6-diamine (Example 10) (156 mg, 0.5 mmol; HPLC 0.595 min) in acetonitrile (5 ml) at 23° C. was added isopropyl isocyanate (49 ul, 0.5 mmol) and the mixture was stirred at 23° C. for 18 h followed by microwave irradiation at 120° C. for 60 min. The reaction mixture was completely evaporated and triturated twice with diethyl ether to give the title compound as an off-white solid (50 mg, 25%, HPLC 1.247 min), MS (ISP) m/e=397.2 [(M+H)$^+$].

EXAMPLE 17 rac-2-Methoxy-N-[2-(4-methoxy-2,3-dihydro-benzofuran-3-ylamino)-4H-benzo[d][1,3]oxazin-6-yl]-acetamide

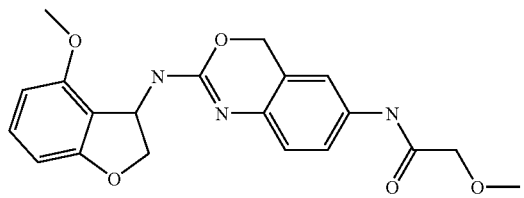

To a solution of rac-$N^2$-(7-methoxy-indan-1-yl)-4H-benzo[d][1,3]oxazine-2,6-diamine (Example 10) (100 mg, 0.321 mmol) in ethyl acetate (5 ml) and sat. sodium hydrogen carbonate-sol. at 0° C. was added methoxyacetyl chloride (35 ul, 0.385 mmol) and the mixture was stirred at 23° C. for 16 h. Diluted with ethyl acetate, washed with water, dried the organic layer over sodium sulfate. After filtration, the solvent was removed in vacuum and the crude product was triturated with diethyl ether to give the title compound as a white solid (90 mg, 73%), MS (ISP) m/e=384.2 [(M+H)$^+$].

EXAMPLE 18

Cyclopropanecarboxylic acid [2-((R)-indan-1-ylamino)-4H-benzo[d][1,3]oxazin-6-yl]-amide

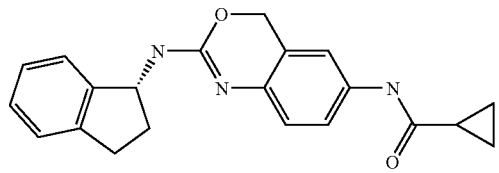

Prepared from (R)-N-2-indan-1-yl-4H-benzo[d][1,3]oxazine-2,6-diamine (Example 2) (300 mg, 1.074 mmol) and cyclopropylcarbonyl chloride (109 ul, 1.128 mmol) according to the procedure described for Example 3 step A. Obtained the title compound as a white solid (300 mg, 80%), MS (ISP) m/e=348.3 [(M+H)$^+$].

EXAMPLE 19

N-[2-((R)-Indan-1-ylamino)-4H-benzo[d][1,3]oxazin-6-yl]-2-methoxy-acetamide

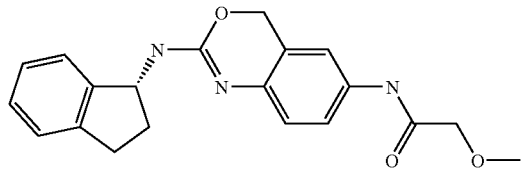

Prepared from (R)-N-2-indan-1-yl-4H-benzo[d][1,3]oxazine-2,6-diamine (Example 2) (100 mg, 0.358 mmol) and methoxyacetyl chloride (36 ul, 0.394 mmol) according to the procedure described for Example 17. Obtained the title compound as a white solid (30 mg, 24%), MS (ISP) m/e=352.2 [(M+H)$^+$].

EXAMPLE 20 rac-Cyclopropanecarboxylic acid [2-(5-fluoro-indan-1-ylamino)-4H-benzo[d][1,3]oxazin-6-yl]-amide

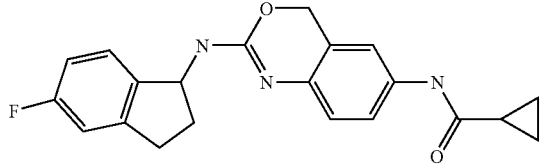

Prepared from rac-$N^2$-(5-fluoro-indan-1-yl)-4H-benzo[d][1,3]oxazine-2,6-diamine (Example 11) (100 mg, 0.336 mmol) and cyclopropylcarbonyl chloride (34 ul, 0.370 mmol) according to the procedure described for Example 17. Obtained the title compound as a white solid (70 mg, 57%), MS (ISP) m/e=366.1 [(M+H)$^+$].

EXAMPLE 21 rac-N-[2-(5-Fluoro-indan-1-ylamino)-4H-benzo[d]
[1,3]oxazin-6-yl]-2-methoxy-acetamide

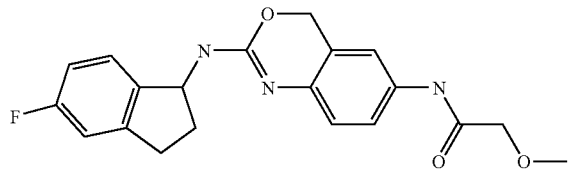

Prepared from rac-N²-(5-fluoro-indan-1-yl)-4H-benzo[d][1,3]oxazine-2,6-diamine (Example 11) (100 mg, 0.336 mmol) and methoxyacetyl chloride (34 ul, 0.370 mmol) according to the procedure described for Example 17. Obtained the title compound as a white solid (50 mg, 40%), MS (ISP) m/e=370.2 [(M+H)⁺].

EXAMPLE 22 rac-N²-(8-Methoxy-1,2,3,4-tetrahydro-naphthalen-1-yl)-4H-benzo[d][1,3]oxazine-2,6-diamine

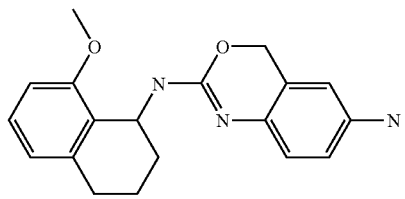

Step A: rac-(8-Methoxy-1,2,3,4-tetrahydro-naphthalen-1-yl)-(6-nitro-4H-benzo[d][1,3]oxazin-2-yl)-amine: Prepared from tert-butyl-(2-isothiocyanato-5-nitro-benzyloxy)-dimethyl-silane (Example C1) (2.76 g, 8.5 mmol; HPLC: 4.446 min) and rac-8-methoxy-1,2,3,4-tetrahydro-naphthalen-1-ylamine (CAS 535935-61-6) (1.51 g, 8.5 mmol; HPLC 0.403 min) according to the procedure described for Example 1. Obtained the title compound as a yellow solid (2.38 g, 79%, HPLC 1.805 min), MS (ISP) m/e=354.2 [(M+H)⁺].
Step B: rac-N²-(8-Methoxy-1,2,3,4-tetrahydro-naphthalen-1-yl)-4H-benzo[d][1,3]oxazine-2,6-diamine: Prepared from the above described rac-(8-methoxy-1,2,3,4-tetrahydro-naphthalen-1-yl)-(6-nitro-4H-benzo[d][1,3]oxazin-2-yl)-amine (2.30 g, 7.0 mmol, HPLC 1.805 min) according to the procedure described for Example 2 step B. Obtained the title compound as a yellow foam (2.33 g, 100%, HPLC 1.090 min 90%), MS (ISP) m/e=324.3 [(M+H)⁺].

EXAMPLE 23 rac-Cyclopropanecarboxylic acid [2-(8-methoxy-1,2,3,4-tetrahydro-naphthalen-1-ylamino)-4H-benzo[d][1,3]oxazin-6-yl]-amide

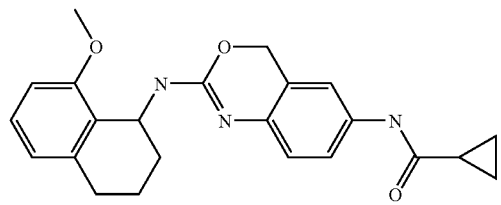

Prepared from rac-N²-(8-methoxy-1,2,3,4-tetrahydro-naphthalen-1-yl)-4H-benzo[d][1,3]oxazine-2,6-diamine (Example 22) (162 mg, 0.50 mmol, HPLC 1.090 min) and cyclopropanecarbonyl chloride (53 ul, 0.55 mmol) according to the procedure described for Example 17. Obtained the title compound as an off-white solid (190 mg, 90%, HPLC 1.479 min 93%), MS (ISP) m/e=392.2 [(M+H)⁺].

EXAMPLE 24 rac-2-Methoxy-N-[2-(7-methoxy-indan-1-ylamino)-4H-benzo[d][1,3]oxazin-6-yl]-acetamide

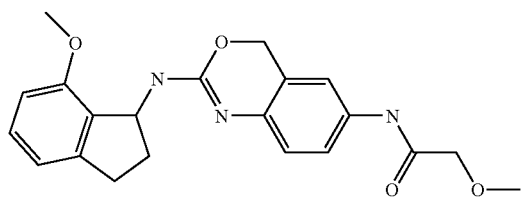

Prepared from rac-N²-(7-methoxy-indan-1-yl)-4H-benzo[d][1,3]oxazine-2,6-diamine (Example 10) (100 mg, 0.323 mmol) and methoxyacetyl chloride (32 ul, 0.356 mmol) according to the procedure described for Example 17. Obtained the title compound as a white solid (75 mg, 61%), MS (ISP) m/e=382.2 [(M+H)⁺].

EXAMPLE 25 rac-Cyclopropanecarboxylic acid [2-(7-methoxy-indan-1-ylamino)-4H-benzo[d][1,3]oxazin-6-yl]-amide

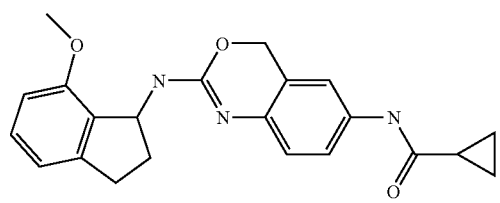

Prepared from rac-N²-(7-methoxy-indan-1-yl)-4H-benzo[d][1,3]oxazine-2,6-diamine (Example 10) (100 mg, 0.323 mmol) and cyclopropancarbonyl chloride (32 ul, 0.356 mmol) according to the procedure described for Example 17. Obtained the title compound as a white solid (90 mg, 74%), MS (ISP) m/e=378.3 [(M+H)⁺].

EXAMPLE 26

N-[2-(2-Methoxy-benzylamino)-4H-benzo[d][1,3]oxazin-6-yl]-2-(4-methyl-piperazin-1-yl)-acetamide

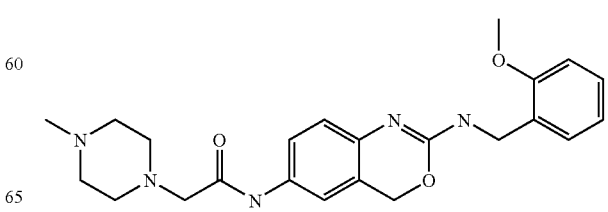

Step A: 2-Chloro-N-[2-(2-methoxy-benzylamino)-4H-benzo[d][1,3]oxazin-6-yl]-acetamide: Prepared from $N^2$-(2-methoxy-benzyl)-4H-benzo[d][1,3]oxazine-2,6-diamine (Example 4) (1.26 g, 4.45 mmol) and chloroacetyl chloride (0.39 ml, 4.89 mmol) according to the procedure described for Example 17. Obtained the title compound as a white solid (842 mg, 42%, HPLC 0.889 min 81%), MS (ISP) m/e=360.3 [(M+H)$^+$] and 362.1 [(M+2+H)$^+$].

Step B: N-[2-(2-Methoxy-benzylamino)-4H-benzo[d][1,3]oxazin-6-yl]-2-(4-methyl-piperazin-1-yl)-acetamide: Prepared from the above described 2-chloro-N-[2-(2-methoxy-benzylamino)-4H-benzo[d][1,3]oxazin-6-yl]-acetamide (50 mg, 0.129 mmol, HPLC 0.889 min 81%) and N-methylpiperazine (900 ul, 8 mmol) according to the procedure described for Example 3 step B. Obtained the title compound as a white foam (123 mg, 73%, HPLC 0.531 min 100%), MS (ISP) m/e=424.4 [(M+H)$^+$].

EXAMPLE 27

N,N-(Dimethyl)-N'-{2-((R)-indan-1-ylamino)-4H-benzo[d][1,3]oxazin-6-yl}-sulfamide

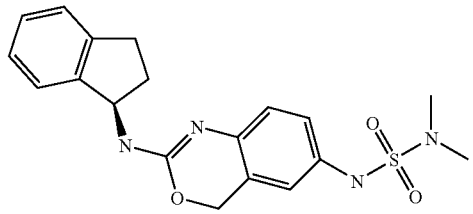

To a solution of (R)-N-2-indan-1-yl-4H-benzo[d][1,3]oxazine-2,6-diamine (Example 2) (140 mg, 0.501 mmol), diisopropylethyl amine (172 ul, 1.002 mmol) and 4-DMAP (ca. 10 mg) in acetonitrile (5 ml) at 23° C. was added dimethylsulfamoyl chloride (59.1 ul, 0.551 mmol) and the mixture was stirred at 23° C. for 24 h. Diluted with ethyl acetate, washed with sat. sodium hydrogen carbonate-sol., dried over sodium sulfate. After filtration, the solvent was removed in vacuum and the obtained crude product was purified by silica gel column chromatography with ethyl acetate to give the title compound as a light yellow foam (90 mg, 46%), MS (ISP) m/e=387.2 [(M+H)$^+$].

EXAMPLE 28

2-[4-(2-Hydroxy-ethyl)-piperazin-1-yl]-N-[2-(2-methoxy-benzylamino)-4H-benzo[d][1,3]oxazin-6-yl]-acetamide

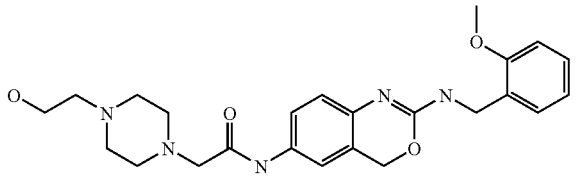

Prepared from 2-chloro-N-[2-(2-methoxy-benzylamino)-4H-benzo[d][1,3]oxazin-6-yl]-acetamide (Example 26 step A) (50 mg, 0.129 mmol, HPLC 0.889 min 81%) and 1-(2-hydroxyethyl)piperazine (1 ml, 8 mmol) in acetonitrile (3 ml) according to the procedure described for Example 3 step B. Obtained the title compound as a white foam (143 mg, 79%, HPLC 0.379 min), MS (ISP) m/e=454.3 [(M+H)$^+$].

EXAMPLE 29

2-(4-Isopropyl-piperazin-1-yl)-N-[2-(2-methoxy-benzylamino)-4H-benzo[d][1,3]oxazin-6-yl]-acetamide

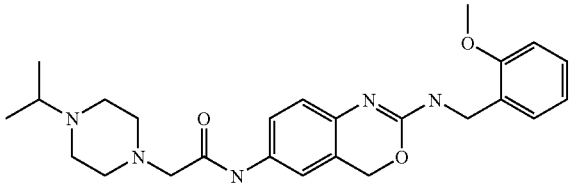

Prepared from 2-chloro-N-[2-(2-methoxy-benzylamino)-4H-benzo[d][1,3]oxazin-6-yl]-acetamide (Example 26 step A) (50 mg, 0.129 mmol, HPLC 0.889 min 81%) and N-isopropylpiperazine (1 ml, 8 mmol) according to the procedure described for Example 3 step B. Obtained the title compound as a white foam (150 mg, 72%, HPLC 0.492 min 87%), MS (ISP) m/e=452.3 [(M+H)$^+$].

EXAMPLE 30

Piperidine-1-sulfonic acid [2-((R)-indan-1-ylamino)-4H-benzo[d][1,3]oxazin-6-yl]-amide

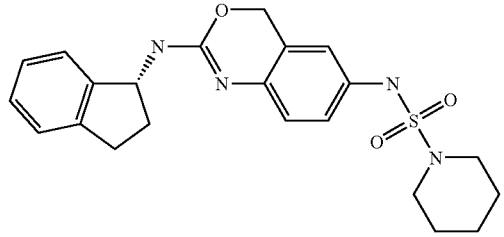

Prepared from (R)-N-2-indan-1-yl-4H-benzo[d][1,3]oxazine-2,6-diamine (Example 2) (100 mg, 0.358 mmol, HPLC 0.642 min) and piperidine-1-sulfonyl chloride (72 mg, 0.394 mmol) according to the procedure described for Example 27. Obtained the title compound as an off-white solid (70 mg, 46%, HPLC 1.613 min), MS (ISP) m/e=427.2 [(M+H)$^+$].

EXAMPLE 31

Morpholine-4-sulfonic acid [2-((R)-indan-1-ylamino)-4H-benzo[d][1,3]oxazin-6-yl]-amide

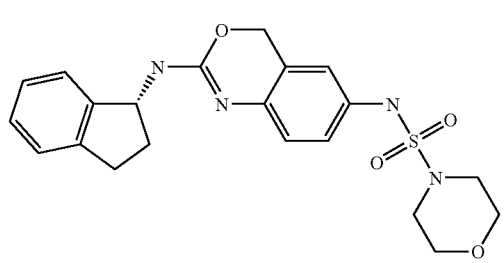

Prepared from (R)-N-2-indan-1-yl-4H-benzo[d][1,3]oxazine-2,6-diamine (Example 2) (100 mg, 0.358 mmol, HPLC 0.642 min) and morpholin-4-sulfonyl chloride (73 mg, 0.394 mmol) according to the procedure described for Example 27. Obtained the title compound as a light brown solid (85 mg, 55%, HPLC 1.342 min), MS (ISP) m/e=429.3 [(M+H)+].

EXAMPLE 32

(6-Bromo-4H-benzo[d][1,3]oxazin-2-yl)-(R)-indan-1-yl-amine

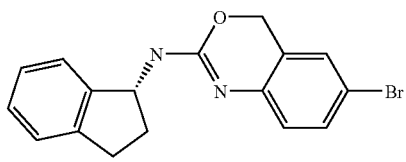

Step A: 4-Bromo-2-(tert-butyl-dimethyl-silanyloxymethyl)-phenylamine The title compound (30.2 g, 64%), colorless liquid, MS (ISP): m/e=317.8.2 (M+H+), was prepared according to the general method of Example B1 from commercially available (2-amino-5-bromophenyl)methanol [CAS-No. 20712-12-3] (30.2 g, 0.15 mol).

Step B: (5-Bromo-2-isothiocyanato-benzyloxy)-tert-butyl-dimethyl-silane The title compound (33.7 g, 98%), light yellow liquid, MS (EI): m/e=302.0 (M-tert-butyl+), was prepared according to the general method of Example C1 from 4-bromo-2-(tert-butyl-dimethyl-silanyloxymethyl)-phenylamine (30.2 g, 95.5 mmol).

Step C: (6-Bromo-4H-benzo[d][1,3]oxazin-2-yl)-(R)-indan-1-yl-amine The title compound (1.21 g, 63%), light brown solid, m.p. 123° C., MS (ISP): m/e=344.9 (M+H+), was prepared according to the general method of Example 1 from (5-bromo-2-isothiocyanato-benzyloxy)-tert-butyl-dimethyl-silane (1.99 g, 5.55 mmol) and commercially available (R)-indan-1-yl-amine (0.74 g, 5.55 mmol).

EXAMPLE 33

(R)-N²-(1,2,3,4-Tetrahydro-naphthalen-1-yl)-4H-benzo[d][1,3]oxazine-2,6-diamine

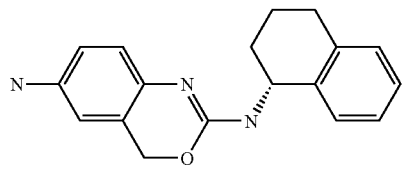

Step A: (6-Nitro-4H-benzo[d][1,3]oxazin-2-yl)-(R)-1,2,3,4-tetrahydro-naphthalen-1-yl-amine: Prepared from tert-butyl-(2-isothiocyanato-5-nitro-benzyloxy)-dimethyl-silane (Example C1) (3.894 g, 12.0 mmol; HPLC: 4.446 min) and (R)-1-aminotetralin (CAS 21966-60-9) (1.767 g, 12.0 mmol; HPLC: 0.390 min) according to the procedure described for Example 1. Obtained the title compound as a yellow foam (3.11 g, 80%, HPLC 2.211 min), MS (ISP) m/e=324.2 [(M+H)+].

Step B: (R)-N²-(1,2,3,4-Tetrahydro-naphthalen-1-yl)-4H-benzo[d][1,3]oxazine-2,6-diamine: Prepared from the above described (6-nitro-4H-benzo[d][1,3]oxazin-2-yl)-(R)-1,2,3,4-tetrahydro-naphthalen-1-yl-amine (3.04 g, 9.0 mmol, HPLC 2.211 min) according to the procedure described for Example 2 step B. Obtained the title compound as a yellow foam (3.01 g, 100%, HPLC 0.946 min 92%), MS (ISP) m/e=294.2 [(M+H)+].

EXAMPLE 34 rac-N²-(6-Fluoro-2,3-dihydro-benzofuran-3-yl)-4H-benzo[d][1,3]oxazine-2,6-diamine

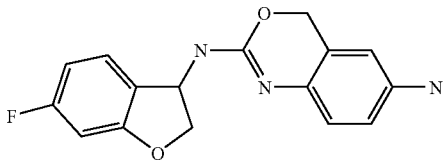

Step A: 6-Fluoro-benzofuran-3-one oxime: A mixture of 6-fluoro-benzofuran-3-one (CAS 351528-80-8) (5.93 g, 39 mmol), sodium acetate (6.587 g, 80 mmol) and hydroxylamine hydrochloride (5.553 g, 80 mmol) in ethanol (70 ml) was refluxed for 4 h. Cooled to 23° C., filtered the precipitate off, washed with aqueous ethanol and dried in high vacuum to give the title compound as a white solid (5.19 g, 80%, HPLC 1.489 min); MS (ISN) m/e=168.1 [(M-H)−].

Step B: rac-6-Fluoro-2,3-dihydro-benzofuran-3-ylamine: A mixture of the above described 6-fluoro-benzofuran-3-one oxime (5.38 g, 32 mmol; HPLC 1.489 min) and Raney-Nickel (2.4 g) in tetrahydrofuran (125 mL) and methanol (125 mL) was hydrogenated at 100 bar hydrogen-pressure at 50° C. for 18 h. Filtered the catalyst off, washed with methanol and tetrahydrofuran, all volatiles very removed in vacuum to give the crude product which was purified by Si—NH₂ column chromatography with n-heptane/ethyl acetate to give the title compound as a light brown liquid (1.65 g, 34%, HPLC 0.367 min 100%), MS (ISP) m/e=154.0 [(M+H)+].

Step C: rac-(4-Methoxy-2,3-dihydro-benzofuran-3-yl)-(6-nitro-4H-benzo[d][1,3]oxazin-2-yl)-amine: Prepared from tert-butyl-(2-isothiocyanato-5-nitro-benzyloxy)-dimethyl-silane (Example C1) (1.947 g, 6.0 mmol; HPLC: 4.446 min) and the above described rac-6-fluoro-2,3-dihydro-benzofuran-3-ylamine (0.919 g, 6.0 mmol; HPLC 0.367 min) according to the procedure described for Example 1. Obtained the title compound as a yellow solid (1.52 g, 77%; HPLC 2.319 min), MS (ISP) m/e=330.0 [(M+H)+].

Step D: rac-N²-(6-Fluoro-2,3-dihydro-benzofuran-3-yl)-4H-benzo[d][1,3]oxazine-2,6-diamine: Prepared from the above described rac-(4-methoxy-2,3-dihydro-benzofuran-3-yl)-(6-nitro-4H-benzo[d][1,3]oxazin-2-yl)-amine (1.5 g, 9.0 mmol; HPLC 2.319 min) according to the procedure described for Example 2 step B. Obtained the title compound as a yellow solid (1.53 g, 100%; HPLC 0.641 min 89%), MS (ISP) m/e=300.2 [(M+H)+].

EXAMPLE 35

N²-(R)-Indan-1-yl-N⁶-(6-trifluoromethyl-pyridin-2-yl)-4H-benzo[d][1,3]oxazine-2,6-diamine

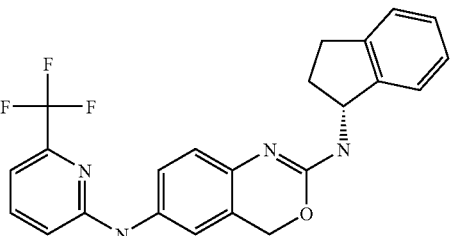

A mixture of (6-bromo-4H-benzo[d][1,3]oxazin-2-yl)-(R)-indan-1-yl-amine (Example 32) (172 mg, 0.5 mmol), commercially available 2-amino-6-trifluoromethyl-pyridine (162 mg, 1.0 mmol), tert-Bu-XPhos (34 mg, 0.08 mmol), Pd$_2$dba$_3$ (18 mg, 0.02 mmol), sodium tert.-butylate (53 mg, 0.55 mmol), tert-butanol (0.5 ml) and dioxane (3 ml) was heated in a sealed tube at 120° C. for 16 h. The reaction mixture was poured into water (15 ml) and extracted with ethyl acetate (2×30 ml). The combined organic layers were washed with water (20 ml) and brine (20 ml), dried (magnesium sulfate) and evaporated. Further purification of the crude product by flash chromatography on silica gel (ethyl acetate/heptane) yielded the title compound (127 mg, 60%) as light brown foam. MS (ISP): m/e=425.2 (M+H$^+$).

EXAMPLE 37

N-[2-((R)-Indan-1-ylamino)-4H-benzo[d][1,3]oxazin-6-yl]-2-morpholin-4-yl-acetamide

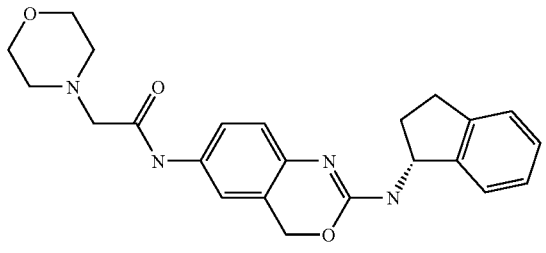

Prepared from 2-chloro-N-[2-((R)-indan-1-ylamino)-4H-benzo[d][1,3]oxazin-6-yl]-acetamide (Example 3 step A) (355 mg, 0.998 mmol) and morpholine (1.3 ml, 15 mmol) according to the procedure described for Example 3 step B. Obtained the title compound as a white foam (200 mg, 49%), MS (ISP) m/e=407.3 [(M+H)$^+$].

EXAMPLE 38

2-(4-Methyl-piperazin-1-yl)-N-{2-[(R)-(1,2,3,4-tetrahydro-naphthalen-1-yl)amino]-4H-benzo[d][1,3]oxazin-6-yl}-acetamide

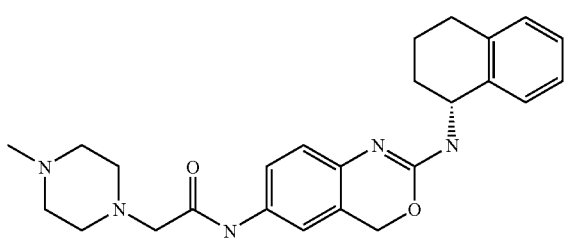

Step A: 2-Chloro-N-{2-[(R)-(1,2,3,4-tetrahydro-naphthalen-1-yl)amino]-4H-benzo[d][1,3]oxazin-6-yl}-acetamide: A mixture of (R)-N$^2$-(1,2,3,4-tetrahydro-naphthalen-1-yl)-4H-benzo[d][1,3]oxazine-2,6-diamine (Example 33) (293 mg, 1 mmol) and chloro-acetic acid 2,5-dioxo-pyrrolidin-1-yl ester (CAS 27243-15-8) (192 mg, 1 mmol) in acetonitrile (2 ml) was stirred at 23° C. for 1 h. Poured onto water and extracted with ethyl acetate, dried the combined organic layers over sodium sulfate, filtered off and evaporated totally to give the title compound as a light red oil (370 mg, 100%, HPLC 1.185 min), MS (ISP) m/e=370.1 [(M+H)$^+$] and 372 [(M+2H)$^+$].

Step B: 2-(4-Methyl-piperazin-1-yl)-N-{2-[(R)-(1,2,3,4-tetrahydro-naphthalen-1-yl)amino]-4H-benzo[d][1,3]oxazin-6-yl}-acetamide: Prepared from the above described 2-chloro-N-{2-[(R)-(1,2,3,4-tetrahydro-naphthalen-1-yl)amino]-4H-benzo[d][1,3]oxazin-6-yl}-acetamide (150 mg, 0.406 mmol, HPLC 1.185 min) and N-methylpiperazine (901 ul, 8.1 mmol) according to the procedure described for Example 3 step B. Obtained the title compound as a white foam (176 mg, 100%, HPLC 0.503 min), MS (ISP) m/e=434.4 [(M+H)$^+$].

EXAMPLE 39

2-Morpholin-4-yl-N-{2-[(R)-(1,2,3,4-tetrahydro-naphthalen-1-yl)amino]-4H-benzo[d][1,3]oxazin-6-yl}-acetamide

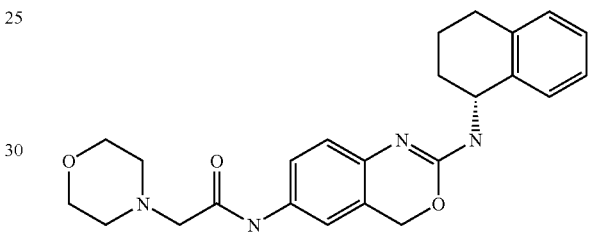

Prepared from 2-chloro-N-{2-[(R)-(1,2,3,4-tetrahydro-naphthalen-1-yl)amino]-4H-benzo[d][1,3]oxazin-6-yl}-acetamide (Example 38 step A) (150 mg, 0.406 mmol, HPLC 1.185 min) and morpholine (707 ul, 8.1 mmol) according to the procedure described for Example 3 step B. Obtained the title compound as a white foam (157 mg, 92%, HPLC 0.586 min), MS (ISP) m/e=421.2 [(M+H)$^+$].

EXAMPLE 40

2-(2-Methoxy-ethylamino)-N-{2-[(R)-(1,2,3,4-tetrahydro-naphthalen-1-yl)amino]-4H-benzo[d][1,3]oxazin-6-yl}-acetamide

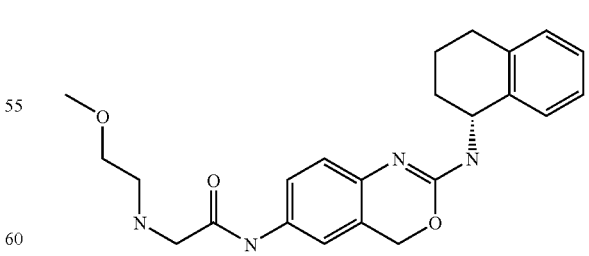

Prepared from 2-chloro-N-{2-[(R)-(1,2,3,4-tetrahydro-naphthalen-1-yl)amino]-4H-benzo[d][1,3]oxazin-6-yl}-acetamide (Example 38 step A) (150 mg, 0.406 mmol, HPLC 1.185 min) and 2-methoxyethylamine (700 ul, 8.1 mmol) according to the procedure described for Example 3 step B.

Obtained the title compound as an off-white solid (156 mg, 94%, HPLC 0.576 min), MS (ISP) m/e=409.3 [(M+H)+].

EXAMPLE 41

2-(2-Hydroxy-2-methyl-propylamino)-N-{2-[(R)-(1,2,3,4-tetrahydro-naphthalen-1-yl)amino]-4H-benzo[d][1,3]oxazin-6-yl}-acetamide

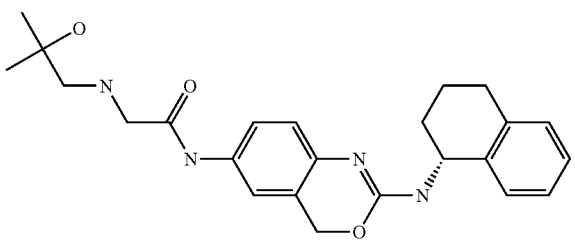

Prepared from 2-chloro-N-{2-[(R)-(1,2,3,4-tetrahydro-naphthalen-1-yl)amino]-4H-benzo[d][1,3]oxazin-6-yl}-acetamide (Example 38 step A) (150 mg, 0.406 mmol, HPLC 1.185 min) and 1-amino-2-methyl-propan-2-ol (723 mg, 8.1 mmol) in acetonitrile (3 ml) according to the procedure described for Example 3 step B. Obtained the title compound as an off-white solid (151 mg, 88%, HPLC 0.563 min), MS (ISP) m/e=423.3 [(M+H)+].

EXAMPLE 42 rac-N-[2-(6-Fluoro-2,3-dihydro-benzofuran-3-ylamino)-4H-benzo[d][1,3]oxazin-6-yl]-2-(2-methoxy-ethylamino)-acetamide

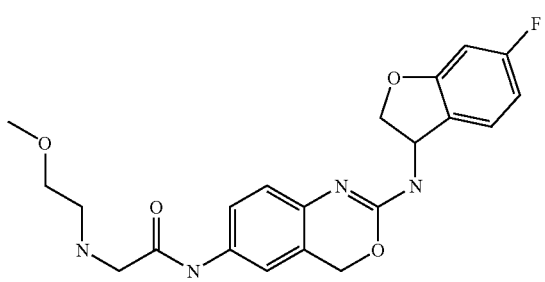

Step A: rac-2-Chloro-N-[2-(6-fluoro-2,3-dihydro-benzofuran-3-ylamino)-4H-benzo[d][1,3]oxazin-6-yl]-acetamide: Prepared from rac-N²-(6-fluoro-2,3-dihydro-benzofuran-3-yl)-4H-benzo[d][1,3]oxazine-2,6-diamine (Example 34) (748 mg, 2.5 mmol, HPLC 0.641 min) and chloroacetyl chloride (0.21 ml, 2.625 mmol) according to the procedure described for Example 3 step A. Obtained the title compound as a white solid (250 mg, 27%, HPLC 1.056 min), MS (ISP) m/e=376.1 [(M+H)+] and 378 [(M+2+H)+].

Step B: rac-N-[2-(6-Fluoro-2,3-dihydro-benzofuran-3-ylamino)-4H-benzo[d][1,3]oxazin-6-yl]-2-(2-methoxy-ethylamino)-acetamide: Prepared from the above described rac-2-chloro-N-[2-(6-fluoro-2,3-dihydro-benzofuran-3-ylamino)-4H-benzo[d][1,3]oxazin-6-yl]-acetamide (50 mg, 0.133 mmol, HPLC 1.056 min) and 2-methoxyethylamine (230 ul, 2.66 mmol) according to the procedure described for Example 3 step B. Obtained the title compound as a white solid (38 mg, 70%, HPLC 0.466 min 100%), MS (ISP) m/e=415.3 [(M+H)+].

EXAMPLE 43 rac-N-[2-(6-Fluoro-2,3-dihydro-benzofuran-3-ylamino)-4H-benzo[d][1,3]oxazin-6-yl]-2-(2-hydroxy-2-methyl-propylamino)-acetamide

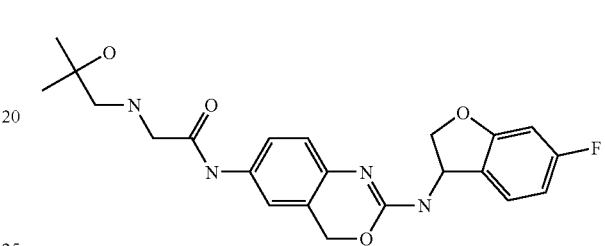

Prepared from rac-2-chloro-N-[2-(6-fluoro-2,3-dihydro-benzofuran-3-ylamino)-4H-benzo[d][1,3]oxazin-6-yl]-acetamide (Example 42 step A) (50 mg, 0.133 mmol, HPLC 1.056 min) and 1-amino-2-methyl-propan-2-ol (237 mg, 2.66 mmol) in acetonitrile (3 ml) according to the procedure described for Example 3 step B. Obtained the title compound as a white solid (57 mg, 100%, HPLC 0.473 min 100%), MS (ISP) m/e=429.3 [(M+H)+].

EXAMPLE 44 rac-N-[2-(6-Fluoro-2,3-dihydro-benzofuran-3-ylamino)-4H-benzo[d][1,3]oxazin-6-yl]-2-(4-methyl-piperazin-1-yl)-acetamide

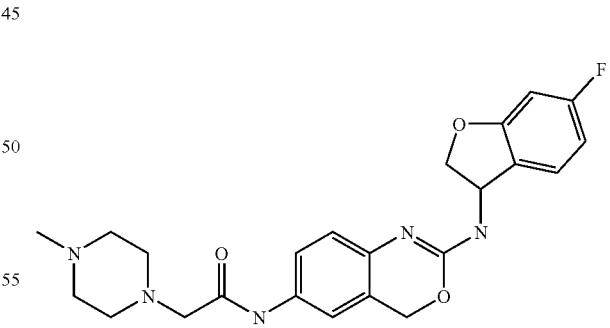

Prepared from rac-2-chloro-N-[2-(6-fluoro-2,3-dihydro-benzofuran-3-ylamino)-4H-benzo[d][1,3]oxazin-6-yl]-acetamide (Example 42 step A) (50 mg, 0.133 mmol, HPLC 1.056 min) and 1-methylpiperazine (300 ul, 2.66 mmol) according to the procedure described for Example 3 step B. Obtained the title compound as a white solid (58 mg, 99%, HPLC 0.468 min 100%), MS (ISP) m/e=440.3 [(M+H)+].

EXAMPLE 45 rac-N-[2-(6-Fluoro-2,3-dihydro-benzofuran-3-ylamino)-4H-benzo[d][1,3]oxazin-6-yl]-2-morpholin-4-yl-acetamide

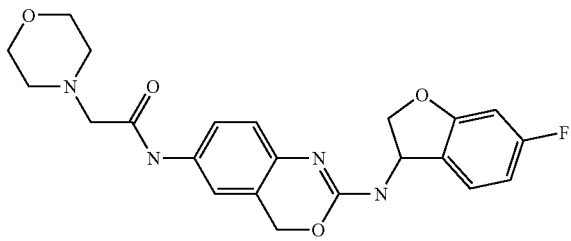

Prepared from rac-2-chloro-N-[2-(6-fluoro-2,3-dihydro-benzofuran-3-ylamino)-4H-benzo[d][1,3]oxazin-6-yl]-acetamide (Example 42 step A) (50 mg, 0.133 mmol, HPLC 1.056 min) and morpholine (231 ul, 2.66 mmol) according to the procedure described for Example 3 step B. Obtained the title compound as a white foam (57 mg, 100%, HPLC 0.525 min 100%), MS (ISP) m/e=427.1 [(M+H)$^+$].

EXAMPLE 46

$N^2$-(R)-Indan-1-yl-$N^6$-(4-trifluoromethyl-pyrimidin-2-yl)-4H-benzo[d][1,3]oxazine-2,6-diamine

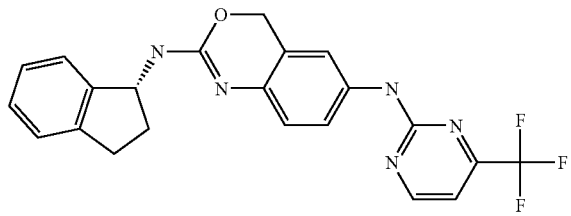

The title compound (100 mg, 47%), yellow foam, MS (ISP): m/e=426.1 (M+H$^+$), was prepared in accordance with the general method of Example 35 from (6-bromo-4H-benzo[d][1,3]oxazin-2-yl)-(R)-indan-1-yl-amine (Example 32) (172 mg, 0.5 mmol) and commercially available 2-amino-4-trifluoromethyl-pyrimidine (163 mg, 1.0 mmol).

EXAMPLE 47

$N^6$-(4,6-Dimethyl-pyrimidin-2-yl)-$N^2$-(R)-indan-1-yl-4H-benzo[d][1,3]oxazine-2,6-diamine

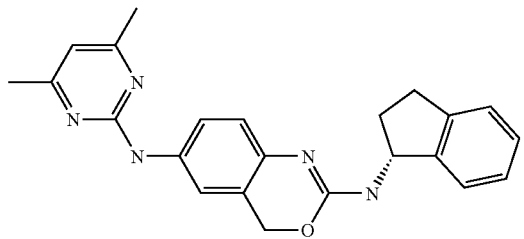

The title compound (22 mg, 11%), light brown foam, MS (ISP): m/e=422.2 (M+H$^+$), was prepared in accordance with the general method of Example 35 from (6-bromo-4H-benzo[d][1,3]oxazin-2-yl)-(R)-indan-1-yl-amine (Example 32) (172 mg, 0.5 mmol) and commercially available 2-amino-4,6-dimethyl-pyrimidine (123 mg, 1.0 mmol).

EXAMPLE 48

N-[2-((R)-Indan-1-ylamino)-4H-benzo[d][1,3]oxazin-6-yl]-acetamide

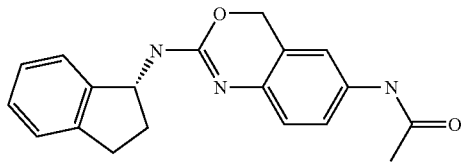

A mixture of (R)-N-2-indan-1-yl-4H-benzo[d][1,3]oxazine-2,6-diamine (Example 2) (100 mg, 0.358 mmol) in acetic acid (1 ml) and acetic anhydride (67.7 ul, 0.716 mmol) was stirred at 23° C. for 18 h. Poured into sat. sodium hydrogen carbonate-sol. and extracted twice with ethyl acetate, dried the organic layer over sodium sulfate, filtered off and evaporated totally, dried in HV to give the title compound as an off-white solid (115 mg, 100%), %), MS (ISP) m/e=322.2 [(M+H)$^+$].

EXAMPLE 49 rac-N,N-(Dimethyl)-N'-{2-(4-Methoxy-2,3-dihydro-benzofuran-3-ylamino)-4H-benzo[d][1,3]oxazin-6-yl}-sulfamide

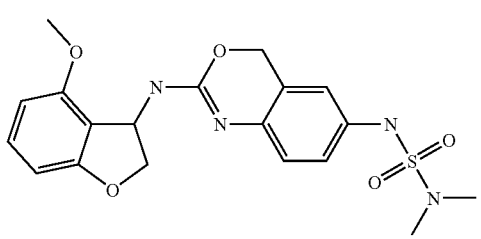

Prepared from rac-$N^2$-(4-methoxy-2,3-dihydro-benzofuran-3-yl)-4H-benzo[d][1,3]oxazine-2,6-diamine (Example 6) (100 mg, 0.321 mmol) and dimethylsulfamoyl chloride (37.9 ul, 0.353 mmol) according to the procedure described for Example 27. Obtained the title compound as an off-white solid (90 mg, 67%), MS (ISP) m/e=419.2 [(M+H)$^+$].

EXAMPLE 50 rac-Piperidine-1-sulfonic acid [2-(4-methoxy-2,3-dihydro-benzofuran-3-ylamino)-4H-benzo[d][1,3]oxazin-6-yl]-amide

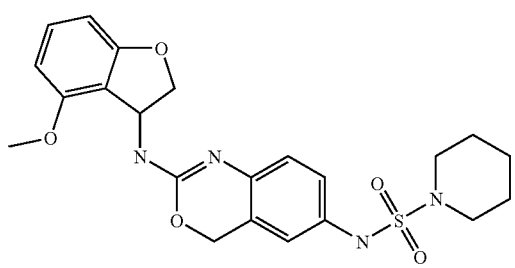

Prepared from rac-N²-(4-methoxy-2,3-dihydro-benzofuran-3-yl)-4H-benzo[d][1,3]oxazine-2,6-diamine (Example 6) (100 mg, 0.321 mmol) and piperidine-1-sulfonyl chloride (65 mg, 0.353 mmol) according to the procedure described for Example 27. Obtained the title compound as a light red foam (70 mg, 48%), MS (ISP) m/e=459.3 [(M+H)⁺].

EXAMPLE 51 rac-N-[2-(4-Methoxy-2,3-dihydro-benzofuran-3-ylamino)-4H-benzo[d][1,3]oxazin-6-yl]-acetamide

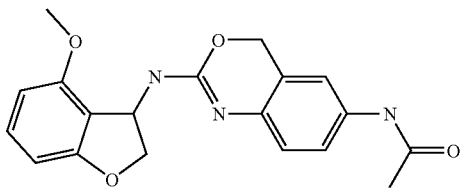

Prepared from rac-N²-(4-methoxy-2,3-dihydro-benzofuran-3-yl)-4H-benzo[d][1,3]oxazine-2,6-diamine (Example 6) (100 mg, 0.321 mmol) and acetic anhydride (60.7 ul, 0.642 mmol) according to the procedure described for Example 48. Obtained the title compound as a white solid (100 mg, 88%), MS (ISP) m/e=354.2 [(M+H)⁺].

EXAMPLE 52 rac-N-[2-(7-Methoxy-indan-1-ylamino)-4H-benzo[d][1,3]oxazin-6-yl]-acetamide

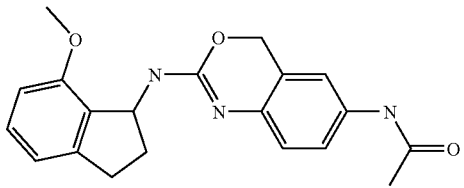

Prepared from rac-N²-(7-methoxy-indan-1-yl)-4H-benzo[d][1,3]oxazine-2,6-diamine (Example 10) (100 mg, 0.323 mmol) and acetic anhydride (61.1 ul, 0.646 mmol) according to the procedure described for Example 48. Obtained the title compound as a light brown foam (110 mg, 97%), MS (ISP) m/e=352.2 [(M+H)⁺].

EXAMPLE 53 rac-(6-Bromo-4H-benzo[d][1,3]oxazin-2-yl)-(5-fluoro-indan-1-yl)-amine

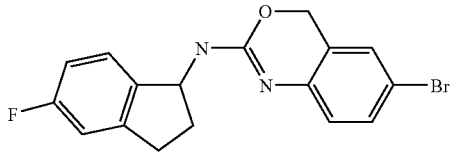

Prepared from (5-bromo-2-isothiocyanato-benzyloxy)-tert-butyl-dimethyl-silane (Example 32, step B) (4.0 g, 11.2 mmol) and rac-5-fluoro-indan-1-ylamine (CAS 148960-33-2) (1.69 mg, 11.2 mmol) according to the procedure described for Example 1. Obtained the title compound as a light brown oil (2.77 g, 69%), MS (ISP) m/e=361.1 [(M+H)⁺].

EXAMPLE 54 rac-(6-Bromo-4H-benzo[d][1,3]oxazin-2-yl)-(4-methoxy-2,3-dihydro-benzofuran-3-yl)-amine

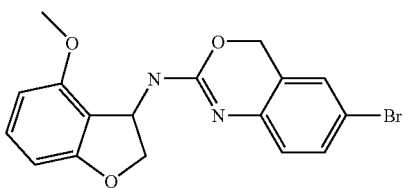

Prepared from (5-bromo-2-isothiocyanato-benzyloxy)-tert-butyl-dimethyl-silane (Example 32, step B) (4.0 g, 11.2 mmol) and rac-4-methoxy-2,3-dihydro-benzofuran-3-ylamine (Example 5, step B) (1.84 g, 11.2 mmol) according to the procedure described for Example 1. Obtained the title compound as a white solid (2.09 g, 50%), m.p. 132.5° C.; MS (ISP) m/e=375.1 [(M+H)⁺].

EXAMPLE 55 rac-N-[2-(7-Methoxy-indan-1-ylamino)-4H-benzo[d][1,3]oxazin-6-yl]-2-morpholin-4-yl-acetamide

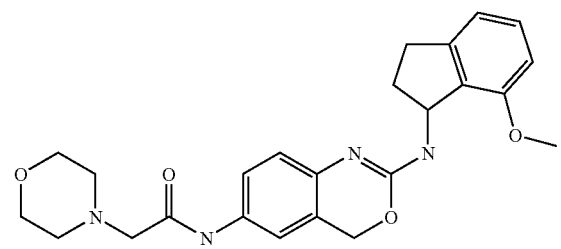

Step A: rac-2-Chloro-N-[2-(7-methoxy-indan-1-ylamino)-4H-benzo[d][1,3]oxazin-6-yl]-acetamide: Prepared from rac-N²-(7-methoxy-indan-1-yl)-4H-benzo[d][1,3]oxazine-2,6-diamine (Example 10) (620 mg, 2.00 mmol) and chloroacetyl chloride (168 ul, 2.10 mmol) according to the procedure described for Example 3 step A. Obtained the title compound as a light yellow solid (750 mg, 97%), MS (ISP) m/e=386.1 [(M+H)⁺] and 388 [(M+2+H)⁺].

Step B: rac-N-[2-(7-Methoxy-indan-1-ylamino)-4H-benzo[d][1,3]oxazin-6-yl]-2-morpholin-4-yl-acetamide: Prepared from the above described rac-2-chloro-N-[2-(7-methoxy-indan-1-ylamino)-4H-benzo[d][1,3]oxazin-6-yl]-acetamide (100 mg, 0.259 mmol) and morpholine (226 ul, 2.59 mmol) in acetonitrile (1 ml) according to the procedure described for Example 3 step B. Obtained the title compound as an off-white foam (110 mg, 97%), MS (ISP) m/e=437.2 [(M+H)⁺].

EXAMPLE 56 rac-N-[2-(5-Fluoro-indan-1-ylamino)-4H-benzo[d] [1,3]oxazin-6-yl]-2-morpholin-4-yl-acetamide

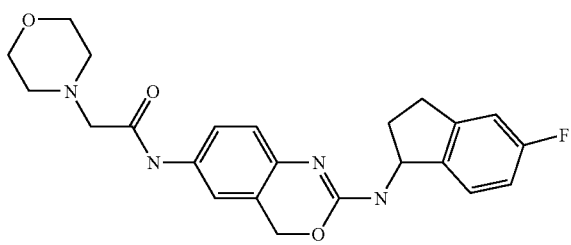

Step A: rac-2-Chloro-N-[2-(5-fluoro-indan-1-ylamino)-4H-benzo[d][1,3]oxazin-6-yl]-acetamide: Prepared from rac-N²-(5-fluoro-indan-1-yl)-4H-benzo[d][1,3]oxazine-2,6-diamine (Example 11) (300 mg, 1.01 mmol) and chloroacetyl chloride (85 ul, 1.06 mmol) according to the procedure described for Example 3 step A. Obtained the title compound as a light brown foam (370 mg, 98%), MS (ISP) m/e=374.2 [(M+H)⁺] and 376 [(M+2+H)⁺].

Step B: rac-N-[2-(7-Methoxy-indan-1-ylamino)-4H-benzo[d][1,3]oxazin-6-yl]-2-morpholin-4-yl-acetamide: Prepared from the above described rac-2-chloro-N-[2-(5-fluoro-indan-1-ylamino)-4H-benzo[d][1,3]oxazin-6-yl]-acetamide (100 mg, 0.268 mmol) and morpholine (117 ul, 1.338 mmol) in acetonitrile (1 ml) according to the procedure described for Example 3 step B. Obtained the title compound as an off-white foam (110 mg, 97%), MS (ISP) m/e=437.2 [(M+H)⁺].

EXAMPLE 57 rac-N²-(5-Fluoro-indan-1-yl)-N⁶-(6-trifluoromethyl-pyridin-2-yl)-4H-benzo[d][1,3]oxazine-2,6-diamine

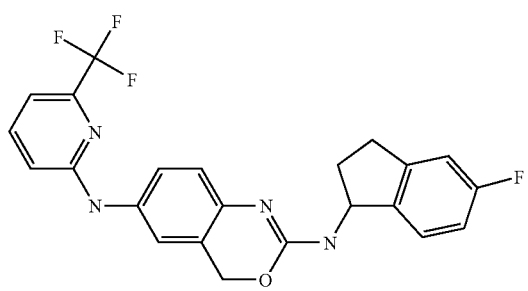

The title compound (91 mg, 41%), light brown foam, MS (ISP): m/e=443.3 (M+H⁺), was prepared in accordance with the general method of Example 35 from rac-(6-bromo-4H-benzo[d][1,3]oxazin-2-yl)-(5-fluoro-indan-1-yl)-amine (Example 53) (181 mg, 0.5 mmol) and commercially available 2-amino-6-trifluoromethyl-pyridine (162 mg, 1.0 mmol).

EXAMPLE 58 rac-N²-(5-Fluoro-indan-1-yl)-N⁶-(4-trifluoromethyl-pyrimidin-2-yl)-4H-benzo[d][1,3]oxazine-2,6-diamine

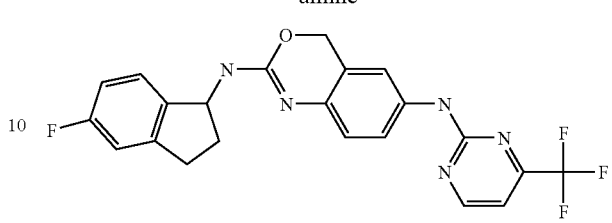

The title compound (113 mg, 51%), yellow foam, MS (ISP): m/e=444.2 (M+H⁺), was prepared in accordance with the general method of Example 35 from rac-(6-bromo-4H-benzo[d][1,3]oxazin-2-yl)-(5-fluoro-indan-1-yl)-amine (Example 53) (181 mg, 0.5 mmol) and commercially available 2-amino-4-trifluoromethyl-pyrimidine (163 mg, 1.0 mmol).

EXAMPLE 59 rac-N²-(4-Methoxy-2,3-dihydro-benzofuran-3-yl)-N⁶-(6-trifluoromethyl-pyridin-2-yl)-4H-benzo[d][1,3]oxazine-2,6-diamine

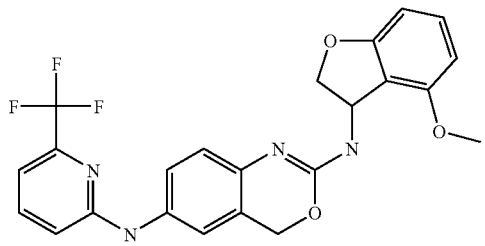

The title compound (28 mg, 12%), light brown foam, MS (ISP): m/e=457.3 (M+H⁺), was prepared in accordance with the general method of Example 35 from rac-(6-bromo-4H-benzo[d][1,3]oxazin-2-yl)-(4-methoxy-2,3-dihydro-benzofuran-3-yl)-amine (Example 54) (188 mg, 0.5 mmol) and commercially available 2-amino-6-trifluoromethyl-pyridine (162 mg, 1.0 mmol).

EXAMPLE 60 rac-N²-(4-Methoxy-2,3-dihydro-benzofuran-3-yl)-N⁶-(4-trifluoromethyl-pyrimidin-2-yl)-4H-benzo[d][1,3]oxazine-2,6-diamine

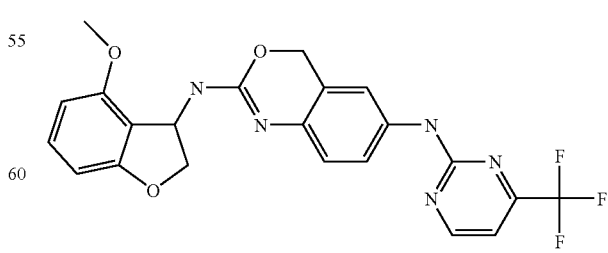

The title compound (135 mg, 59%), yellow foam, MS (ISP): m/e=458.2 (M+H⁺), was prepared in accordance with the general method of Example 35 from rac-(6-bromo-4H- benzo[d][1,3]oxazin-2-yl)-(4-methoxy-2,3-dihydro-benzo-furan-3-yl)-amine (example 54) (188 mg, 0.5 mmol) and commercially available 2-amino-4-trifluoromethyl-pyrimidine (163 mg, 1.0 mmol).

EXAMPLE 61 rac-N,N-(Dimethyl)-N'-{2-(7-Methoxy-indan-1-ylamino)-4H-benzo[d][1,3]oxazin-6-yl}-sulfamide

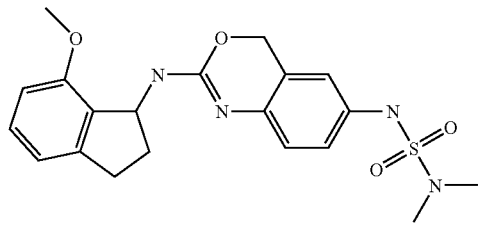

Prepared from rac-N$^2$-(7-methoxy-indan-1-yl)-4H-benzo[d][1,3]oxazine-2,6-diamine (Example 10) (100 mg, 0.323 mmol) and dimethylsulfamoyl chloride (38.1 ul, 0.356 mmol) according to the procedure described for Example 27. Obtained the title compound as a light yellow foam (75 mg, 56%), MS (ISP) m/e=417.3 [(M+H)$^+$].

EXAMPLE 62 rac-Piperidine-1-sulfonic acid [2-(7-methoxy-indan-1-ylamino)-4H-benzo[d][1,3]oxazin-6-yl]-amide

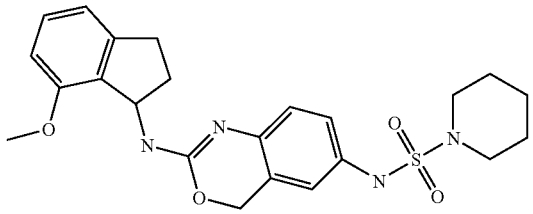

Prepared from rac-N$^2$-(7-methoxy-indan-1-yl)-4H-benzo[d][1,3]oxazine-2,6-diamine (Example 10) (100 mg, 0.323 mmol) and piperidine-1-sulfonyl chloride (65 mg, 0.353 mmol) according to the procedure described for Example 27. Obtained the title compound as a light yellow foam (110 mg, 75%), MS (ISP) m/e=457.4 [(M+H)$^+$].

EXAMPLE 63 rac-Morpholine-4-sulfonic acid [2-(7-methoxy-indan-1-ylamino)-4H-benzo[d][1,3]oxazin-6-yl]-amide

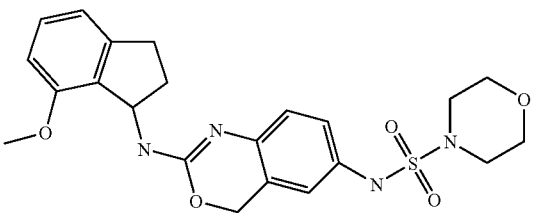

Prepared from rac-N$^2$-(7-methoxy-indan-1-yl)-4H-benzo[d][1,3]oxazine-2,6-diamine (Example 10) (100 mg, 0.323 mmol) and morpholin-4-sulfonyl chloride (66 mg, 0.356 mmol) according to the procedure described for Example 27. Obtained the title compound as a light yellow foam (80 mg, 54%), MS (ISP) m/e=459.2 [(M+H)$^+$].

EXAMPLE 64 rac-N,N-(Dimethyl)-N'-{2-(5-Fluoro-indan-1-ylamino)-4H-benzo[d][1,3]oxazin-6-yl}-sulfamide

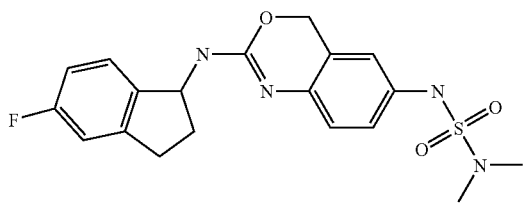

Prepared from rac-N$^2$-(5-fluoro-indan-1-yl)-4H-benzo[d][1,3]oxazine-2,6-diamine (Example 11) (100 mg, 0.336 mmol) and dimethylsulfamoyl chloride (39.7 ul, 0.370 mmol) according to the procedure described for Example 27. Obtained the title compound as an off-white foam (90 mg, 59%), MS (ISP) m/e=405.3 [(M+H)$^+$].

EXAMPLE 65

N-[2-((R)-Indan-1-ylamino)-4H-benzo[d][1,3]oxazin-6-yl]-2-thiomorpholin-4-yl-acetamide

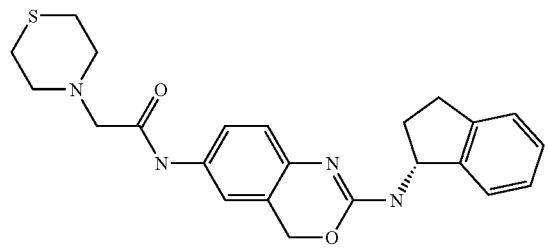

Prepared from 2-chloro-N-[2-((R)-indan-1-ylamino)-4H-benzo[d][1,3]oxazin-6-yl]-acetamide (Example 3 step A) (100 mg, 0.281 mmol) and thiomorpholine (0.141 ml, 1.405 mmol) in acetonitrile (1 ml) according to the procedure described for Example 3 step B. Obtained the title compound as an off-white foam (90 mg, 76%), MS (ISP) m/e=423.2 [(M+H)$^+$].

EXAMPLE 66

2-(1,1-Dioxo-1λ$^6$-thiomorpholin-4-yl)-N-[2-((R)-indan-1-ylamino)-4H-benzo[d][1,3]oxazin-6-yl]-acetamide

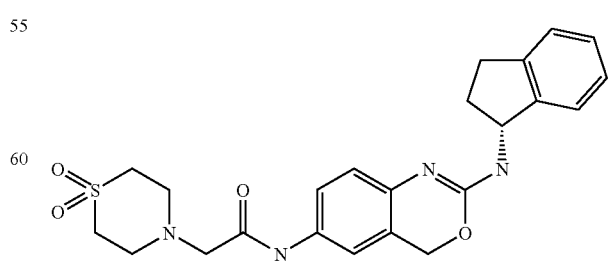

Prepared from 2-chloro-N-[2-((R)-indan-1-ylamino)-4H-benzo[d][1,3]oxazin-6-yl]-acetamide (Example 3 step A)

(100 mg, 0.281 mmol) and thiomorpholine 1,1 dioxide (190 mg, 1.405 mmol) in acetonitrile (1 ml) according to the procedure described for Example 3 step B. Obtained the title compound as a white solid (15 mg, 12%), MS (ISP) m/e=455.3 [(M+H)+].

EXAMPLE 67

2-Imidazol-1-yl-N-[2-((R)-indan-1-ylamino)-4H-benzo[d][1,3]oxazin-6-yl]-acetamide

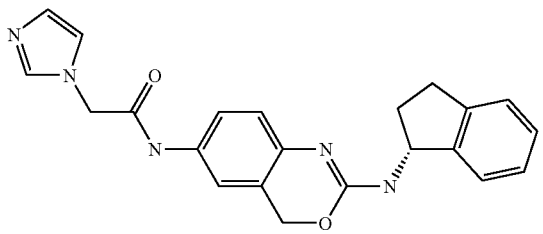

Prepared from 2-chloro-N-[2-((R)-indan-1-ylamino)-4H-benzo[d][1,3]oxazin-6-yl]-acetamide (Example 3 step A) (100 mg, 0.281 mmol) and imidazole (96 mg, 1.405 mmol) in acetonitrile (1 ml) according to the procedure described for Example 3 step B. Obtained the title compound as a white solid (80 mg, 73%), MS (ISP) m/e=388.3 [(M+H)+].

EXAMPLE 68

2-(2-Hydroxy-2-methyl-propylamino)-N-[2-((R)-indan-1-ylamino)-4H-benzo[d][1,3]oxazin-6-yl]-acetamide

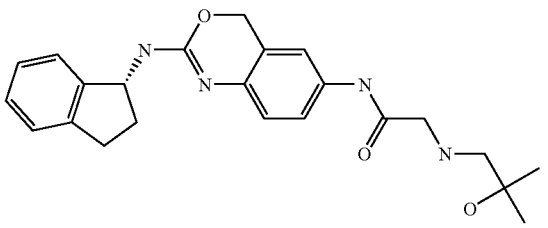

Prepared from 2-chloro-N-[2-((R)-indan-1-ylamino)-4H-benzo[d][1,3]oxazin-6-yl]-acetamide (Example 3 step A) (100 mg, 0.281 mmol) and 1-amino-2-methyl-propan-2-ol (126 mg, 1.405 mmol) in acetonitrile (1 ml) according to the procedure described for Example 3 step B. Obtained the title compound as a white solid (60 mg, 52%), MS (ISP) m/e=409.3 [(M+H)+].

EXAMPLE 69

N-[2-((R)-Indan-1-ylamino)-4H-benzo[d][1,3]oxazin-6-yl]-2-(2-methoxy-ethylamino)-acetamide

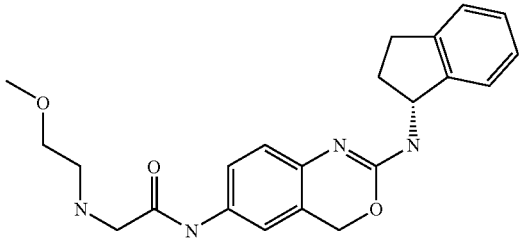

Prepared from 2-chloro-N-[2-((R)-indan-1-ylamino)-4H-benzo[d][1,3]oxazin-6-yl]-acetamide (Example 3 step A) (100 mg, 0.281 mmol) and 1-methoxyethylamine (0.12 ml, 1.405 mmol) in acetonitrile (1 ml) according to the procedure described for Example 3 step B. Obtained the title compound as a white solid (70 mg, 63%), MS (ISP) m/e=395.2 [(M+H)+].

EXAMPLE 70

N-[2-((R)-Indan-1-ylamino)-4H-benzo[d][1,3]oxazin-6-yl]-2-[4-(2,2,2-trifluoro-ethyl)-piperazin-1-yl]-acetamide

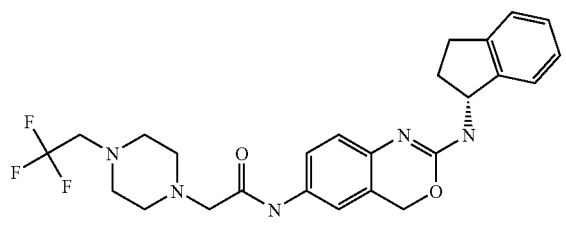

Prepared from 2-chloro-N-[2-((R)-indan-1-ylamino)-4H-benzo[d][1,3]oxazin-6-yl]-acetamide (Example 3 step A) (100 mg, 0.281 mmol) and commercially available 1-(2,2,2-trifluorethyl)piperazine hydrochloride (CAS 13349-91-2) (87 mg, 0.422 mmol) in acetonitrile (1 ml) with diisopropylethyl amine (0.24 ml, 1.405 mmol) according to the procedure described for Example 3 step B. Obtained the title compound as a white foam (105 mg, 77%), MS (ISP) m/e=488.3 [(M+H)+].

EXAMPLE 71

4-Methyl-piperazine-1-sulfonic acid {2-[(R)-(1,2,3,4-tetrahydro-naphthalen-1-yl)amino]-4H-benzo[d][1,3]oxazin-6-yl}-amide

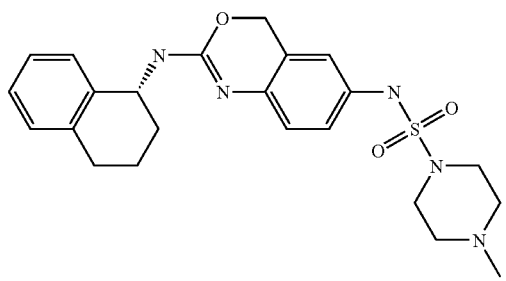

Prepared from (R)-N²-(1,2,3,4-tetrahydro-naphthalen-1-yl)-4H-benzo[d][1,3]oxazine-2,6-diamine (Example 33) (100 mg, 0.341 mmol) and 4-methyl-piperazine-1-sulfonyl chloride (CAS 1688-95-5) (74 mg, 0.375 mmol) according to the procedure described for Example 27. Obtained the title compound as a light brown oil (94 mg, 61%), MS (ISP) m/e=456.3 [(M+H)+].

EXAMPLE 72

4-Methyl-piperazine-1-sulfonic acid [2-((R)-indan-1-ylamino)-4H-benzo[d][1,3]oxazin-6-yl]-amide

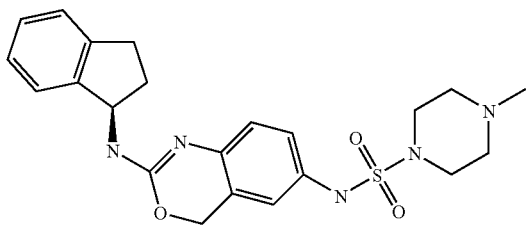

Prepared from (R)-N-2-indan-1-yl-4H-benzo[d][1,3]oxazine-2,6-diamine (Example 2) (100 mg, 0.341 mmol) and 4-methyl-piperazine-1-sulfonyl chloride (CAS 1688-95-5) (78 mg, 0.394 mmol) according to the procedure described for Example 27. Obtained the title compound as a light brown oil (45 mg, 29%), MS (ISP) m/e=442.3 [(M+H)+].

EXAMPLE 73

2-((exo)-8-Isopropyl-8-aza-bicyclo[3.2.1]oct-3-ylamino)-N-{2-[(R)-(1,2,3,4-tetrahydro-naphthalen-1-yl)amino]-4H-benzo[d][1,3]oxazin-6-yl}-acetamide

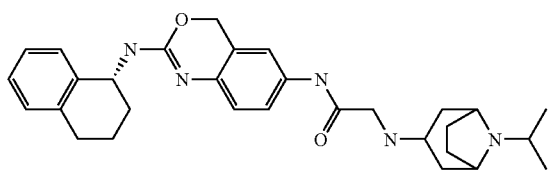

Step A: 8-Isopropyl-8-aza-bicyclo[3.2.1]octan-3-one oxime: A mixture of 8-isopropyl-8-aza-bicyclo[3.2.1]octan-3-one (CAS 3423-28-7)(20.0 g, 120 mmol) in ethanol (500 ml) and pyridine (14.5 ml, 179 mmol) with hydroxylamine hydrochloride (8.81 g, 127 mmol) was refluxed for 16 h. Cooled to 23° C., the precipitate was filtered off, washed with diethyl ether leaving a solid, which was partitioned between dichloromethane and sodium carbonate solution, the organic layers dried over sodium sulfate, filtered and the solvents evaporated to give the title compound as a white solid. (17.7 g, 82%), MS: m/e=183.2 (M+H+).

Step B: (3-exo)-8-Isopropyl-8-aza-bicyclo[3.2.1]oct-3-ylamine dihydrochloride: A solution of the above described 8-isopropyl-8-aza-bicyclo[3.2.1]octan-3-one oxime (4.31 g, 24 mmol) in pentanol (108 ml) was heated under reflux (150° C.). Sodium (6.685 g, 290.8 mmol) was added portionwise over 2 h. The reaction was then heated under reflux for further 2 h, then cooled to 0° C. Water was added until no more hydrogen gas was evolved. The mixture was acidified using 6 N HCl. The phases were separated, extracted the organic layer twice with 6 N HCl. The combined aqueos extracts were made alkaline in an ice bath with NaOH pellets to achieve pH 12. Extracted 3 times with dichloromethane, dried the combined organic layers over sodium sulfate, filtered off and evaporated totally to give a light yellow oil (5 g contains pentanol). Dissolved in 20 ml ethanol and added trimethylchlorosilane (18.2 ml, 144.1 mmol), then added 250 ml diethyl ether and stirred overnight. Filtered the solid off and dried in HV to give the title compound as white crystals (5.7 g, 100%), MS: m/e=169.2 (M+H+).

Step C: 2-((exo)-8-Isopropyl-8-aza-bicyclo[3.2.1]oct-3-ylamino)-N-{2-[(R)-(1,2,3,4-tetrahydro-naphthalen-1-yl)amino]-4H-benzo[d][1,3]oxazin-6-yl}-acetamide: Prepared from 2-chloro-N-{2-[(R)-(1,2,3,4-tetrahydro-naphthalen-1-yl)amino]-4H-benzo[d][1,3]oxazin-6-yl}-acetamide (Example 38 step A) (150 mg, 0.406 mmol, HPLC 1.185 min) and the above described (3-exo)-8-isopropyl-8-aza-bicyclo[3.2.1]oct-3-ylamine dihydrochloride (242 mg, 1.0 mmol) in acetonitrile (3 ml) with diisopropylethyl amine (0.51 ml, 3.0 mmol) according to the procedure described for Example 3 step B. Obtained the title compound as a white solid (82 mg, 33%, HPLC 1.681 min), MS (ISP) m/e=502.3 [(M+H)+].

EXAMPLE 74 rac-(6-Bromo-4H-benzo[d][1,3]oxazin-2-yl)-(7-methoxy-indan-1-yl)-amine

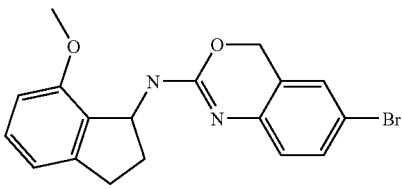

Prepared from (5-bromo-2-isothiocyanato-benzyloxy)-tert-butyl-dimethyl-silane (Example 32, step B) (4.0 g, 11.2 mmol) and the rac-7-methoxy-indan-1-ylamine (Example 10, step A) (1.82 g, 11.2 mmol) according to the procedure described for Example 1. Obtained the title compound as a white solid (2.79 g, 67%), m.p. 151° C.; MS (ISP) m/e=375.1 [(M+H)+].

EXAMPLE 75 rac-N²-Chroman-4-yl-4H-benzo[d][1,3]oxazine-2,6-diamine

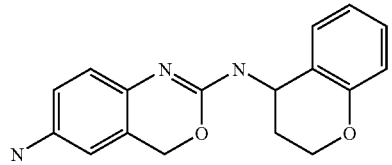

Step A: rac-Chroman-4-yl-(6-nitro-4H-benzo[d][1,3]oxazin-2-yl)-amine: Prepared from tert-butyl-(2-isothiocyanato-5-nitro-benzyloxy)-dimethyl-silane (Example C1) (2.271 g, 7.0 mmol; HPLC: 4.446 min) and rac-chroman-4-ylamine (CAS 53981-38-7) (1.044 g, 7.0 mmol; 0.374 min) according to the procedure described for Example 1. Obtained the title compound as a yellow solid (1.98 g, 87%, HPLC 2.031 min), MS (ISP) m/e=326.2 [(M+H)+].

Step B: rac-N²-Chroman-4-yl-4H-benzo[d][1,3]oxazine-2,6-diamine: Prepared from the above described rac-chroman-4-yl-(6-nitro-4H-benzo[d][1,3]oxazin-2-yl)-amine (1.95 g, 6.0 mmol, HPLC 2.031 min) according to the procedure described for Example 2 step B. Obtained the title compound as a light yellow foam (1.77 g, 100%, HPLC 0.699 min), MS (ISP) m/e=296.3 [(M+H)+].

EXAMPLE 76

N-[2-((R)-Indan-1-ylamino)-4H-benzo[d][1,3]oxazin-6-yl]-2-((exo)-8-isopropyl-8-aza-bicyclo[3.2.1]oct-3-ylamino)-acetamide

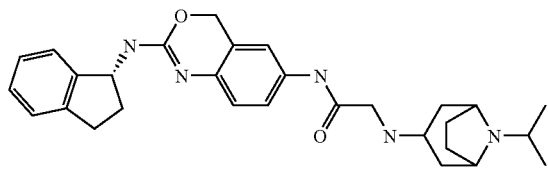

Prepared from 2-chloro-N-[2-((R)-indan-1-ylamino)-4H-benzo[d][1,3]oxazin-6-yl]-acetamide (Example 3 step A) (100 mg, 0.281 mmol) and (3-exo)-8-isopropyl-8-aza-bicyclo[3.2.1]oct-3-ylamine dihydrochloride (Example 73 step B) (102 mg, 0.422 mmol) in acetonitrile (1 ml) with diisopropylethyl amine (0.287 ml, 1.69 mmol) according to the procedure described for Example 3 step B. Obtained the title compound as an off-white solid (35 mg, 26%), MS (ISP) m/e=488.4 [(M+H)+].

EXAMPLE 77

$N^2$-(5-Methyl-furan-2-ylmethyl)-4H-benzo[d][1,3]oxazine-2,6-diamine

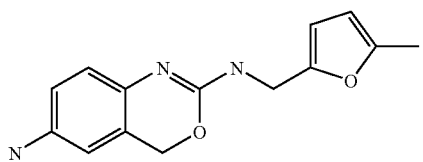

Step A: (5-Methyl-furan-2-ylmethyl)-(6-nitro-4H-benzo[d][1,3]oxazin-2-yl)-amine: Prepared from tert-butyl-(2-isothiocyanato-5-nitro-benzyloxy)-dimethyl-silane (Example C1) (2.0 g, 6.16 mmol; HPLC: 4.446 min) and 5-methyl-2-furanmethanamine (CAS 14003-16-8) (0.685 g, 6.163 mmol) according to the procedure described for Example 1. Obtained the title compound as a yellow solid (1.40 g, 79%, HPLC 1.624 min), MS (ISP) m/e=326.2 [(M+H)+].

Step B: N-2-(5-Methyl-furan-2-ylmethyl)-4H-benzo[d][1,3]oxazine-2,6-diamine: Prepared from the above described (5-methyl-furan-2-ylmethyl)-(6-nitro-4H-benzo[d][1,3]oxazin-2-yl)-amine (1.4 g, 4.873 mmol) according to the procedure described for Example 2 step B. Obtained the title compound as a light brown solid (1.15 g, 92%, MS (ISP) m/e=258.1 [(M+H)+].

EXAMPLE 78

N-[2-((R)-Indan-1-ylamino)-4H-benzo[d][1,3]oxazin-6-yl]-methanesulfonamide

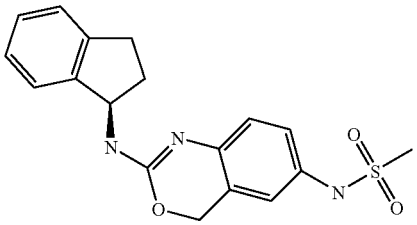

Prepared from (R)-N-2-indan-1-yl-4H-benzo[d][1,3]oxazine-2,6-diamine (Example 2) (140 mg, 0.50 mmol, HPLC 0.642 min) and methanesulfonyl chloride (43 ul, 0.55 mmol) according to the procedure described for Example 27. Obtained the title compound as an off-white foam (100 mg, 56%, HPLC 1.278 min), MS (ISP) m/e=358.2 [(M+H)+].

EXAMPLE 79

Cyclopropanesulfonic acid [2-((R)-indan-1-ylamino)-4H-benzo[d][1,3]oxazin-6-yl]-amide

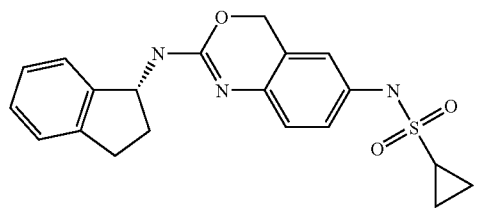

Prepared from (R)-N-2-indan-1-yl-4H-benzo[d][1,3]oxazine-2,6-diamine (Example 2) (140 mg, 0.50 mmol, HPLC 0.642 min) and cyclopropanesulfonyl chloride (77 mg, 0.55 mmol) according to the procedure described for Example 27. Obtained the title compound as a light yellow solid (138 mg, 72%, HPLC 1.294 min), MS (ISP) m/e=358.2 [(M+H)+].

EXAMPLE 80 rac-$N^2$-(7-Methoxy-indan-1-yl)-$N^6$-(6-trifluoromethyl-pyridin-2-yl)-4H-benzo[d][1,3]oxazine-2,6-diamine

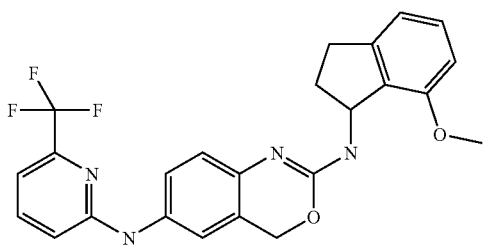

The title compound (144 mg, 63%), light brown foam, MS (ISP): m/e=455.3 (M+H+), was prepared in accordance with the general method of Example 35 from rac-(6-bromo-4H-benzo[d][1,3]oxazin-2-yl)-(7-methoxy-indan-1-yl)-amine (Example 74) (187 mg, 0.5 mmol) an commercially available 2-amino-6-trifluoromethyl-pyridine (162 mg, 1.0 mmol).

EXAMPLE 81 rac-$N^2$-(7-Methoxy-indan-1-yl)-$N^6$-(4-trifluoromethyl-pyrimidin-2-yl)-4H-benzo[d][1,3]oxazine-2,6-diamine

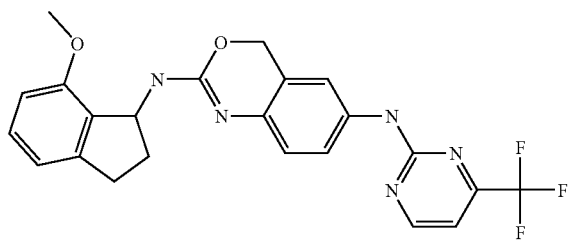

The title compound (141 mg, 62%), yellow foam, MS (ISP): m/e=456.3 (M+H$^+$), was prepared in accordance with the general method of Example 35 from rac-(6-bromo-4H-benzo[d][1,3]oxazin-2-yl)-(7-methoxy-indan-1-yl)-amine (Example 74) (187 mg, 0.5 mmol) and commercially available 2-amino-4-trifluoromethyl-pyrimidine (163 mg, 1.0 mmol).

EXAMPLE 82

Cyclopropanecarboxylic acid {2-[(5-methyl-furan-2-ylmethyl)-amino]-4H-benzo[d][1,3]oxazin-6-yl}-amide

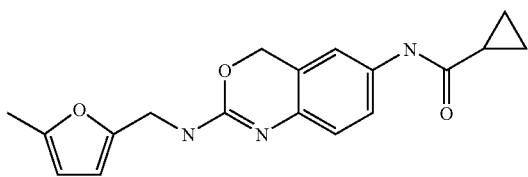

Prepared from N-2-(5-methyl-furan-2-ylmethyl)-4H-benzo[d][1,3]oxazine-2,6-diamine (Example 77) (100 mg, 0.389 mmol) and cyclopropylcarbonyl chloride (38 ul, 0.408 mmol) according to the procedure described for Example 3 step A. Obtained the title compound as a white solid (90 mg, 71%), MS (ISP) m/e=326.2 [(M+H)$^+$].

EXAMPLE 83

N-[2-((R)-Indan-1-ylamino)-4H-benzo[d][1,3]oxazin-6-yl]-benzenesulfonamide

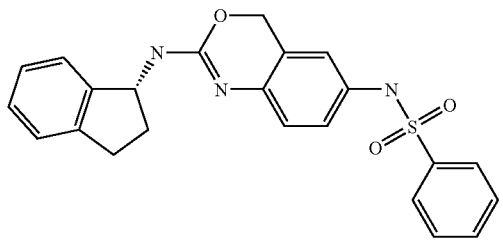

Prepared from (R)-N-2-indan-1-yl-4H-benzo[d][1,3]oxazine-2,6-diamine (Example 2) (140 mg, 0.50 mmol, HPLC 0.642 min) and benzenesulfonyl chloride (97 mg, 0.55 mmol) according to the procedure described for Example 27.

Obtained the title compound as an off-white foam (116 mg, 55%, HPLC 1.542 min), MS (ISP) m/e=420.1 [(M+H)$^+$].

EXAMPLE 84

N-{2-[(5-Methyl-furan-2-ylmethyl)-amino]-4H-benzo[d][1,3]oxazin-6-yl}-2-(4-methyl-piperazin-1-yl)-acetamide

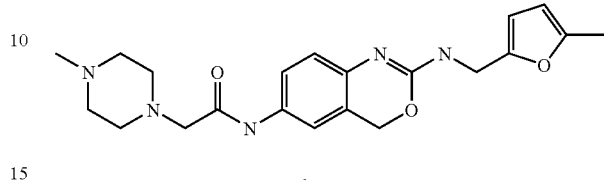

Step A: 2-Chloro-N-{2-[(5-methyl-furan-2-ylmethyl)-amino]-4H-benzo[d][1,3]oxazin-6-yl}-acetamide: Prepared from N-2-(5-methyl-furan-2-ylmethyl)-4H-benzo[d][1,3]oxazine-2,6-diamine (Example 77) (500 mg, 1.943 mmol) and chloroacetyl chloride (163 ul, 2.04 mmol) according to the procedure described for Example 3 step A. Obtained the title compound as a light yellow solid (610 mg, 94%), MS (ISP) m/e=334.2 [(M+H)$^+$] and 336 [(M+2+H)$^+$].

Step B: N-{2-[(5-Methyl-furan-2-ylmethyl)-amino]-4H-benzo[d][1,3]oxazin-6-yl}-2-(4-methyl-piperazin-1-yl)-acetamide: Prepared from the above described 2-chloro-N-{2-[(5-methyl-furan-2-ylmethyl)-amino]-4H-benzo[d][1,3]oxazin-6-yl}-acetamide (100 mg, 0.300 mmol) and 1-methylpiperazine (0.333 ml 2.996 mmol) in acetonitrile (1 ml) according to the procedure described for Example 3 step B. Obtained the title compound as an off-white foam (85 mg, 71%), MS (ISP) m/e=398.2 [(M+H)$^+$].

EXAMPLE 85

N-{2-[(5-Methyl-furan-2-ylmethyl)-amino]-4H-benzo[d][1,3]oxazin-6-yl}-2-morpholin-4-yl-acetamide

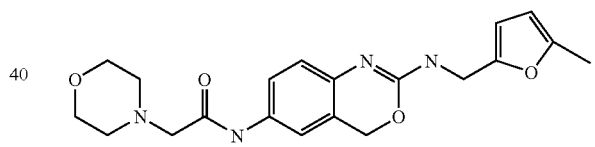

Prepared from the above described 2-chloro-N-{2-[(5-methyl-furan-2-ylmethyl)-amino]-4H-benzo[d][1,3]oxazin-6-yl}-acetamide (100 mg, 0.300 mmol) and morpholine (0.260 ml 2.996 mmol) in acetonitrile (1 ml) according to the procedure described for Example 3 step B. Obtained the title compound as a white solid (100 mg, 87%), MS (ISP) m/e=385.3 [(M+H)$^+$].

EXAMPLE 86 rac-N-[2-(7-Methoxy-indan-1-ylamino)-4H-benzo[d][1,3]oxazin-6-yl]-2-(4-methyl-piperazin-1-yl)-acetamide

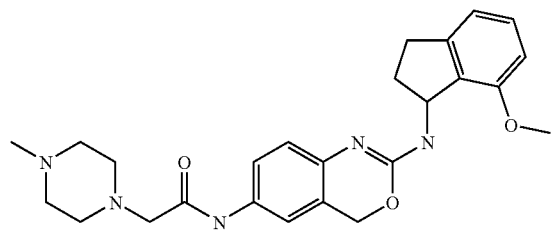

Prepared from rac-2-chloro-N-[2-(7-methoxy-indan-1-ylamino)-4H-benzo[d][1,3]oxazin-6-yl]-acetamide (Example 55 step A) (100 mg, 0.259 mmol) and 1-methylpiperazine (0.289 ml 2.595 mmol) in acetonitrile (1 ml) according to the procedure described for Example 3 step B. Obtained the title compound as a light yellow foam (90 mg, 77%), MS (ISP) m/e=450.2 [(M+H)$^+$].

EXAMPLE 87

N$^2$-(2-Phenoxy-ethyl)-4H-benzo[d][1,3]oxazine-2,6-diamine

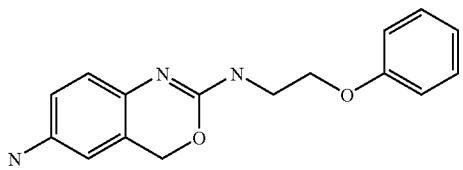

Step A: (6-Nitro-4H-benzo[d][1,3]oxazin-2-yl)-(2-phenoxy-ethyl)-amine: Prepared from tert-butyl-(2-isothiocyanato-5-nitro-benzyloxy)-dimethyl-silane (Example C1) (1.95 g, 6.0 mmol; HPLC: 4.446 min) and 2-phenoxyethylamine (CAS 1758-46-9) (807 mg, 6.0 mmol; HPLC: 0.381 min) according to the procedure described for Example 1. Obtained the title compound as a yellow solid (1.80 g, 96%, HPLC 1.789 min), MS (ISP) m/e=314.0 [(M+H)$^+$].

Step B: N$^2$-(2-Phenoxy-ethyl)-4H-benzo[d][1,3]oxazine-2,6-diamine: Prepared from the above described (6-nitro-4H-benzo[d][1,3]oxazin-2-yl)-(2-phenoxy-ethyl)-amine (0.55 g, 1.755 mmol, HPLC 1.789 min) according to the procedure described for Example 2 step B. Obtained the title compound as a light yellow foam (0.50 g, 100%, HPLC 0.708 min), MS (ISP) m/e=284.2 [(M+H)$^+$].

EXAMPLE 88

N$^2$—(R)-Indan-1-yl-N$^6$-pyridin-3-ylmethyl-4H-benzo[d][1,3]oxazine-2,6-diamine

To a solution of (R)—N-2-indan-1-yl-4H-benzo[d][1,3]oxazine-2,6-diamine (Example 2) (200 mg, 0.716 mmol) and 3-pyridinecarboxaldehyde (CAS 500-22-1) (68 ul, 0.716 mmol) in methanol (5 ml) and acetic acid (0.5 ml) at 0° C. was added sodium cyanoborohydride (50 mg, 0.788 mmol) and the mixture was stirred at 23° C. for 1 h. Poured into sat. sodium hydrogen carbonate-sol. and extracted twice with ethyl acetate, dried the organic layer over sodium sulfate. After filtration the solvent was removed in vacuum to give a crude product which was purified by silica gel column chromatography with ethyl acetate to give the title compound as a light yellow foam (170 mg, 64%), MS (ISP) m/e=371.2 [(M+H)$^+$].

EXAMPLE 89

N$^2$—(R)-Indan-1-yl-N$^6$-thiazol-2-ylmethyl-4H-benzo[d][1,3]oxazine-2,6-diamine

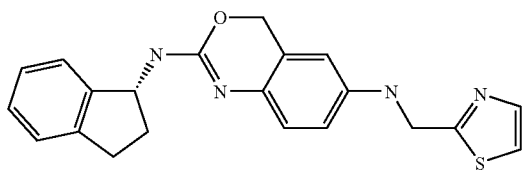

Prepared from (R)—N-2-indan-1-yl-4H-benzo[d][1,3]oxazine-2,6-diamine (Example 2) (200 mg, 0.716 mmol) and 2-thiazolecarboxaldehyde (CAS 10200-59-6) (63 ul, 0.716 mmol) according to the procedure described for Example 88. Obtained the title compound as a light yellow foam (70 mg, 26%), MS (ISP) m/e=377.3 [(M+H)$^+$].

EXAMPLE 90 rac-Cyclopropanecarboxylic acid [2-(chroman-4-ylamino)-4H-benzo[d][1,3]oxazin-6-yl]-amide

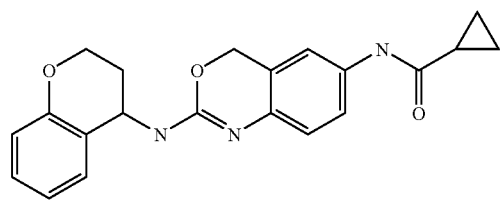

Prepared from rac-N$^2$-chroman-4-yl-4H-benzo[d][1,3]oxazine-2,6-diamine (Example 75) (295 mg, 1.0 mmol, HPLC 0.699 min) and cyclopropanecarbonyl chloride (115 mg, 0.55 mmol) according to the procedure described for Example 27. Obtained the title compound as an off-white foam (100 mg, 28%, HPLC 1.353 min), MS (ISP) m/e=364.3 [(M+H)$^+$].

EXAMPLE 91 rac-N,N-(Dimethyl)-N'-{2-(chroman-4-ylamino)-4H-benzo[d][1,3]oxazin-6-yl}-sulfamide

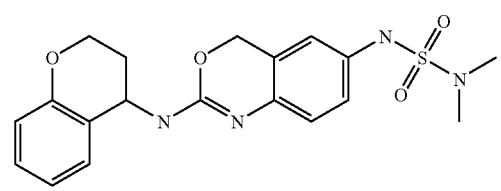

Prepared from rac-N$^2$-chroman-4-yl-4H-benzo[d][1,3]oxazine-2,6-diamine (Example 75) (295 mg, 1.0 mmol, HPLC 0.699 min) and dimethylsulfamoyl chloride (91 ul, 0.55 mmol) according to the procedure described for Example 27. Obtained the title compound as light yellow oil (187 mg, 46%, HPLC 1.254 min), MS (ISP) m/e=403.4 [(M+H)⁺].

EXAMPLE 92

N²-Cycloheptyl-4H-benzo[d][1,3]oxazine-2,6-diamine

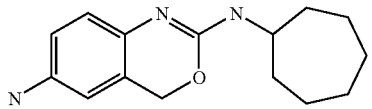

Step A: Cycloheptyl-(6-nitro-4H-benzo[d][1,3]oxazin-2-yl)-amine: Prepared from tert-butyl-(2-isothiocyanato-5-nitro-benzyloxy)-dimethyl-silane (Example C1) (5.0 g, 15 mmol) and cycloheptylamine (1.8 g, 16 mmol) according to the procedure described for Example 1. Obtained the title compound as a yellow foam (4.3 g, 100%), MS (ISP) m/e=288.3 [(M−H)⁺].

Step B: N²-Cycloheptyl-4H-benzo[d][1,3]oxazine-2,6-diamine: Prepared from the above described cycloheptyl-(6-nitro-4H-benzo[d][1,3]oxazin-2-yl)-amine (4.3 g, 15 mmol) according to the procedure described for Example 2 step B. Obtained the title compound as a light yellow foam (3.5 g, 90%), MS (ISP) m/e=260.3 [(M+H)⁺].

EXAMPLE 93

N-(2-Cycloheptylamino-4H-benzo[d][1,3]oxazin-6-yl)-2-(4-methyl-piperazin-1-yl)-acetamide

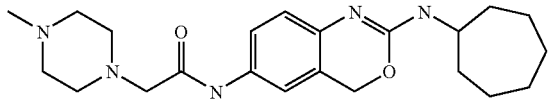

(4-Methyl-piperazin-1-yl)-acetic acid (167 mg, 1.1 mmol), N,N-diisopropyl ethyl amine (398 mg, 3.1 mmol) and 2-(1H-benzotriazole-1-yl)-1,1,3,3-tetramethyluronium tetrafluoroborate (452 mg, 1.4 mmol) were dissolved in dichloromethane 25 mL) and dimethylformamide (5 mL). The reaction mixture was stirred at room temperature for 30 minutes. N²-Cycloheptyl-4H-benzo[d][1,3]oxazine-2,6-diamine (228 mg, 0.88 mmol) was added and stirring was continued overnight. The reaction mixture was diluted with water and thrice extracted with dichloromethane. The combined organic phases were dried over sodium sulfate and evaporated. The crude product was purified by column chromatography (silica gel, dichloromethane/methanol/ammonia 100:0:0–>110:10:1). The title compound (144 mg, 41%) was obtained as an off-white foam; MS: m/e=400.5 (M+H⁺).

EXAMPLE 94

N⁶-Benzyl-N²-cycloheptyl-4H-benzo[d][1,3]oxazine-2,6-diamine

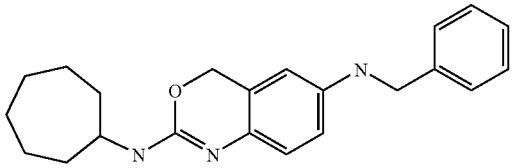

Prepared from N²-cycloheptyl-4H-benzo[d][1,3]oxazine-2,6-diamine (example 92) (200 mg, 0.77 mmol) and benzaldehyde (90 mg, 0.85 mmol) according to the procedure described for example 88. Obtained the title compound as a yellow oil (259 mg, 96%), MS (ISP) m/e=350.5 [(M+H)⁺].

EXAMPLE 95

Cyclopropanecarboxylic acid (2-cycloheptylamino-4H-benzo[d][1,3]oxazin-6-yl)-amide

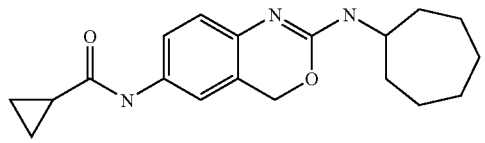

Prepared from N²-cycloheptyl-4H-benzo[d][1,3]oxazine-2,6-diamine (example 92) (200 mg, 0.77 mmol) and cyclopropanecarboxylic acid (80 mg, 0.93 mmol) according to the procedure described for example 93. Obtained the title compound as an off-white foam (104 mg, 41%), MS (ISP) m/e=328.4 [(M+H)⁺].

EXAMPLE 96

Cyclopropanecarboxylic acid [2-(2-phenoxy-ethylamino)-4H-benzo[d][1,3]oxazin-6-yl]-amide

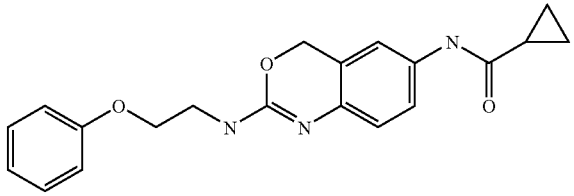

Prepared from N²-(2-phenoxy-ethyl)-4H-benzo[d][1,3]oxazine-2,6-diamine (Example 87) (142 mg, 0.50 mmol, HPLC 0.776 min) and cyclopropylcarbonyl chloride (53 ul, 0.55 mmol) according to the procedure described for Example 17. Obtained the title compound as a white solid (145 mg, 83%, HPLC 1.071 min), MS (ISP) m/e=352.2 [(M+H)⁺].

EXAMPLE 97

Cyclopropanesulfonic acid (2-cycloheptylamino-4H-benzo[d][1,3]oxazin-6-yl)-amide

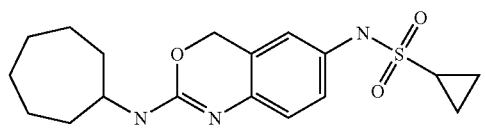

Prepared from N²-cycloheptyl-4H-benzo[d][1,3]oxazine-2,6-diamine (example 92) (200 mg, 0.77 mmol) and cyclopropylsulfonyl chloride (119 mg, 0.85 mmol) according to the procedure described for example 27. Obtained the title compound as a white solid (7 mg, 2.5%), MS (ISP) m/e=364.3 [(M+H)⁺].

EXAMPLE 98

N²-Cycloheptyl-N⁶-thiazol-2-ylmethyl-4H-benzo[d][1,3]oxazine-2,6-diamine

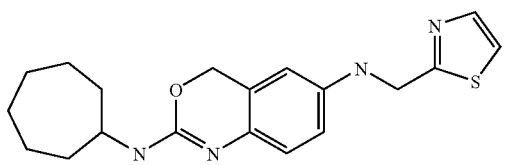

Prepared from N²-cycloheptyl-4H-benzo[d][1,3]oxazine-2,6-diamine (example 92) (188 mg, 0.73 mmol) and 2-formylthiazole (90 mg, 0.80 mmol) according to the procedure described for example 88. Obtained the title compound as a yellow foam (101 mg, 39%), MS (ISP) m/e=357.3 [(M+H)⁺].

EXAMPLE 99

N,N-(Dimethyl)-N'-{2-cycloheptylamino-4H-benzo[d][1,3]oxazin-6-yl-}-sulfamide

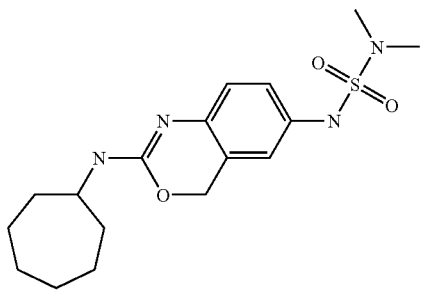

Prepared from N²-cycloheptyl-4H-benzo[d][1,3]oxazine-2,6-diamine (example 92) (200 mg, 0.77 mmol) and dimethylsulfamoyl chloride (122 mg, 0.85 mmol) according to the procedure described for example 27. Obtained the title compound as an off-white foam (105 mg, 37%), MS (ISP) m/e=365.5 [(M−H)⁺].

EXAMPLE 100

N-(2-Cycloheptylamino-4H-benzo[d][1,3]oxazin-6-yl)-benzenesulfonamide

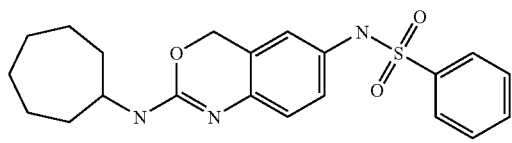

Prepared from N²-cycloheptyl-4H-benzo[d][1,3]oxazine-2,6-diamine (example 92) (200 mg, 0.77 mmol) and benzenesulfonyl chloride (136 mg, 0.77 mmol) according to the procedure described for example 27. Obtained the title compound as a white foam (17 mg, 5.5%), MS (ISP) m/e=400.3 [(M+H)⁺].

EXAMPLE 101

N²-(7-Methoxy-indan-1-yl)-N⁶-(5-methyl-[1,3,4]oxadiazol-2-yl)-4H-benzo[d][1,3]oxazine-2,6-diamine

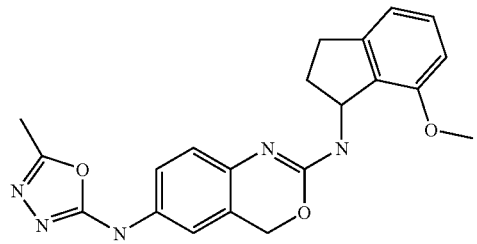

The title compound (67 mg, 34%), white solid, MS (ISP): m/e=392.2 (M+H⁺); m.p. 162° C., was prepared in accordance with the general method of Example 35 from rac-(6-bromo-4H-benzo[d][1,3]oxazin-2-yl)-(7-methoxy-indan-1-yl)-amine (Example 74) (187 mg, 0.5 mmol) and commercially available 5-methyl-1,3,4-oxadiazol-2-yl-amine (99 mg, 1.0 mmol).

EXAMPLE 102 rac-N-[2-(7-Methoxy-indan-1-ylamino)-4H-benzo[d][1,3]oxazin-6-yl]-methanesulfonamide

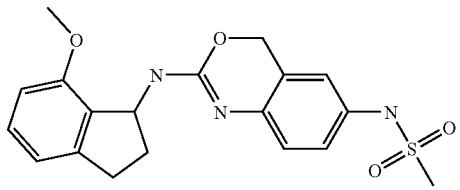

Prepared from rac-N²-(7-methoxy-indan-1-yl)-4H-benzo[d][1,3]oxazine-2,6-diamine (Example 10) (155 mg, 0.50 mmol, HPLC 0.776 min) and methanesulfonyl chloride (43 ul, 0.55 mmol) according to the procedure described for Example 27. Obtained the title compound as a light brown solid (84 mg, 43%, HPLC 1.178 min), MS (ISP) m/e=388.3 [(M+H)⁺].

EXAMPLE 103 rac-Cyclopropanesulfonic acid [2-(7-methoxy-indan-1-ylamino)-4H-benzo[d][1,3]oxazin-6-yl]-amide

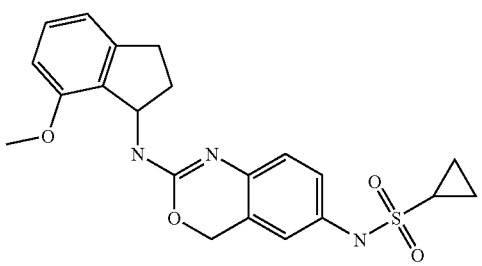

Prepared from rac-N$^2$-(7-methoxy-indan-1-yl)-4H-benzo[d][1,3]oxazine-2,6-diamine (Example 10) (155 mg, 0.50 mmol, HPLC 0.776 min) and cyclopropanesulfonyl chloride (77 mg, 0.55 mmol) according to the procedure described for Example 27. Obtained the title compound as a light brown solid (127 mg, 61%, HPLC 1.366 min), MS (ISP) m/e=414.2 [(M+H)$^+$].

EXAMPLE 104 rac-N-[2-(7-Methoxy-indan-1-ylamino)-4H-benzo[d][1,3]oxazin-6-yl]-benzenesulfonamide

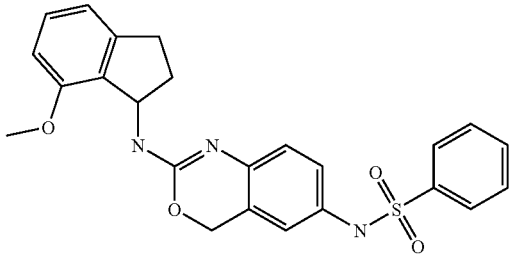

Prepared from rac-N$^2$-(7-methoxy-indan-1-yl)-4H-benzo[d][1,3]oxazine-2,6-diamine (Example 10) (155 mg, 0.50 mmol, HPLC 0.776 min) and benzenesulfonyl chloride (70 ul, 0.55 mmol) according to the procedure described for Example 27. Obtained the title compound as an off-white solid (58 mg, 26%, HPLC 1.576 min), MS (ISP) m/e=450.2 [(M+H)$^+$].

EXAMPLE 105

N$^2$-Cycloheptyl-N$^6$-(1H-imidazol-2-ylmethyl)-4H-benzo[d][1,3]oxazine-2,6-diamine Prepared from N$^2$-cycloheptyl-4H-benzo[d][1,3]oxazine-2,6-diamine (example 92) (150 mg, 0.58 mmol) and 2-formylimidazole (67 mg, 0.70 mmol) according to the procedure described for example 88. Obtained the title compound as an off-white foam (145 mg, 74%), MS (ISP) m/e=338.5 [(M−H)$^+$].

EXAMPLE 106 rac-N$^2$-(5-Fluoro-indan-1-yl)-N$^6$-(5-methyl-[1,3,4]oxadiazol-2-yl)-4H-benzo[d][1,3]oxazine-2,6-diamine The title compound (66 mg, 35%), off-white solid, MS (ISP): m/e=380.2 (M+H$^+$); m.p. 121° C., was prepared in accordance with the general method of Example 35 from rac-(6-bromo-4H-benzo[d][1,3]oxazin-2-yl)-(5-fluoro-indan-1-yl)-amine (Example 53) (181 mg, 0.5 mmol) and commercially available 5-methyl-1,3,4-oxadiazol-2-yl-amine (99 mg, 1.0 mmol).

EXAMPLE 107 rac-N$^2$-(4-Methoxy-2,3-dihydro-benzofuran-3-yl)-N$^6$-(5-methyl-[1,3,4]oxadiazol-2-yl)-4H-benzo[d][1,3]oxazine-2,6-diamine The title compound (84 mg, 43%), white solid, MS (ISP): m/e=393.1 (M+H$^+$); m.p. 191° C., was prepared in accordance with the general method of Example 35 from rac-(6-bromo-4H-benzo[d][1,3]oxazin-2-yl)-(4-methoxy-2,3-dihydro-benzofuran-3-yl)-amine (Example 54) (188 mg, 0.5 mmol) and commercially available 5-methyl-1,3,4-oxadiazol-2-yl-amine (99 mg, 1.0 mmol).

EXAMPLE 108

Cyclopropanesulfonic acid [2-(2-phenoxy-ethylamino)-4H-benzo[d][1,3]oxazin-6-yl]-amide Step A: (6-Nitro-4H-benzo[d][1,3]oxazin-2-yl)-(2-phenoxy-ethyl)-amine: Prepared from tert-butyl-(2-isothiocyanato-5-nitro-benzyloxy)-dimethyl-silane (Example C1) (2.0 g, 6 mmol) and phenoxyethylamine (807 mg, 6 mmol) according to the procedure described for Example 1. Obtained the title compound as a yellow solid (550 mg, 30%), MS (ISP) m/e=314.0 [(M+H)$^+$].

Step B: N$^2$-(2-Phenoxy-ethyl)-4H-benzo[d][1,3]oxazine-2,6-diamine: Prepared from the above described (6-nitro-4H-benzo[d][1,3]oxazin-2-yl)-(2-phenoxy-ethyl)-amine (550 mg, 1.76 mmol) according to the procedure described for Example 2 step B. Obtained the title compound as a light yellow foam (500 mg, 100%), MS (ISP) m/e=284.3 [(M+H)$^+$].

Step C: Cyclopropanesulfonic acid [2-(2-phenoxy-ethylamino)-4H-benzo[d][1,3]oxazin-6-yl]-amide: Prepared from the above described N$^2$-(2-phenoxy-ethyl)-4H-benzo[d][1,3]oxazine-2,6-diamine (155 mg, 0.50 mmol, HPLC 0.691 min) and cyclopropanesulfonyl chloride (77 mg, 0.55 mmol) according to the procedure described for Example 27. Obtained the title compound as an off-white foam (140 mg, 73%, HPLC 1.261 min), MS (ISP) m/e=388.3 [(M+H)+].

EXAMPLE 109

N-[2-(2-Phenoxy-ethylamino)-4H-benzo[d][1,3]oxazin-6-yl]-benzenesulfonamide

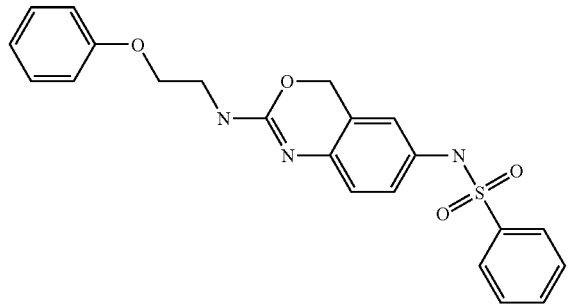

Prepared from N²-(2-phenoxy-ethyl)-4H-benzo[d][1,3]oxazine-2,6-diamine (Example 108, step B) (155 mg, 0.50 mmol, HPLC 0.691 min) and benzenesulfonyl chloride (70 ul, 0.55 mmol) according to the procedure described for Example 27. Obtained the title compound as an off-white foam (158 mg, 75%, HPLC 1.452 min), MS (ISP) m/e=424.1 [(M+H)+].

EXAMPLE 110

N,N-(Dimethyl)-N'-{2-(2-Phenoxy-ethylamino)-4H-benzo[d][1,3]oxazin-6-yl}-sulfamide Prepared from N²-(2-phenoxy-ethyl)-4H-benzo[d][1,3]oxazine-2,6-diamine (Example 108, step B) (155 mg, 0.50 mmol, HPLC 0.691 min) and dimethylsulfamoyl chloride (59 ul, 0.55 mmol) according to the procedure described for Example 27. Obtained the title compound as an off-white foam (140 mg, 72%, HPLC 1.127 min), MS (ISP) m/e=391.2 [(M+H)+].

EXAMPLE 111 rac-N⁶-(5-Cyclopropyl-[1,3,4]oxadiazol-2-yl)-N²-(7-methoxy-indan-1-yl)-4H-benzo[d][1,3]oxazine-2,6-diamine The title compound (82 mg, 39%), white solid, MS (ISP): m/e=418.2 (M+H+); m.p. 204° C., was prepared in accordance with the general method of Example 35 from rac-(6-bromo-4H-benzo[d][1,3]oxazin-2-yl)-(7-methoxy-indan-1-yl)-amine (Example 74) (187 mg, 0.5 mmol) and commercially available 5-cyclopropyl-1,3,4-oxadiazol-2-yl-amine (125 mg, 1.0 mmol).

EXAMPLE 112 rac-N⁶-(2-tert-Butyl-2H-tetrazol-5-yl)-N²-(7-methoxy-indan-1-yl)-4H-benzo[d][1,3]oxazine-2,6-diamine The title compound (34 mg, 16%), off-white foam, MS (ISP): m/e=434.4 (M+H+), was prepared in accordance with the general method of Example 35 from rac-(6-bromo-4H-benzo[d][1,3]oxazin-2-yl)-(7-methoxy-indan-1-yl)-amine (Example 74) (187 mg, 0.5 mmol) and commercially available 2-tert.-butyl-2H-tetrazole-5-yl-amine (141 mg, 1.0 mmol).

EXAMPLE 113 rac-Cyclopropanesulfonic acid [2-(4-methoxy-2,3-dihydro-benzofuran-3-ylamino)-4H-benzo[d][1,3]oxazin-6-yl]-amide Prepared from rac-N²-(4-methoxy-2,3-dihydro-benzofuran-3-yl)-4H-benzo[d][1,3]oxazine-2,6-diamine (Example 6) (150 mg, 0.482 mmol) and cyclopropanesulfonyl chloride (75 mg, 0.53 mmol) according to the procedure described for Example 27. Obtained the title compound as an off-white solid (85 mg, 43%), MS (ISP) m/e=416.1 [(M+H)⁺].

EXAMPLE 114 rac-N-[2-(4-Methoxy-2,3-dihydro-benzofuran-3-ylamino)-4H-benzo[d][1,3]oxazin-6-yl]-methanesulfonamide

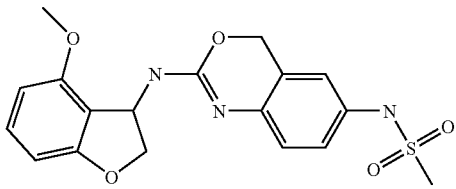

Prepared from rac-N²-(4-methoxy-2,3-dihydro-benzofuran-3-yl)-4H-benzo[d][1,3]oxazine-2,6-diamine (Example 6) (150 mg, 0.482 mmol) and methanesulfonyl chloride (61 mg, 0.53 mmol) according to the procedure described for Example 27. Obtained the title compound as a white solid (80 mg, 43%), MS (ISP) m/e=390.1 [(M+H)⁺].

EXAMPLE 115 rac-N-[2-(4-Methoxy-2,3-dihydro-benzofuran-3-ylamino)-4H-benzo[d][1,3]oxazin-6-yl]-benzenesulfonamide

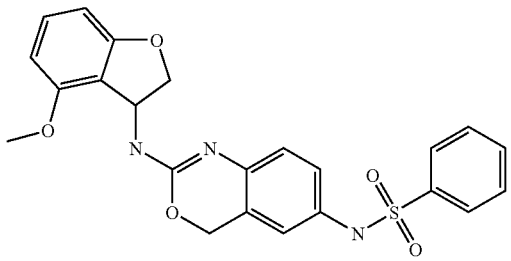

Prepared from rac-N²-(4-methoxy-2,3-dihydro-benzofuran-3-yl)-4H-benzo[d][1,3]oxazine-2,6-diamine (Example 6) (150 mg, 0.482 mmol) and benzenesulfonyl chloride (94 mg, 0.53 mmol) according to the procedure described for Example 27. Obtained the title compound as a white solid (120 mg, 55%), MS (ISP) m/e=452.3 [(M+H)⁺].

EXAMPLE 116

2-(3-Hydroxymethyl-4-methyl-piperazin-1-yl)-N-[2-(7-methoxy-indan-1-ylamino)-4H-benzo[d][1,3]oxazin-6-yl]-acetamide

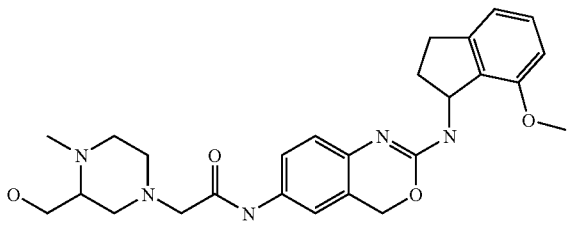

Prepared from rac-2-chloro-N-[2-(7-methoxy-indan-1-ylamino)-4H-benzo[d][1,3]oxazin-6-yl]-acetamide (Example 55, step A) (150 mg, 0.39 mmol), commercially available rac-(1-methyl-piperazin-2-yl)-methanol (CAS no. 141108-61-4) (76 mg, 0.58 mmol) and diisopropylethyl amine (198 ul, 1.17 mmol) in acetonitrile (5 ml) according to the procedure described for Example 3 step B. Obtained the title compound as a white solid (125 mg, 67%), MS (ISP) m/e=480.2 [(M+H)⁺].

EXAMPLE 117

2-((R)-Indan-1-ylamino)-4H-benzo[d][1,3]oxazine-6-carbonitrile

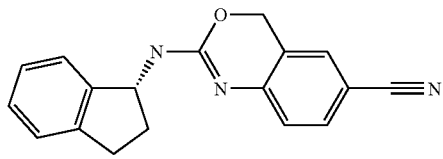

A stirred mixture of (6-bromo-4H-benzo[d][1,3]oxazin-2-yl)-(R)-indan-1-yl-amine (Example 32) (2.0 g, 5.83 mmol), zink cyanide (1.03 mg, 8.77 mmol) and tetrakis-(triphenylphosphine)-palladium (673 mg, 0.58 mmol) in N,N-dimethylformamide (20 ml) was heated at 160° C. for 15 min in a microwave reactor. The reaction mixture was poured into water (50 ml) and extracted with ethyl acetate (2×70 ml). The combined organic layers were washed with brine (2×20 ml), dried (magnesium sulfate) and evaporated. The crude product was purified by flash chromatography (ethyl acetate/heptane) on silica gel to yield the title compound as light yellow foam (693 mg, 41%). MS (ISN): m/e=288.2 (M−H⁻).

EXAMPLE 118

N²—(R)-Indan-1-yl-N⁶-(5-methyl-[1,3,4]oxadiazol-2-yl)-4H-benzo[d][1,3]oxazine-2,6-diamine

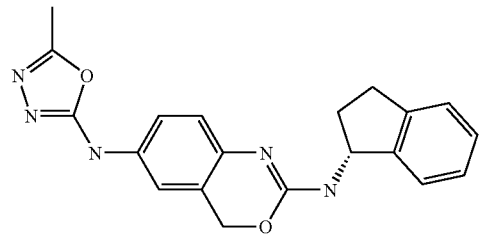

The title compound (67 mg, 37%), off-white solid, MS (ISP): m/e=362.2 (M+H⁺); m.p. 137° C., was prepared in accordance with the general method of Example 35 from (6-bromo-4H-benzo[d][1,3]oxazin-2-yl)-(R)-indan-1-yl-amine (Example 32) (172 mg, 0.5 mmol) and commercially available 5-methyl-1,3,4-oxadiazol-2-yl-amine (99 mg, 1.0 mmol).

EXAMPLE 119

N²-(3-Cyclopropyl-phenyl)-4H-benzo[d][1,3]ox-azine-2,6-diamine

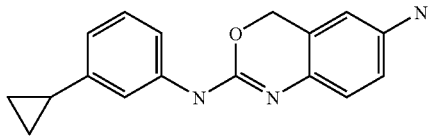

Step A: (3-Cyclopropyl-phenyl)-(6-nitro-4H-benzo[d][1,3]oxazin-2-yl)-amine: Prepared from tert-butyl-(2-isothiocyanato-5-nitro-benzyloxy)-dimethyl-silane (Example C1) (5.8 g, 18 mmol) and 3-cyclopropyl-phenylamine (2.5 g, 19 mmol) according to the procedure described for Example 1. Obtained the title compound as a yellow foam (4.1 g, 74%), MS (ISP) m/e=310.5 [(M+H)⁺].

Step B: N²-(3-Cyclopropyl-phenyl)-4H-benzo[d][1,3]oxazine-2,6-diamine: Prepared from the above described cyclo-heptyl-(6-nitro-4H-benzo[d][1,3]oxazin-2-yl)-amine (4.0 g, 13 mmol) according to the procedure described for Example 2 step B. Obtained the title compound as a light yellow foam (32 g, 88%), MS (ISP) m/e=280.1 [(M+H)⁺].

EXAMPLE 120 rac-N-[2-(Chroman-4-ylamino)-4H-benzo[d][1,3]oxazin-6-yl]-2-(4-methyl-piperazin-1-yl)-acetamide

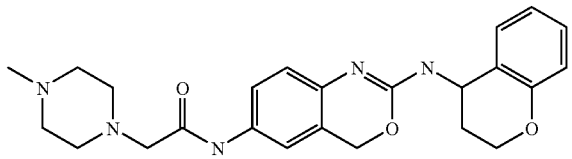

Step A: rac-2-Chloro-N-[2-(chroman-4-ylamino)-4H-benzo[d][1,3]oxazin-6-yl]-acetamide: Prepared from rac-N²-chroman-4-yl-4H-benzo[d][1,3]oxazine-2,6-diamine (Example 75) (591 mg, 2.0 mmol) and chloroacetyl chloride (167 ul, 2.1 mmol) according to the procedure described for Example 3 step A. Obtained the title compound as an off-white solid (618 mg, 83%), MS (ISP) m/e=372.1 [(M+H)⁺] and 374 [(M+2+H)⁺].

Step B: rac-N-[2-(Chroman-4-ylamino)-4H-benzo[d][1,3]oxazin-6-yl]-2-(4-methyl-piperazin-1-yl)-acetamide: Prepared from the above described rac-2-chloro-N-[2-(chroman-4-ylamino)-4H-benzo[d][1,3]oxazin-6-yl]-acetamide (186 mg, 0.50 mmol; HPLC 1.092 min) and 1-methylpiperazine (1.1 ml, 10 mmol) according to the procedure described for Example 3 step B. Obtained the title compound as a white solid (218 mg, 100%; HPLC 0.413 min), MS (ISP) m/e=436.1 [(M+H)⁺].

EXAMPLE 121

N-[2-(Chroman-4-ylamino)-4H-benzo[d][1,3]oxazin-6-yl]-2-morpholin-4-yl-acetamide

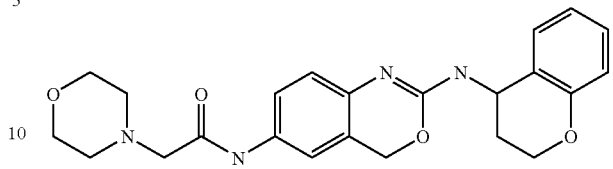

Prepared from rac-2-chloro-N-[2-(chroman-4-ylamino)-4H-benzo[d][1,3]oxazin-6-yl]-acetamide (Example 120, step A) (186 mg, 0.50 mmol; HPLC 1.092 min) and morpholine (0.87 ml, 10 mmol) according to the procedure described for Example 3 step B. Obtained the title compound as a white foam (217 mg, 100%; HPLC 0.504 min), MS (ISP) m/e=423.2 [(M+H)⁺].

EXAMPLE 122

2-(4-Methyl-piperazin-1-yl)-N-[2-(2-phenoxy-ethylamino)-4H-benzo[d][1,3]oxazin-6-yl]-acetamide

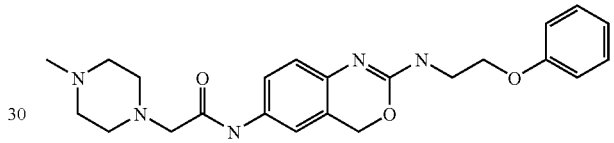

Step A: 2-Chloro-N-[2-(2-phenoxy-ethylamino)-4H-benzo[d][1,3]oxazin-6-yl]-acetamide: Prepared from N²-(2-phenoxy-ethyl)-4H-benzo[d][1,3]oxazine-2,6-diamine (Example 87) (591 mg, 2.0 mmol) and chloroacetyl chloride (167 ul, 2.1 mmol) according to the procedure described for Example 3 step A. Obtained the title compound as an off-white solid (585 mg, 81%), MS (ISP) m/e=360.1 [(M+H)⁺] and 362 [(M+2+H)⁺].

Step B: 2-(4-Methyl-piperazin-1-yl)-N-[2-(2-phenoxy-ethylamino)-4H-benzo[d][1,3]oxazin-6-yl]-acetamide: Prepared from the above described 2-chloro-N-[2-(2-phenoxy-ethylamino)-4H-benzo[d][1,3]oxazin-6-yl]-acetamide (180 mg, 0.50 mmol; HPLC 1.096 min) and 1-methylpiperazine (1.1 ml, 10 mmol) according to the procedure described for Example 3 step B. Obtained the title compound as a white foam (214 mg, 100%; HPLC 0.494 min), MS (ISP) m/e=424.1 [(M+H)⁺].

EXAMPLE 123

2-Morpholin-4-yl-N-[2-(2-phenoxy-ethylamino)-4H-benzo[d][1,3]oxazin-6-yl]-acetamide

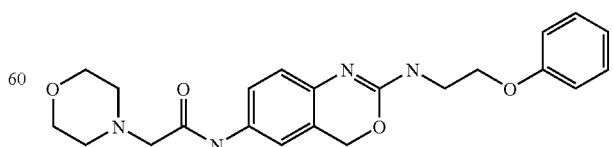

Prepared from 2-chloro-N-[2-(2-phenoxy-ethylamino)-4H-benzo[d][1,3]oxazin-6-yl]-acetamide (Example 122, step A) (180 mg, 0.50 mmol; HPLC 1.096 min) and morpholine (0.87 ml, 10 mmol) according to the procedure described for Example 3 step B. Obtained the title compound as a white solid (206 mg, 100%; HPLC 0.588 min), MS (ISP) m/e=411.2 [(M+H)$^+$].

EXAMPLE 124

1-(2-Cycloheptylamino-4H-benzo[d][1,3]oxazin-6-yl)-3-(1-isopropyl-piperidin-4-yl)-urea

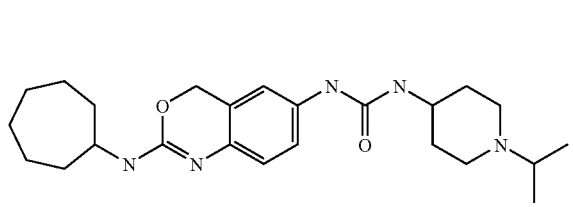

Prepared from N$^2$-cycloheptyl-4H-benzo[d][1,3]oxazine-2,6-diamine and N-isopropyl-4-aminopiperidine according to the procedure described for example 14. Obtained the title compound as a white solid, MS (ISP) m/e=428.4 [(M+H)$^+$].

EXAMPLE 125

N$^2$-(3-Cyclopropyl-phenyl)-N$^6$-(1H-imdazol-2-ylmethyl)-4H-benzo[d][1,3]oxazine-2,6-diamine

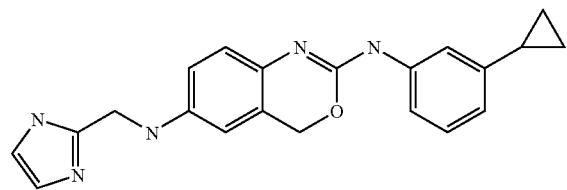

Prepared from N$^2$-(3-cyclopropyl-phenyl)-4H-benzo[d][1,3]oxazine-2,6-diamine (197 mg, 0.71 mmol) and 2-formylimidazole (81 mg, 0.84 mmol) according to the procedure described for example 88. Obtained the title compound as a white solid (100 mg, 39%), MS (ISP) m/e=358.5 [(M−H)$^+$].

EXAMPLE 126

N-[2-(3-Cyclopropyl-phenylamino)-4H-benzo[d][1,3]oxazin-6-yl]-2-(4-methyl-piperazin-1-yl)-acetamide

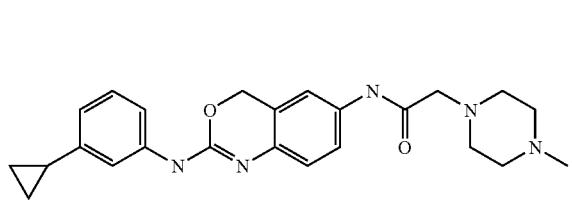

Prepared from N$^2$-(3-cyclopropyl-phenyl)-4H-benzo[d][1,3]oxazine-2,6-diamine (160 mg, 0.57 mmol) and 4-methylpiperazin-1-acetic acid (109 mg, 0.69 mmol) according to the procedure described for example 93. Obtained the title compound as an off-white solid (60 mg, 25%), MS (ISP) m/e=420.3 [(M+H)$^+$].

EXAMPLE 127

N$^2$-(3-Cyclopropyl-phenyl)-N$^6$-thiazol-2-ylmethyl-4H-benzo[d][1,3]oxazine-2,6-diamine

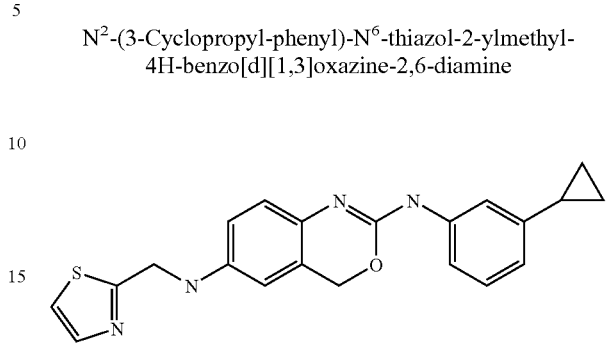

Prepared from N$^2$-(3-cyclopropyl-phenyl)-4H-benzo[d][1,3]oxazine-2,6-diamine (158 mg, 0.57 mmol) and 2-formylthiazole (70 mg, 0.62 mmol) according to the procedure described for example 88. Obtained the title compound as a yellow foam (99 mg, 46%), MS (ISP) m/e=377.2 [(M−H)$^+$].

EXAMPLE 128

Cyclopropanecarboxylic acid [2-(3-cyclopropyl-phenylamino)-4H-benzo[d][1,3]oxazin-6-yl]-amide

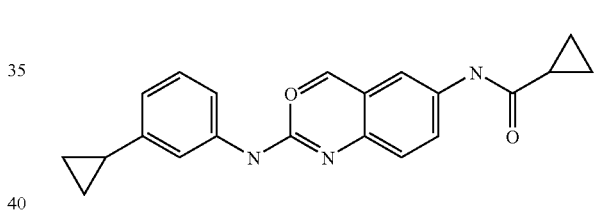

Prepared from N$^2$-(3-cyclopropyl-phenyl)-4H-benzo[d][1,3]oxazine-2,6-diamine (200 mg, 0.72 mmol) and and cyclopropane carboxylic acid (80 mg, 0.93 mmol) according to the procedure described for example 93. Obtained the title compound as a white solid (93 mg, 37%), MS (ISP) m/e=348.3 [(M+H)$^+$].

EXAMPLE 129

(6-Aminomethyl-4H-benzo[d][1,3]oxazin-2-yl)-(R)-indan-1-yl-amine

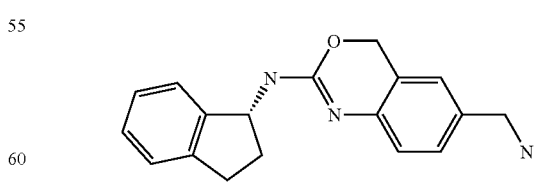

Hydrogenation of 2-((R)-indan-1-ylamino)-4H-benzo[d][1,3]oxazine-6-carbonitrile (example 117) (310 mg, 1.07 mmol) dissolved in methanol (15 ml) and 7N methanol-NH$_3$ (7.5 ml) on Ra—Ni (310 mg) for 17 h at room temperature yielded after removal of the catalyst by filtration and evaporation a yellow oil which was further purified by column chromatography (dichloromethane/methanol/ammonium hydroxide 15:1:0.1) on silica gel to yield the title compound as colorless oil (254 mg, 81%). MS (ISP): m/e=294.2 (M+H$^+$).

EXAMPLE 130

N-Hydroxy-2-((R)-indan-1-ylamino)-4H-benzo[d][1,3]oxazine-6-carboxamidine

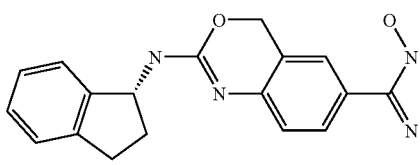

A stirred suspension of 2-((R)-indan-1-ylamino)-4H-benzo[d][1,3]oxazine-6-carbonitrile (example 117) (310 mg, 1.07 mmol), hydroxylamine hydrochloride (275 mg, 3.96 mmol), sodium carbonate (227 mg, 2.14 mmol) in ethanol (4 ml) and water (4 ml) was heated under reflux conditions for 17 h, water (10 ml) was added, the precipitate was collected by filtration, washed with water and hexane. The crude product was further purified by crystallization (diethyl ether/methanol 10:1) to yield the title compound as white solid (280 mg, 81%). MS (ISP): m/e=323.3 (M+H$^+$); m.p. 206° C.

EXAMPLE 131

N$^2$-(2,2-Dimethyl-2,3-dihydro-benzofuran-7-yl)-N$^6$-(1H-imidazol-2-ylmethyl)-4H-benzo[d][1,3]oxazine-2,6-diamine

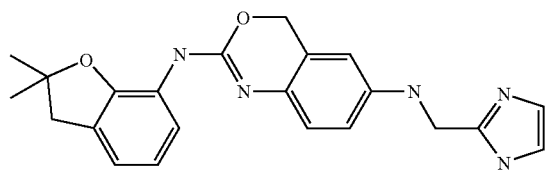

Prepared from N$^2$-(2,2-dimethyl-2,3-dihydro-benzofuran-7-yl)-4H-benzo[d][1,3]oxazine-2,6-diamine (example 139, step B) and 2-imidazolecarboxaldehyde according to the procedure described for example 88. The title compound was obtained as a brown solid, MS (ISP) m/e=390.3 [(M+H)$^+$].

EXAMPLE 132

4-Fluoro-N-[2-((R)-indan-1-ylamino)-4H-benzo[d][1,3]oxazin-6-ylmethyl]-benzamide

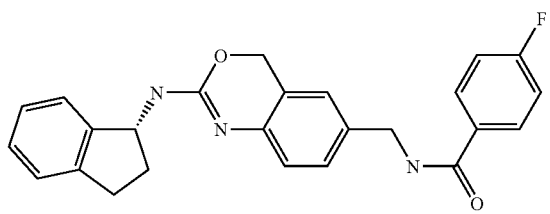

To a cooled (ice bath) and stirred solution of (6-aminomethyl-4H-benzo[d][1,3]oxazin-2-yl)-(R)-indan-1-yl-amine (example 129) (200 mg, 0.68 mmol) and triethylamine (76 mg, 0.75 mmol) in tetrahydrofuran (4 ml) was added 4-fluorobenzoyl chloride (119 mg, 0.75 mmol) and the mixture was allowed to stir at 0° C. for 1 h and afterwards at room temperature for 16 h. The reaction mixture was poured into water (15 ml) and extracted with ethyl acetate (2×20 ml). The combined organic layers were washed with brine (20 ml), dried (magnesium sulfate) and evaporated. The crude product was purified by flash chromatography (ethyl acetate/heptane) on silica gel to yield the title compound as white foam (191 mg, 67%). MS (ISP): m/e=416.3 (M+H$^+$).

EXAMPLE 133

(R)-Indan-1-yl-[6-(5-methyl-[1,2,4]oxadiazol-3-yl)-4H-benzo[d][1,3]oxazin-2-yl]-amine

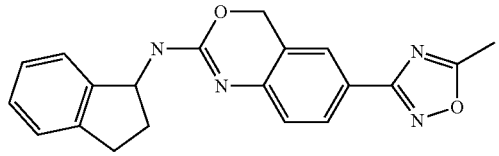

To a stirred solution of acetic acid (67 mg, 1.12 mmol) in tetrahydrofuran (7.5 ml) was added at room temperature 1,1'-carbonyl-diimidazole (193 mg, 1.19 mmol). The mixture was allowed to stir for 15 min at room temperature and afterwards for 90 min at 70° C. N-hydroxy-2-((R)-indan-1-ylamino)-4H-benzo[d][1,3]oxazine-6-carboxamidine (Example 130) (240 mg, 0.74 mmol) was added at room temperature. The mixture was allowed to stir for 1 h at room temperature, evaporated to dryness and diluted with acetic acid (10 ml). The reaction mixture was allowed to stir for 2 h at 100° C., evaporated, poured into saturated sodium hydrogen carbonate solution (20 ml) and extracted with ethyl acetate (2×30 ml). The combined organic layers were washed with brine (1×20 ml), dried (magnesium sulfate) and evaporated. The crude product was purified by flash chromatography (ethyl acetate/heptane) on silica gel and crystallization (dichloromethane/hexane) to yield the title compound as white solid (137 mg, 53%). MS (ISP): m/e=347.1 (M+H$^+$); m.p. 138° C.

EXAMPLE 134

(R)-Indan-1-yl-(6-vinyl-4H-benzo[d][1,3]oxazin-2-yl)-amine

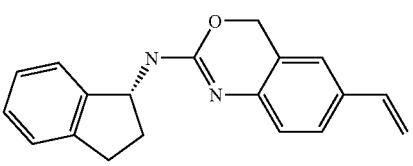

A stirred mixture of (6-bromo-4H-benzo[d][1,3]oxazin-2-yl)-(R)-indan-1-yl-amine (Example 32) (1.03 g, 3.0 mmol), tributyl-(vinyl)-stannane (0.98 g, 3 mmol) and tetrakis-(triphenylphosphine)-palladium (0.07 g, 0.06 mmol) in toluene (30 ml) was heated under reflux conditions for 3 h, evaporated and purified by chromatography (ethyl acetate/heptane) on silica gel to yield the title compound as colorless oil (526 mg, 60%). MS (ISP): m/e=291.2 (M+H$^+$).

EXAMPLE 135

N'-{2-[(3-cyclopropylphenyl)amino]-4H-benzo[d][1,3]oxazin-6-yl}-N,N-dimethylsulfamide

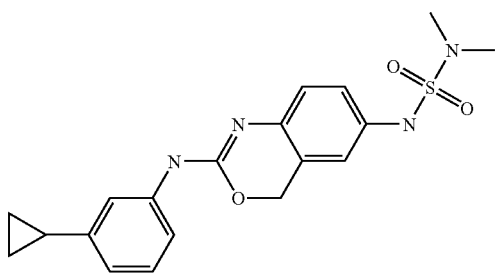

Prepared from N²-(3-cyclopropyl-phenyl)-4H-benzo[d][1,3]oxazine-2,6-diamine (200 mg, 0.72 mmol) and dimethylsulfamoyl chloride (122 mg, 0.85 mmol) according to the procedure described for example 27. Obtained the title compound as an off-white foam (104 mg, 37%), MS (ISP) m/e=385.3 [(M−H)⁺].

EXAMPLE 136

N⁶-Benzyl-N²-(3-cyclopropyl-phenyl)-4H-benzo[d][1,3]oxazine-2,6-diamine

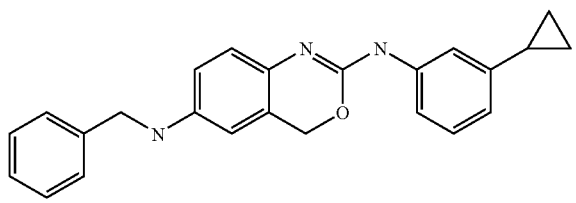

Prepared from N²-(3-cyclopropyl-phenyl)-4H-benzo[d][1,3]oxazine-2,6-diamine (200 mg, 0.72 mmol) and benzaldehyde (68 mg, 0.66 mmol) according to the procedure described for example 88. Obtained the title compound as a white foam (134 mg, 67%), MS (ISP) m/e=370.1 [(M+H)⁺].

EXAMPLE 137

1-[2-(3-Cyclopropyl-phenylamino)-4H-benzo[d][1,3]oxazin-6-yl]-3-(1-isopropyl-piperidin-4-yl)-urea

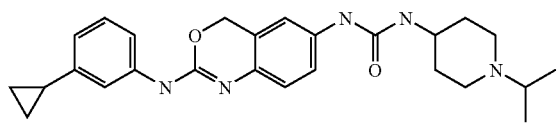

Prepared from N²-(3-cyclopropyl-phenyl)-4H-benzo[d][1,3]oxazine-2,6-diamine and N-isopropyl-4-aminopiperidine according to the procedure described for example 14. Obtained the title compound as a white solid, MS (ISP) m/e=448.3 [(M+H)⁺].

EXAMPLE 138

N²—(R)-Indan-1-yl-N⁶-(5-trifluoromethyl-[1,3,4]oxadiazol-2-yl)-4H-benzo[d][1,3]oxazine-2,6-diamine

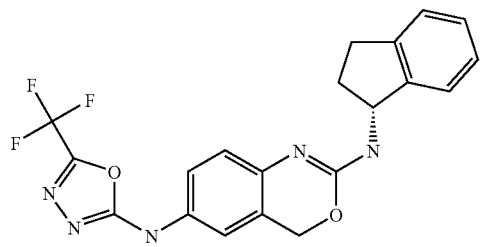

The title compound (88 mg, 42%), light yellow solid, MS (ISP): m/e=416.2 (M+H⁺); m.p. 155° C., was prepared in accordance with the general method of Example 35 from (6-bromo-4H-benzo[d][1,3]oxazin-2-yl)-(R)-indan-1-yl-amine (Example 32) (172 mg, 0.5 mmol) and commercially available 5-trifluoromethyl-1,3,4-oxadiazol-2-yl-amine (153 mg, 1.0 mmol).

EXAMPLE 139

1-[2-(2,2-Dimethyl-2,3-dihydro-benzofuran-7-ylamino)-4H-benzo[d][1,3]oxazin-6-yl]-isopropyl-urea

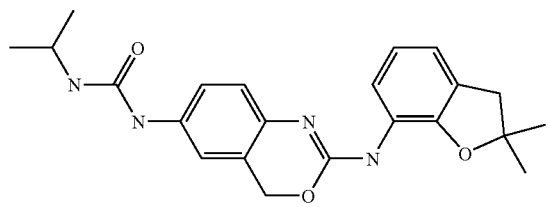

Step A: (2,2-Dimethyl-2,3-dihydro-benzofuran-7-yl)-(6-nitro-4H-benzo[d][1,3]oxazin-2-yl)-amine: Prepared from tert-butyl-(2-isothiocyanato-5-nitro-benzyloxy)-dimethyl-silane (Example C1) (3.75 g, 11 mmol) and 7-amino-2,3-dihydro-2,2-dimethylbenzofuran (CAS 68298-46-4) (1.86 g, 11 mmol) according to the procedure described for Example 1. Obtained the title compound as a yellow solid (2.5 g, 65%), MS (ISP) m/e=340.3 [(M+H)⁺].

Step B: N²-(2,2-Dimethyl-2,3-dihydro-benzofuran-7-yl)-4H-benzo[d][1,3]oxazine-2,6-diamine: Prepared from the above described (2,2-dimethyl-2,3-dihydro-benzofuran-7-yl)-(6-nitro-4H-benzo[d][1,3]oxazin-2-yl)-amine (2.43 g, 7.2 mmol) according to the procedure described for Example 2 step B. Obtained the title compound as a yellow solid (2.0 g, 91%), MS (ISP) m/e=310.1 [(M+H)⁺].

Step C: 1-[2-(2,2-Dimethyl-2,3-dihydro-benzofuran-7-ylamino)-4H-benzo[d][1,3]oxazin-6-yl]-3-isopropyl-urea: Prepared from the above described N²-(2,2-dimethyl-2,3-dihydro-benzofuran-7-yl)-4H-benzo[d][1,3]oxazine-2,6-diamine (150 mg, 0.49 mmol) and isopropyl isocyanate (42 mg, 0.49 mmol) according to the procedure described for Example 16. Obtained the title compound as a white solid (131 mg, 68%), MS (ISP) m/e=395.3 [(M+H)⁺].

EXAMPLE 140

(R)-Indan-1-yl-[6-((E)-styryl)-4H-benzo[d][1,3]ox-azin-2-yl]-amine

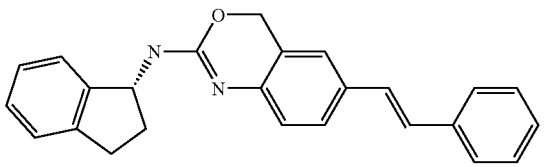

A stirred mixture of (6-bromo-4H-benzo[d][1,3]oxazin-2-yl)-(R)-indan-1-yl-amine (Example 32) (200 mg, 0.58 mmol), styrene (91 mg, 0.87 mmol), tri(o-tolyl)phosphine (14.2 mg, 0.047 mmol), triethylamine (295 mg, 2.91 mmol) and palladium actetate (5.23 mg, 0.023 mmol) in acetonitrile (5 ml) was heated under reflux conditions for 23 h, evaporated and purified by flash chromatography (ethyl acetate/heptane) on silica gel and crystallization (dichloromethane/heptane) to yield the title compound as white solid (34 mg, 16%). MS (ISP): m/e=367.2 (M+H⁺); m.p. 162° C.

EXAMPLE 141 rac-2-(4-Methoxy-2,3-dihydro-benzofuran-3-ylamino)-4H-benzo[d][1,3]oxazine-6-carbonitrile

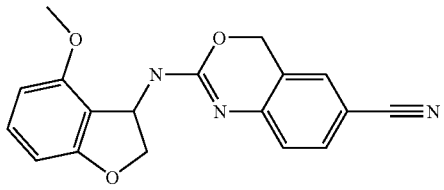

The title compound (40 mg, 31%), white foam, MS (ISN): m/e=320.2 (M−H⁻), was prepared in accordance with the general method of Example 117 from rac-(6-bromo-4H-benzo[d][1,3]oxazin-2-yl)-(4-methoxy-2,3-dihydro-benzofuran-3-yl)-amine (Example 54) (150 mg, 0.4 mmol).

EXAMPLE 142 rac-2-(7-Methoxy-indan-1-ylamino)-4H-benzo[d][1,3]oxazine-6-carbonitrile

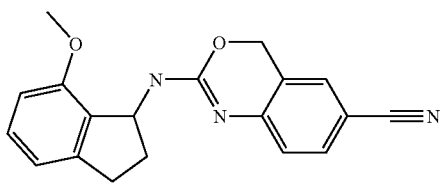

The title compound (38 mg, 30%), white foam, MS (ISP): m/e=318.2 (M−H⁻), was prepared in accordance with the general method of Example 117 from rac-(6-bromo-4H-benzo[d][1,3]oxazin-2-yl)-(7-methoxy-indan-1-yl)-amine (Example 74) (150 mg, 0.4 mm

EXAMPLE 143

(R)-Indan-1-yl-[6-((E)-2-pyridin-3-yl-vinyl)-4H-benzo[d][1,3]oxazin-2-yl]-amine

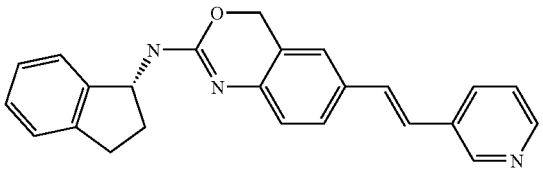

A stirred mixture of (R)-indan-1-yl-(6-vinyl-4H-benzo[d][1,3]oxazin-2-yl)-amine (Example 134) (250 mg, 0.86 mmol), 3-bromopyridine (177 mg, 1.12 mmol), tri(o-tolyl)phosphine (21 mg, 0.07 mmol), triethylamine (261 mg, 2.58 mmol) and palladium actetate (7.73 mg, 0.034 mmol) in N,N-dimethylformamide (3 ml) was heated in a sealed tube at 100° C. for 3 h. The reaction mixture was poured into water (20 ml), extracted with ethyl acetate (2×40 ml). The combined organic layers were washed with water (2×20 ml) and brine (20 ml), dried (magnesium sulfate) and evaporated. Further purification by flash chromatography (ethyl acetate/heptane) on silica gel and crystallization (dichloromethane/heptane) yielded the title compound as yellow solid (70 mg, 22%). MS (ISP): m/e=368.2 (M+H⁺); m.p. 132° C.

EXAMPLE 144 rac-N²-(7-Methoxy-indan-1-yl)-N⁶-(5-trifluoromethyl-[1,3,4]oxadiazol-2-yl)-4H-benzo[d][1,3]oxazine-2,6-diamine

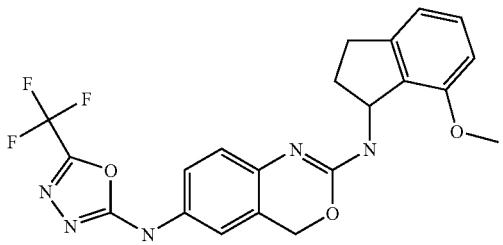

The title compound (96 mg, 43%), white solid, MS (ISP): m/e=446.2 (M+H⁺); m.p. 173° C., was prepared in accordance with the general method of Example 35 from rac-(6-bromo-4H-benzo[d][1,3]oxazin-2-yl)-(7-methoxy-indan-1-yl)-amine (Example 74) (187 mg, 0.5 mmol) and commercially available 5-trifluoromethyl-1,3,4-oxadiazol-2-yl-amine (153 mg, 1.0 mmol).

EXAMPLE 145 rac-N²-(4-Methoxy-2,3-dihydro-benzofuran-3-yl)-N⁶-(5-trifluoromethyl-[1,3,4]oxadiazol-2-yl)-4H-benzo[d][1,3]oxazine-2,6-diamine

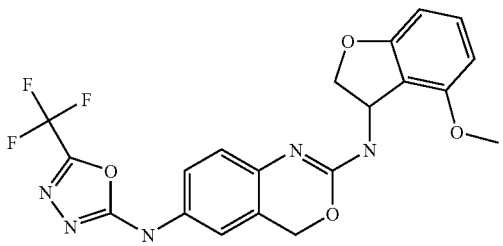

The title compound (38 mg, 17%), light yellow solid, MS (ISP): m/e=448.1 (M+H⁺); m.p. 212° C., was prepared in accordance with the general method of Example 35 from rac-(6-bromo-4H-benzo[d][1,3]oxazin-2-yl)-(4-methoxy-2,3-dihydro-benzofuran-3-yl)-amine (Example 54) (188 mg, 0.5 mmol) and commercially available 5-trifluoromethyl-1,3,4-oxadiazol-2-yl-amine (153 mg, 1.0 mmol).

EXAMPLE 146

N-[2-(7-Methoxy-indan-1-ylamino)-4H-benzo[d][1,3]oxazin-6-yl]-2-(3-methoxymethyl-4-methyl-piperazin-1-yl)-acetamide

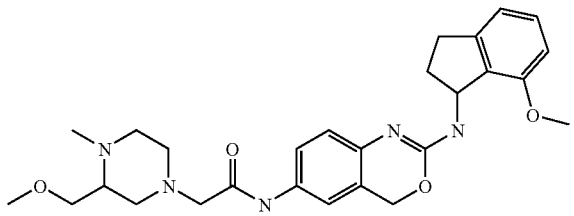

Prepared from rac-2-chloro-N-[2-(7-methoxy-indan-1-ylamino)-4H-benzo[d][1,3]oxazin-6-yl]-acetamide (Example 55, step A) (328 mg, 0.85 mmol), commercially available rac-2-methoxymethyl-1-methyl-piperazine (CAS no. 734507-92-7) (123 mg, 0.85 mmol) and diisopropylethyl amine (723 ul, 4.25 mmol) in acetonitrile (2 ml) according to the procedure described for Example 3 step B. Obtained the title compound as a white foam (137 mg, 33%), MS (ISP) m/e=494.3 [(M+H)⁺].

EXAMPLE 147

N-[2-((R)-Indan-1-ylamino)-4H-benzo[d][1,3]oxazin-6-yl]-2-(3-methoxymethyl-4-methyl-piperazin-1-yl)-acetamide

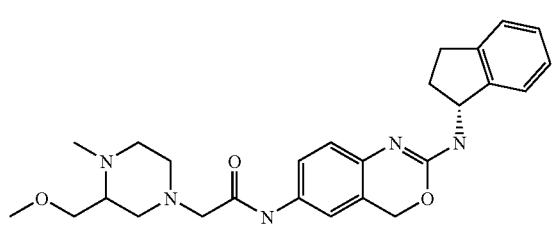

Prepared from 2-chloro-N-[2-((R)-indan-1-ylamino)-4H-benzo[d][1,3]oxazin-6-yl]-acetamide (Example 3, step A) (70 mg, 0.197 mmol), commercially available rac-2-methoxymethyl-1-methyl-piperazine (CAS no. 734507-92-7) (28.5 mg, 0.197 mmol) and diisopropylethyl amine (167 ul, 0.984 mmol) in acetonitrile (2 ml) according to the procedure described for Example 3 step B. Obtained the title compound as a light yellow (50 mg, 55%), MS (ISP) m/e=464.3 [(M+H)⁺].

EXAMPLE 148 rac-N²-(5-Fluoro-indan-1-yl)-N⁶-(5-trifluoromethyl-[1,3,4]oxadiazol-2-yl)-4H-benzo[d][1,3]oxazine-2,6-diamine

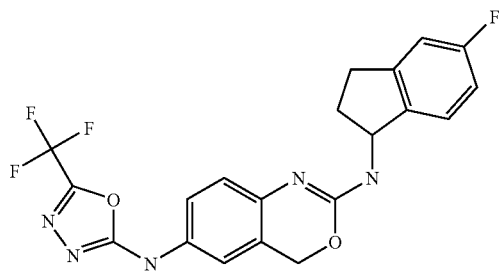

The title compound (82 mg, 38%), off-white solid, MS (ISP): m/e=434.3 (M+H⁺); m.p. 142° C., was prepared in accordance with the general method of Example 35 from rac-(6-bromo-4H-benzo[d][1,3]oxazin-2-yl)-(5-fluoro-indan-1-yl)-amine (Example 53) (181 mg, 0.5 mmol) and commercially available 5-trifluoromethyl-1,3,4-oxadiazol-2-yl-amine (153 mg, 1.0 mmol).

EXAMPLE 149

Cyclopropanesulfonic acid [2-(3-cyclopropyl-phenylamino)-4H-benzo[d][1,3]oxazin-6-yl]-amide

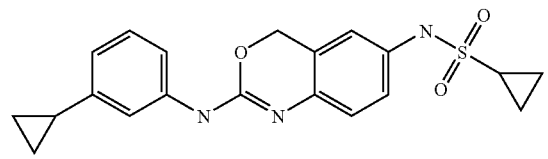

Prepared from N²-(3-Cyclopropyl-phenyl)-4H-benzo[d][1,3]oxazine-2,6-diamine (Example 119) (200 mg, 0.72 mmol) and cyclopropanesulfonyl chloride (161 mg, 1.1 mmol) according to the procedure described for Example 27. Obtained the title compound as an off-white foam (25 mg, 9%), MS (ISP) m/e=382.4 [(M−H)⁻].

EXAMPLE 150

N-[2-(3-Cyclopropyl-phenylamino)-4H-benzo[d][1,3]oxazin-6-yl]-benzenesulfonamide

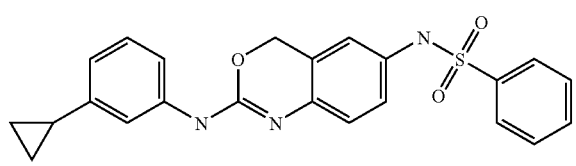

Prepared from N²-(3-Cyclopropyl-phenyl)-4H-benzo[d][1,3]oxazine-2,6-diamine (Example 119) (200 mg, 0.72 mmol) and benzenesulfonyl chloride (139 mg, 0.78 mmol) according to the procedure described for Example 27. Obtained the title compound as an off-white foam (174 mg, 58%), MS (ISP) m/e=420.3 [(M+H)⁺].

EXAMPLE 151

1-[2-(3-Cyclopropyl-phenylamino)-4H-benzo[d][1,3]oxazin-6-yl]-3-isopropyl-urea

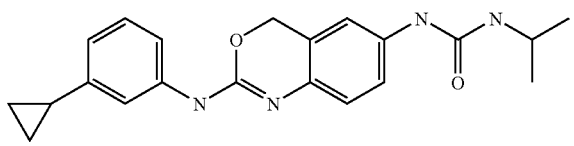

Prepared from N²-(3-cyclopropyl-phenyl)-4H-benzo[d][1,3]oxazine-2,6-diamine (Example 119) (215 mg, 0.77 mmol) and isopropyl isocyanate (72 mg, 0.84 mmol) according to the procedure described for Example 16. Obtained the title compound as a white solid (144 mg, 51%), MS (ISP) m/e=363.5 [(M−H)⁻].

EXAMPLE 152

(6-Cyclopropyl-4H-benzo[d][1,3]oxazin-2-yl)-(R)-indan-1-yl-amine

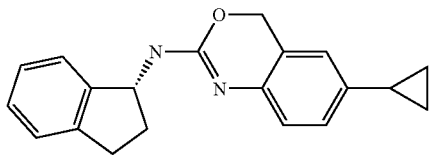

A stirred mixture of (6-bromo-4H-benzo[d][1,3]oxazin-2-yl)-(R)-indan-1-yl-amine (Example 32) (171.6 mg, 0.5 mmol), cyclopropylboronic acid (85.9 mg, 1.0 mmol), tricyclohexylphosphine (28 mg, 0.1 mmol), potassiumphosphate (371.5 mg, 1.75 mmol) and palladium actetate (11.2 mg, 0.05 mmol) in toluene (2 ml) and water (0.1 ml) was heated in a sealed tube at 110° C. for 17 h. The reaction mixture was poured into water (20 ml), extracted with ethyl acetate (2×30 ml). The combined organic layers were washed with water (20 ml) and brine (20 ml), dried (magnesium sulfate) and evaporated. Further purification by flash chromatography (ethyl acetate/heptane) on silica gel and crystallization (dichloromethane/heptane) yielded the title compound as colorless gum (69 mg, 41%). MS (ISP): m/e=305.2 (M+H⁺).

EXAMPLE 153

N²-Cyclooctyl-4H-benzo[d][1,3]oxazine-2,6-diamine

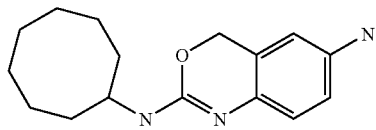

Step A: Cyclooctyl-(6-nitro-4H-benzo[d][1,3]oxazin-2-yl)-amine: Prepared from tert-butyl-(2-isothiocyanato-5-nitro-benzyloxy)-dimethyl-silane (Example C1) (4.0 g, 12 mmol) and cyclooctylamine (1.6 g, 12 mmol) according to the procedure described for Example 1. Obtained the title compound as a yellow viscous oil (3.2 g, 83%), MS (ISP) m/e=304.1 [(M+H)⁺].

Step B: N²-Cyclooctyl-4H-benzo[d][1,3]oxazine-2,6-diamine: Prepared from the above described cyclooctyl-(6-nitro-4H-benzo[d][1,3]oxazin-2-yl)-amine (3.05 g, 10 mmol) according to the procedure described for Example 2 step B. Obtained the title compound as a brown solid (2.55 g, 92%), MS (ISP) m/e=274.2 [(M+H)⁺].

EXAMPLE 154

1-(2-Cycloheptylamino-4H-benzo[d][1,3]oxazin-6-yl)-3-isopropyl-urea

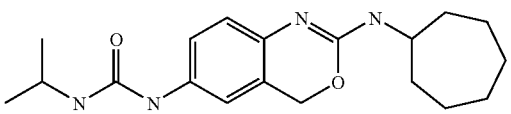

Prepared from N²-cyclooctyl-4H-benzo[d][1,3]oxazine-2,6-diamine (210 mg, 0.81 mmol) and isopropyl isocyanate (76 mg, 0.89 mmol) according to the procedure described for Example 16. Obtained the title compound as an off-white foam (55 mg, 20%), MS (ISP) m/e=345.3 [(M+H)⁺].

EXAMPLE 155

Cyclopropanecarboxylic acid (2-cyclooctylamino-4H-benzo[d][1,3]oxazin-6-yl)-amide

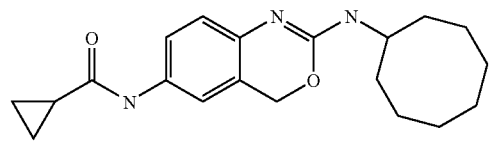

Prepared from N²-cyclooctyl-4H-benzo[d][1,3]oxazine-2,6-diamine (150 mg, 0.55 mmol) and and cyclopropane carboxylic acid (64 mg, 0.62 mmol) according to the procedure described for example 93. Obtained the title compound as a brown solid (195 mg, 99%), MS (ISP) m/e=342.2 [(M+H)⁺].

EXAMPLE 156

N-(2-Cyclooctylamino-4H-benzo[d][1,3]oxazin-6-yl)-2-(4-methyl-piperazin-1-yl)-acetamide

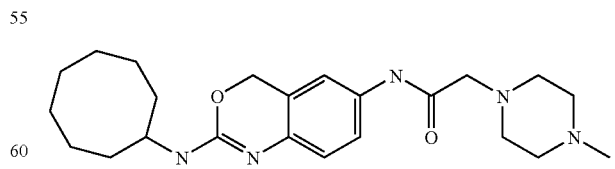

Prepared from N²-cyclooctyl-4H-benzo[d][1,3]oxazine-2,6-diamine (150 mg, 0.55 mmol) and and 4-methylpiperazin-1-acetic acid (95 mg, 0.60 mmol) according to the procedure described for example 93. Obtained the title compound as a brown solid (140 mg, 62%), MS (ISP) m/e=414.4 [(M+H)⁺].

EXAMPLE 157 endo-N-[2-((R)-indan-1-ylamino)-4H-benzo[d][1,3]oxazin-6-yl]-2-(9-methyl-3-oxa-9-aza-bicyclo[3.3.1]non-7-yl)-acetamide

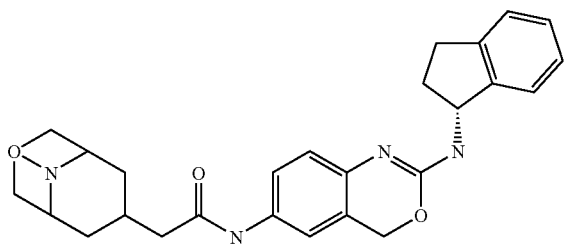

Step A: (9-Benzyl-3-oxa-9-aza-bicyclo[3.3.1]non-7-ylidene)-acetic acid ethyl ester: To a suspension of sodium hydride (55%, 585 mg, 13.62 mmol) in 1,2-dimethoxyethane (20 ml) at 0° C. was added slowly triethyl phosphonoacetate (2.8 ml, 14.2 mmol) and the mixture was stirred at 23° C. for 1 h, cooled to 0° C., 9-benzyl-3-oxa-9-aza-bicyclo[3.3.1]nonan-7-one (CAS 81514-40-1) (2.93 g, 12.89 mmol) in 1,2-dimethoxyethane (10 ml) added and stirred at reflux for 2 h. Cooled to 23° C., poured into water, extracted three times with ethyl acetate and water, the organic layers were combined, dried over magnesium sulfate, filtered and the solvents were evaporated to give a crude product which was purified by silica gel column chromatography with n-heptane and ethyl acetate to give the title compound as a light yellow oil (454 mg, 12%), MS (ISP) m/e=302.2 [(M+H)$^+$].

Step B: endo-(3-Oxa-9-aza-bicyclo[3.3.1]non-7-yl)-acetic acid ethyl ester: The above described (9-benzyl-3-oxa-9-aza-bicyclo[3.3.1]non-7-ylidene)-acetic acid ethyl ester (290 mg, 0.960 mmol) was dissolved in ethanol (20 ml), degassed, palladium hydroxide (20 mg, 0.029 mmol) was added and the mixture stirred at 23° C. under hydrogen atmosphere for 18 h. The reaction mixture was filtered, washed with ethanol and the solvent was evaporated to give the title compound as a colorless oil (206 mg, 100%), MS (ISP) m/e=214.2 [(M+H)$^+$].

Step C: endo-(9-Methyl-3-oxa-9-aza-bicyclo[3.3.1]non-7-yl)-acetic acid ethyl ester: The above described endo-(3-oxa-9-aza-bicyclo[3.3.1]non-7-yl)-acetic acid ethyl ester (206 mg, 0.966 mmol) was dissolved in ethanol (20 ml), sodium cyanoborohydride (320 mg, 4.829 mmol) was added, followed by aqueous formaldehyde solution (36.5%, 119 mg, 1.449 mmol). The reaction mixture was stirred at 23° C. for 1 h. Neutralisation to pH 7 was achieved by dropwise addition of glacial acetic acid and the mixture was allowed to stir for additional 2 h. The reaction mixture was extracted with sat. sodium hydrogen carbonate-sol. and ethyl acetate, the organic layers were combined, dried over sodium sulfate, filtered and the solvents evaporated. Purification by flash chromatography with n-heptane and ethyl acetate over a Si-NH$_2$ column gave the title compound as a colorless oil (140 mg, 64%), MS (ISP) m/e=228.2 [(M+H)$^+$].

Step D: endo-(9-Methyl-3-oxa-9-aza-bicyclo[3.3.1]non-7-yl)-acetic acid: The above described endo-(9-methyl-3-oxa-9-aza-bicyclo[3.3.1]non-7-yl)-acetic acid ethyl ester (140 mg, 0.616 mmol) was dissolved in 3N HCl (3 ml) and stirred at 23° C. for 30 min. The solvents were evaporated to give the title compound as a colorless oil (123 mg, 100%), MS (ISP) m/e=200.2 [(M+H)$^+$].

Step E: endo-N-[2-((R)-Indan-1-ylamino)-4H-benzo[d][1,3]oxazin-6-yl]-2-(9-methyl-3-oxa-9-aza-bicyclo[3.3.1]non-7-yl)-acetamide: The above described endo-(9-methyl-3-oxa-9-aza-bicyclo[3.3.1]non-7-yl)-acetic acid (123 mg, 0.617 mmol) was dissolved in dichloromethane (15 ml) and diisopropylethyl amine (315 ul, 1.851 mmol), then at 23° C. 2-(1H-benzotriazole-1-yl)-1,1,3,3-tetramethyluronium tetrafluoroborate (238 mg, 0.74 mmol) was added and stirred at 23° C. for 15 min. (R)—N-2-Indan-1-yl-4H-benzo[d][1,3]oxazine-2,6-diamine (172 mg, 0.617 mmol; HPLC: 0.618 min) was added and the reaction mixture was stirred at 23° C. for 6 h. The reaction mixture was extracted with dichloromethane, ice water and sat. sodium hydrogen carbonate-solution, the organic layers were dried over magnesium sulfate, filtered and the solvents evaporated. Purification by flash chromatography with n-heptane and ethyl acetate, followed by trituration with dichloromethane and diethyl ether gave the title compound as an off-white solid (16 mg, 5.6%; HPLC 0.604 min), MS (ISP) m/e=461.2 [(M+H)$^+$].

EXAMPLE 158

2-((3SR,5SR)-3,5-Bis-(methoxymethyl)-4-methyl-piperazin-1-yl)-N-[2-((R)-indan-1-ylamino)-4H-benzo[d][1,3]oxazin-6-yl]-acetamide

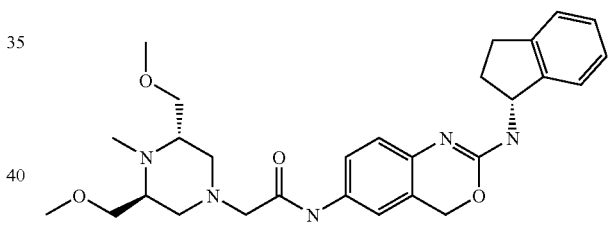

Step A: (2SR,6SR)-4-Benzenesulfonyl-1-benzyl-piperazine-2,6-dicarboxylic acid diethyl ester: To a solution of (SR)-3-[benzenesulfonyl-((SR)-2-bromo-2-ethoxycarbonyl-ethyl)-amino]-2-bromo-propionic acid ethyl ester (CAS 58661-68-0) (13.8 g, 26.8 mmol) in toluene (54 ml) was added benzylamine (8.81 ml, 80.4 mmol) and the mixture was stirred at 90° C. for 1.5 h. Cooled to 23° C., filtered the solid off, washed with toluene and the filtrate was evaporated to leave a crude product which was purified by silica gel column chromatography with tert-butyl methyl ether and n-heptane 3:7 to give the title compound as light yellow crystals (7.0 g, 57%), MS (ISP) m/e=461.2 [(M+H)$^+$].

Step B: ((2SR,6SR)-4-Benzenesulfonyl-1-benzyl-6-hydroxymethyl-piperazin-2-yl)-methanol: To a solution of the above described (2SR,6SR)-4-benzenesulfonyl-1-benzyl-piperazine-2,6-dicarboxylic acid diethyl ester (7.0 g, 15 mmol) in tetrahydrofuran (165 ml) at 23° C. was added a solution of lithium aluminum hydride in tetrahydrofuran (c=1 mol/l, 45.6 ml, 45.6 mmol) and the mixture was stirred at 70° C. for 1 h. Then the reaction was cooled to 0° C., water (1.75 ml) was added very slowly, then NaOH 15% (1.75 ml) and water (5.24 ml). The mixture was stirred at 23° C. for 1.5 h, the precipitate was filtered off, washed with tetrahydrofuran and the organic layer was evaporated totally to give the title compound as a white solid (4.45 g, 78%), MS (ISP) m/e=377.3 [(M+H)⁺].

Step C: (2SR,6SR)-4-Benzenesulfonyl-1-benzyl-2,6-bis-methoxymethyl-piperazine: To a solution of the above described ((2SR,6SR)-4-benzenesulfonyl-1-benzyl-6-hydroxymethyl-piperazin-2-yl)-methanol (4.45 g, 11.81 mmol) in N,N-dimethylformamide (26 ml) at 23° C. was added NaH (55% in mineral oil, 1.677 g, 38.45 mmol) and the mixture was stirred at 23° C. for 1 h. Added methyl iodide (1.65 ml, 26.6 mmol) and stirred at 23° C. for 1 h. Poured into water, extracted with tert-butyl methyl ether, dried organic layer over sodium sulfate. Removal of the solvent in vacuum left a yellow oil. Silica gel column chromatography with n-heptane and ethyl acetate gave a light yellow solid (2.36 g, 49%)., MS (ISP) m/e=405.3 [(M+H)⁺].

Step D: (3SR,5SR)-1-Benzenesulfonyl-3,5-bis-methoxymethyl-piperazine: A mixture of the above described (2SR,6SR)-4-benzenesulfonyl-1-benzyl-2,6-bis-methoxymethyl-piperazine (2.355 g, 5.82 mmol) in ethanol (300 ml) with 10% palladium on carbon (620 mg, 10 mol %) was hydrogenated at 50° C. for 2 h. The catalyst was filtered off, washed with ethanol, the filtrate was evaporated totally and dried in high vacuum to give the title compound as a white solid (1.74 g, 95%), MS (ISP) m/e=315.0 [(M+H)⁺].

Step E: (2SR,6SR)-4-Benzenesulfonyl-2,6-bis-methoxymethyl-1-methyl-piperazine: To a mixture of the above described (3SR,5SR)-1-benzenesulfonyl-3,5-bis-methoxymethyl-piperazine (1.68 g, 5.343 mmol) in acetonitrile (40 ml) and 36.5% formaldehyde solution in water (0.653 ml, 8.015 mmol) and 5-7 drops of acetic acid at 23° C. was added sodium cyanoborohydride (1.679 g, 26.71 mmol) and the mixture was stirred at 23° C. for 1.5 h. Poured onto water and extracted twice with ethyl acetate, dried the organic layer over sodium sulfate, filtered off, evaporated all volatiles totally and dried in high vacuum to give the title compound as a colorless oil (1.05 g, 60%), pure enough for further steps; MS (ISP) m/e=329.1 [(M+H)⁺].

Step F: (2SR,6SR)-2,6-Bis-methoxymethyl-1-methyl-piperazine hydrochloride: To a mixture of the above described (2SR,6SR)-4-benzenesulfonyl-2,6-bis-methoxymethyl-1-methyl-piperazine (910 mg, 2.771 mmol) in xylene (20 ml) was added sodium dihydro-bis(2-methoxyethoxy)aluminate in toluene (2.154 ml, 7.065 mmol) and the mixture was stirred at 140° C. for 18 h. Cooled to 23° C., poured into 2 M HCl, extracted twice with tert-butyl methyl ether, the aqueous layer was made alkaline with 10 M NaOH-sol., extracted twice with tert-butyl methyl ether, the combined organic layer was dried over sodium sulfate, filtered, to the filtrate was added ethanol (5 ml) and chlorotrimethylsilane (ca. 0.5 ml) and all volatiles were removed in vacuum to give the title compound as a colorless oil (350 mg, 56%), MS (ISP) m/e=189.3 [(M+H)⁺].

Step F: 2-((3SR,5SR)-3,5-Bis-methoxymethyl-4-methyl-piperazin-1-yl)-N-[2-((R)-indan-1-ylamino)-4H-benzo[d][1,3]oxazin-6-yl]-acetamide: Prepared from 2-chloro-N-[2-((R)-indan-1-ylamino)-4H-benzo[d][1,3]oxazin-6-yl]-acetamide (Example 3 step A) (100 mg, 0.281 mmol), the above described (2SR,6SR)-2,6-bis-methoxymethyl-1-methyl-piperazine hydrochloride (69.5 mg, 0.309 mmol) and diisopropylethyl amine (144 ul, 0.843 mmol) in acetonitrile (2 ml) according to the procedure described for Example 3 step B. Obtained the title compound as a light yellow solid (15 mg, 11%), MS (ISP) m/e=508.4 [(M+H)⁺].

EXAMPLE 159

N-[2-((R)-Indan-1-ylamino)-4H-benzo[d][1,3]oxazin-6-yl]-2-(9-methyl-3-oxa-7,9-diaza-bicyclo[3.3.1]non-7-yl)-acetamide

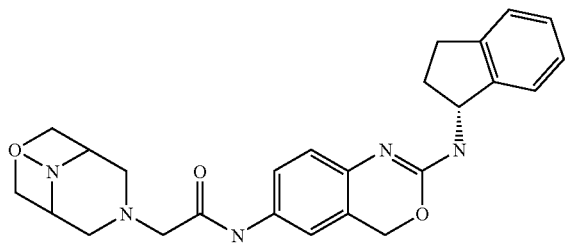

Step A: 7-Benzenesulfonyl-3-oxa-7,9-diaza-bicyclo[3.3.1]nonane: A mixture of 7-benzenesulfonyl-9-benzyl-3-oxa-7,9-diaza-bicyclo[3.3.1]nonane (CAS 335620-96-7) (2.074 g, 5.66 mmol) and 10% palladium on carbon (780 mg, 10 mol %) in ethanol (130 mL) was hydrogenated at atmospheric hydrogen pressure at 50° C. for 1.5 days. Cooled to 23° C., filtered the catalyst off, washed with ethanol, the solvent was removed in vacuum to the title compound as a light yellow solid (1.253 g, 83%), MS (ISP) m/e=269.2 [(M+H)⁺].

Step B: 7-Benzenesulfonyl-9-methyl-3-oxa-7,9-diaza-bicyclo[3.3.1]nonane: To a mixture of the above described 7-benzenesulfonyl-3-oxa-7,9-diaza-bicyclo[3.3.1]nonane (1.25 g, 4.658 mmol) in acetonitrile (40 ml) and 36.5% formaldehyde solution in water (0.53 ml, 6.987 mmol) and 5 drops of acetic acid at 23° C. was added sodium cyanoborohydride (1.464 g, 23.29 mmol) and the mixture was stirred at 23° C. for 2 h. Poured onto water and extracted twice with ethyl acetate, dried the organic layer over sodium sulfate, filtered off, evaporated all volatiles totally and dried in high vacuum to give after silica gel column chromatography with ethyl acetate and additional methanol and aqueous ammonia solution the title compound as a colorless oil (0.88 g, 67%), MS (ISP) m/e=283.1 [(M+H)⁺].

Step C: 9-Methyl-3-oxa-7,9-diaza-bicyclo[3.3.1]nonane hydrochloride: To a mixture of the above described 7-benzenesulfonyl-9-methyl-3-oxa-7,9-diaza-bicyclo[3.3.1]nonane (880 mg, 3.177 mmol) in xylene (20 ml) was added sodium dihydro-bis(2-methoxyethoxy)aluminate in toluene (2.423 ml, 7.947 mmol) and the mixture was stirred at 140° C. for 18 h. Cooled to 23° C., poured into 2 M HCl, extracted twice with tert-butyl methyl ether, the aqueous layer was made alkaline with 10 M NaOH-sol., extracted twice with tert-butyl methyl ether, the combined organic layer was dried over sodium sulfate, filtered, to the filtrate was added ethanol (5 ml) and chlorotrimethylsilane (ca. 0.5 ml) and all volatiles were removed in vacuum to give the title compound as a colorless oil (190 mg, 43%), MS (ISP) m/e=143.2 [(M+H)⁺].

Step D: 2-((3SR,5SR)-3,5-Bis-methoxymethyl-4-methyl-piperazin-1-yl)-N-[2-((R)-indan-1-ylamino)-4H-benzo[d][1,3]oxazin-6-yl]-acetamide: Prepared from 2-chloro-N-[2-((R)-indan-1-ylamino)-4H-benzo[d][1,3]oxazin-6-yl]-acetamide (Example 3 step A) (250 mg, 0.703 mmol), the above described 9-methyl-3-oxa-7,9-diaza-bicyclo[3.3.1]nonane hydrochloride (138 mg, 0.773 mmol) and diisopropylethyl amine (359 ul, 2.11 mmol) in acetonitrile (5 ml) according to the procedure described for Example 3 step B. Obtained the title compound as an off-white solid (16 mg, 5%), MS (ISP) m/e=462.3 [(M+H)+].

The invention claimed is:
1. A compound of formula (I)

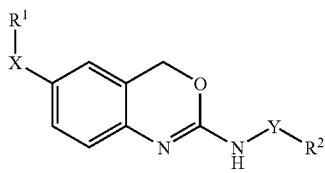

wherein
X is a bond, —NH—, —NH—S(O)$_2$—, —NH—CH$_2$—, —CH$_2$—, —NH—C(O)—, —CH$_2$—NH—C(O)—, —NH—C(O)—CH$_2$—, —NH—C(O)—CH$_2$—NH—, —NR$^a$—C(O)—NR$^b$—, or —NH—S(O)$_2$—NH—;
R$^1$ is halo;
C$_{1-7}$-alkyl, optionally substituted by OH, C$_{1-7}$ alkoxy or CN;
C$_{1-7}$-alkoxy;
—NR$^a$R$^b$;
—C(NH$_2$)N(OH);
cyano;
nitro;
cycloalkyl;
heterocycloalkyl;
aryl;
heteroaryl; or
vinyl;
wherein each of said cycloalkyl, heterocycloalkyl, aryl and heteroaryl is optionally substituted by one or more halo, cyano, nitro, C$_{1-7}$-alkyl, C$_{1-7}$-haloalkyl, C$_{1-7}$-hydroxyalkyl, C$_{1-7}$-cyanoalkyl, C$_{1-7}$-alkoxy, C$_{1-7}$-alkoxy-alkyl, —NR$^a$R$^b$, or 3- to 7-membered monocyclic cycloalkyl; and
wherein said vinyl is optionally substituted by phenyl or a 5- or 6-membered monocyclic heteroaryl;
Y is a bond, —CH$_2$— or —CH$_2$—CH$_2$—O—;
R$^2$ is cycloalkyl;
heterocycloalkyl;
aryl;
heteroaryl; or
5- or 6-membered cycloalkyl or heterocycloalkyl, anellated with a benzo ring;
wherein each of said cycloalkyl, heterocycloalkyl, aryl, heteroaryl, 5- or 6-membered cycloalkyl or heterocycloalkyl anellated with a benzo ring is optionally substituted by one or more halo, hydroxyl, C$_{1-7}$-alkyl, C$_{1-7}$-alkoxy, or 3- to 7-membered monocyclic cycloalkyl; and
R$^a$ and R$^b$ are each independently hydrogen or C$_{1-7}$-alkyl;
or a pharmaceutically acceptable salt or ester thereof.
2. The compound of claim 1 wherein:
X is a bond, —NH—, —NH—S(O)$_2$—, —NH—CH$_2$—, —CH$_2$—, —NH—C(O)—, —CH$_2$—NH—C(O)—, —NH—C(O)—CH$_2$—, —NH—C(O)—CH$_2$NH—, —NR$^a$—C(O)—NR$^b$—, or —NH—S(O)$_2$—NH—;
R$^1$ is halo;
C$_{1-7}$-alkyl, optionally substituted by OH or CN;
C$_{1-7}$-alkoxy;
—NR$^a$R$^b$;
—C(NH$_2$)N(OH);
cyano;
nitro;
cycloalkyl;
heterocycloalkyl;
aryl;
heteroaryl; or
vinyl;
wherein each of said cycloalkyl, heterocycloalkyl, aryl and heteroaryl is optionally substituted by one or more halo, cyano, nitro, C$_{1-7}$-alkyl, C$_{1-7}$-haloalkyl, C$_{1-7}$-hydroxyalkyl, C$_{1-7}$-cyanoalkyl, C$_{1-7}$-alkoxy, —NR$^a$R$^b$, or 3- to 7-membered monocyclic cycloalkyl; and
wherein said vinyl is optionally substituted by phenyl or a 5- or 6-membered monocyclic heteroaryl;
Y is a bond, —CH$_2$— or —CH$_2$—CH$_2$—O—;
R$^2$ is cycloalkyl;
heterocycloalkyl;
aryl;
heteroaryl; or
5- or 6-membered cycloalkyl or heterocycloalkyl, anellated with a benzo ring;
wherein each of said cycloalkyl, heterocycloalkyl, aryl, heteroaryl, 5- or 6-membered cycloalkyl or heterocycloalkyl anellated with a benzo ring is optionally substituted by one or more halo, hydroxyl, C$_{1-7}$-alkyl, C$_{1-7}$-alkoxy, or 3- to 7-membered monocyclic cycloalkyl; and
R$^a$ and R$^b$ is each independently hydrogen or C$_{1-7}$-alkyl;
or a pharmaceutically acceptable salt thereof.
3. The compound of claim 1 having formula formula (Ia):

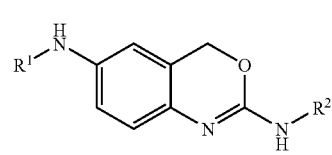

wherein
R$^1$ is heteroaryl, optionally substituted by one or more C$_{1-7}$-alkyl, C$_{1-7}$-haloalkyl and cyclopropyl;
R$^2$ is 5- or 6-membered cycloalkyl or heterocycloalkyl anellated with a benzo ring, optionally substituted by one or more halo and C$_{1-7}$-alkoxy;
or a pharmaceutically acceptable salt thereof.
4. The compound of claim 3 wherein:
R$^1$ is heteroaryl selected from the group consisting of pyridinyl, pyrimidinyl, [1,3,4]oxadiazolyl, and 2H-tetrazolyl; wherein said heteroaryl is optionally substituted by one or more C$_{1-7}$-alkyl, C$_{1-7}$-haloalkyl or cyclopropyl;
R$^2$ is

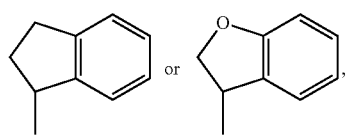

wherein said radicals are optionally substituted by one or more halo and C$_{1-7}$-alkoxy;
or a pharmaceutically acceptable salt thereof.

5. The compound of claim 4 selected from the group consisting of:
  $N^2$—(R)-Indan-1-yl-$N^6$-(6-trifluoromethyl-pyridin-2-yl)-4H-benzo[d][1,3]oxazine-2,6-diamine,
  $N^2$—(R)-Indan-1-yl-$N^6$-(4-trifluoromethyl-pyrimidin-2-yl)-4H-benzo[d][1,3]oxazin-2.6-diamine,
  $N^6$-(4,6-Dimethyl-pyrimidin-2-yl)-$N^2$—(R)-indan-1-yl-4H-benzo[d][1,3]oxazine-2,6-diamine,
  rac-$N^2$-(5-Fluoro-indan-1-yl)-$N^5$-(6-trifluoromethyl-pyridin-2-yl)-4H-benzo[d][1,3]oxazine-2,6-diamine,
  rac-$N^2$-(5-Fluoro-indan-1-yl)-$N^6$-(4-trifluoromethyl-pyrimidin-2-yl)-4H-benzo[d][1,3]oxazine-2,6-diamine,
  rac-$N^2$-(4-Methoxy-2,3-dihydro-benzofuran-3-yl)-$N^6$-(6-trifluoromethyl-pyridin-2-yl)-4H-benzo[d][1,3]oxazine-2,6-diamine,
  rac-$N^2$-(4-Methoxy-2,3-dihydro-benzofuran-3-yl)-$N^6$-(4-trifluoromethyl-pyrimidin-2-yl)-4H-benzo[d][1,3]oxazine-2,6-diamine,
  rac-$N^2$-(7-Methoxy-indan-1-yl)-$N^6$-(6-trifluoromethyl-pyridin-2-yl)-4H-benzo[d][1,3]oxazine-2,6-diamine,
  rac-$N^2$-(7-Methoxy-indan-1-yl)-$N^6$-(4-trifluoromethyl-pyrimidin-2-yl)-4H-benzo[d][1,3]oxazine-2,6-diamine, and
  $N^2$-(7-Methoxy-indan-1-yl)-$N^6$-(5-methyl-[1,3,4]oxadiazol-2-yl)-4H-benzo[d][1,3]oxazine-2,6-diamine.

6. The compound of claim 4 selected from the group consisting of:
  rac-$N^2$-(5-Fluoro-indan-1-yl)-$N^6$-(5-methyl-[1,3,4]oxadiazol-2-yl)-4H-benzo[d][1,3]oxazine-2.6-diamine,
  rac-$N^2$-(4-Methoxy-2,3-dihydro-benzofuran-3-yl)-$N^6$-(5-methyl-[1,3,4]oxadiazol-2-yl)-4H-benzo[d][1,3]oxazine-2,6-diamine,
  $N^6$-(5-Cyclopropyl-[1,3,4]oxadiazol-2-yl)-$N^2$-(7-methoxy-indan-1-yl)-4H-benzo[d][1,3]oxazine-2,6-diamine,
  $N^6$-(2-tert-Butyl-2H-tetrazol-5-yl)-$N^2$-(7-methoxy-indan-1-yl)-4H-benzo[d][1,3]oxazine-2,6-diamine,
  $N^2$—(R)-Indan-1-yl-$N^6$-(5-methyl-[1,3,4]oxadiazol-2-yl)-4H-benzo[d][1,3]oxazine-2,6-diamine,
  $N^2$—(R)-Indan-1-yl-$N^6$-(5-trifluoromethyl-[1,3,4]oxadiazol-2-yl)-4H-benzo[d][1,3]oxazine-2,6-diamine,
  $N^2$-(7-Methoxy-indan-1-yl)-$N^6$-(5-trifluoromethyl-[1,3,4]oxadiazol-2-yl)-4H-benzo[d][1,3]oxazine-2,6-diamine,
  $N^2$-(4-Methoxy-2,3-dihydro-benzofuran-3-yl)-$N^6$-(5-trifluoromethyl-[1,3,4]oxadiazol-2-yl)-4H-benzo[d][1,3]oxazine-2,6-diamine, and
  $N^2$-(5-Fluoro-indan-1-yl)-$N^6$-(5-trifluoromethyl-[1,3,4]oxadiazol-2-yl)-4H-benzo[d][1,3]oxazine-2,6-diamine.

7. The compound of claim 1 having formula (Ib):

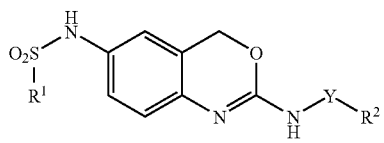

(Ib)

wherein
  $R^1$ is $C_{1-7}$-alkyl;
  —$NR^aR^b$;
  cycloalkyl;
  heterocycloalkyl; or
  aryl;

wherein each of said cycloalkyl, heterocycloalkyl and aryl is optionally substituted by one or more $C_{1-7}$-alkyl;
Y is a bond or —$CH_2$—$CH_2$—O—;
$R^2$ is cycloalkyl;
aryl; or
5- or 6-membered cycloalkyl or heterocycloalkyl, anellated with a benzo ring;
wherein each of said 5- or 6-membered cycloalkyl or heterocycloalkyl anellated with a benzo ring is optionally substituted by one or more halo, $C_{1-7}$-alkoxy and cyclopropyl; and
$R^a$ and $R^b$ is each independently hydrogen or $C_{1-7}$-alkyl;
or a pharmaceutically acceptable salt thereof.

8. The compound of claim 7 wherein:
  $R^1$ is methyl;
  —$N(CH_3)_2$;
  cyclopropyl;
  phenyl; or
  heterocycloalkyl, selected from the group consisting of

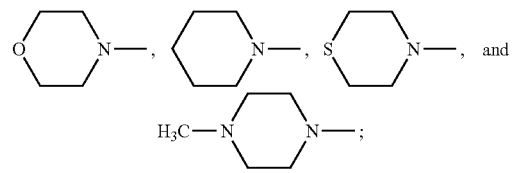

Y is a bond or —$CH_2$—$CH_2$—O—;
$R^2$ is cyclooctyl;
phenyl, optionally substituted by cyclopropyl; or
a 5- or 6-membered cycloalkyl or heterocycloalkyl, anellated with a benzo ring, selected from the group consisting of

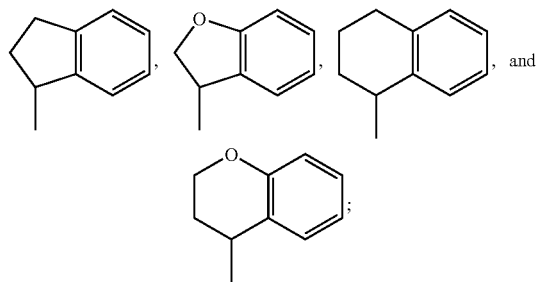

wherein each of said 5- or 6-membered cycloalkyl or heterocycloalkyl anellated with a benzo ring is optionally substituted by one or more halo, $C_{1-7}$-alkoxy and cyclopropyl;
or a pharmaceutically acceptable salt thereof.

9. The compound of claim 8 selected from the group consisting of:
  N,N-(Dimethyl)-N'-{2-((R)-indan-1-ylamino)-4H-benzo[d][1,3]oxazin-6-yl}-sulfamide,
  Piperidine-1-sulfonic acid [2-((R)-indan-1-ylamino)-4H-benzo[d][1,3]oxazin-6-yl]-amide,
  Morpholine-4-sulfonic acid [2-((R)-indan-1-ylamino)-4H-benzo[d][1,3]oxazin-6-yl]-amide,
  rac-N,N-(Dimethyl)-N'-{2-(4-methoxy-2,3-dihydro-benzofuran-3-ylamino)-4H-benzo[d][1,3]oxazin-6-yl}-sulfamide,
  Piperidine-1-sulfonic acid [2-(4-methoxy-2,3-dihydro-benzofuran-3-ylamino)-4H-benzo[d][1,3]oxazin-6-yl]-amide, rac-N,N-(Dimethyl)-N'-{2-(7-Methoxy-indan-1-ylamino)-4H-benzo[d][1,3]oxazin-6-yl}-sulfamide,
rac-Piperidine-1-sulfonic acid [2-(7-methoxy-indan-1-ylamino)-4H-benzo[d][1,3]oxazin-6-yl]-amide,
rac-Morpholine-4-sulfonic acid [2-(7-methoxy-indan-1-ylamino)-4H-benzo[d][1,3]oxazin-6-yl]-amide,
rac-N,N-(Dimethyl)-N'-{2-(5-Fluoro-indan-1-ylamino)-4H-benzo[d][1,3]oxazin-6-yl}-sulfamide,
4-Methyl-piperazine-1-sulfonic acid {2-[(R)-(1,2,3,4-tetrahydro-naphthalen-1-yl)amino]-4H-benzo[d][1,3]oxazin-6-yl}-amide, and
4-Methyl-piperazine-1-sulfonic acid [2-((R)-indan-1-ylamino)-4H-benzo[d][1,3]oxazin-6yl]-amide.

10. The compound of claim 8 selected from the group consisting of:
N-[2-((R)-Indan-1-ylamino)-4H-benzo[d][1,3]oxazin-6-yl]-methanesulfonamide,
Cyclopropanesulfonic acid [2-((R)-indan-1-ylamino)-4H-benzo[d][1,3]oxazin-6-yl]-amide,
N-[2-((R)-Indan-1-ylamino)-4H-benzo[d][1,3]oxazin-6-yl]-benzenesulfonamide,
rac-N,N-(Dimethyl)-N'-{2-(Chroman-4-ylamino)-4H-benzo[d][1,3]oxazin-6-yl}-sulfamide
Cyclopropanesulfonic acid (2-cycloheptylamino-4H-benzo[d][1,3]oxazin-6-yl)-amide,
N,N-(Dimethyl)-N'-{2-cycloheptylamino-4H-benzo[d][1,3]oxazin-6-yl-}-sulfamide,
N-(2-Cycloheptylamino-4H-benzo[d][1,3]oxazin-6-yl)-benzenesulfonamide,
rac-N-[2-(7-Methoxy-indan-1-ylamino)-4H-benzo[d][1,3]oxazin-6-yl]-methanesulfonamide,
rac-Cyclopropanesulfonic acid [2-(7-methoxy-indan-1-ylamino)-4H-benzo[d][1,3]oxazin-6-yl]-amide, and
rac-N-[2-(7-Methoxy-indan-1-ylamino)-4H-benzo[d][1,3]oxazin-6-yl]-benzenesulfonamide.

11. The compound of claim 8 selected from the group consisting of:
Cyclopropanesulfonic acid [2-(2-phenoxy-ethylamino)-4H-benzo[d][1,3]oxazin-6-yl]-amide,
N-[2-(2-Phenoxy-ethylamino)-4H-benzo[d][1,3]oxazin-6-yl]-benzenesulfonamide,
N,N-(Dimethyl)-N'-{2-(2-Phenoxy-ethylamino)-4H-benzo[d][1,3]oxazin-6-yl}-sulfamide,
Cyclopropanesulfonic acid [2-(4-methoxy-2,3-dihydro-benzofuran-3-ylamino)-4H-benzo[d][1,3]oxazin-6-yl]-amide,
N-[2-(4-Methoxy-2,3-dihydro-benzofuran-3-ylamino)-4H-benzo[d][1,3]oxazin-6-yl]-methanesulfonamide,
N-[2-(4-Methoxy-2,3-dihydro-benzofuran-3-ylamino)-4H-benzo[d][1,3]oxazin-6-yl]-benzenesulfonamide,
Cyclopropanesulfonic acid [2-(3-cyclopropyl-phenylamino)-4H-benzo[d][1,3]oxazin-6-yl]-amide, and
N-[2-(3-Cyclopropyl-phenylamino)-4H-benzo[d][1,3]oxazin-6-yl]-benzenesulfonamide.

12. The compound of claim 1 having formula (Ic)

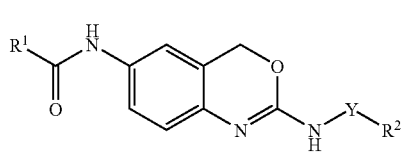

(Ic)

wherein
$R^1$ is $C_{1-7}$-alkyl or cycloalkyl;
Y is a bond, —$CH_2$— or —$CH_2$—$CH_2$—O—;
$R^2$ is cycloalkyl;
aryl;
heteroaryl; or
5- or 6-membered cycloalkyl or heterocycloalkyl, anellated with a benzo ring;
wherein each of said cycloalkyl, aryl, heteroaryl, 5- or 6-membered cycloalkyl or heterocycloalkyl anellated with a benzo ring is optionally substituted by one or more halo, $C_{1-7}$-alkoxy and cyclopropyl;
or a pharmaceutically acceptable salt thereof.

13. The compound of claim 12 wherein:
$R^1$ is methyl or cyclopropyl;
Y is a bond, —$CH_2$— or —$CH_2$—$CH_2$—O—;
$R^2$ is cyclooctyl;
phenyl, optionally substituted by one or more $C_{1-7}$-alkoxy and cyclopropyl;
furanyl; or
a 5- or 6-membered cycloalkyl or heterocycloalkyl, anellated with a benzo ring, selected from the group consisting of

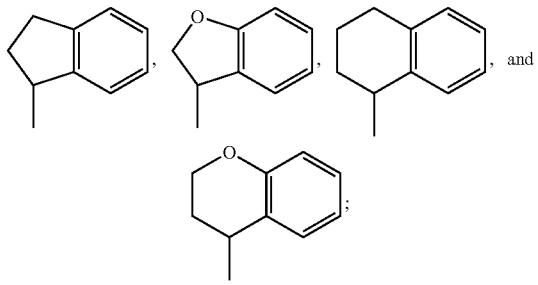

, and wherein each of said 5- or 6-membered cycloalkyl or heterocycloalkyl anellated with a benzo ring is optionally substituted by one or more halo and cyclopropyl;
or a pharmaceutically acceptable salt thereof.

14. The compound of claim 13 selected from the group consisting of:
Cyclopropanecarboxylic acid [2-(2-methoxy-benzylamino)-4H-benzo[d][1,3]oxazin-6-yl]-amide,
Cyclopropanecarboxylic acid [2-((R)-indan-1-ylamino)-4H-benzo[d][1,3]oxazin-6-yl]-amide,
rac-Cyclopropanecarboxylic acid [2-(5-fluoro-indan-1-ylamino)-4H-benzo[d][1,3]oxazin-6-yl]-amide,
rac-Cyclopropanecarboxylic acid [2-(8-methoxy-1,2,3,4-tetrahydro-naphthalen-1-ylamino)-4H-benzo[d][1,3]oxazin-6-yl]-amide,
Cyclopropanecarboxylic acid [2-(7-methoxy-indan-1-ylamino)-4H-benzo[d][1,3]oxazin-6-yl]-amide,
N-[2-((R)-Indan-1-ylamino)-4H-benzo[d][1,3]oxazin-6-yl]-acetamide,
N-[2-(4-Methoxy-2,3-dihydro-benzofuran-3-ylamino)-4H-benzo[d][1,3]oxazin-6-yl]-acetamide,
N-[2-(7-Methoxy-indan-1-ylamino)-4H-benzo[d][1,3]oxazin-6-yl]-acetamide,
Cyclopropanecarboxylic acid {2-[(5-methyl-furan-2-ylmethyl)-amino]-4H-benzo[d][1,3]oxazin-6-yl}-amide,
rac-Cyclopropanecarboxylic acid [2-(chroman-4-ylamino)-4H-benzo[d][1,3]oxazin-6-yl]-amide,
Cyclopropanecarboxylic acid (2-cycloheptylamino-4H-benzo[d][1,3]oxazin-6-yl)-amide, Cyclopropanecarboxylic acid [2-(2-phenoxy-ethylamino)-4H-benzo[d][1,3]oxazin-6-yl]-amide, Cyclopropanecarboxylic acid [2-(3-cyclopropyl-phenylamino)-4H-benzo[d][1,3]oxazin-6-yl]-amide, and Cyclopropanecarboxylic acid (2-cyclooctylamino-4H-benzo[d][1,3]oxazin-6-yl)-amide.

15. The compound of claim 1 having formula (Id):

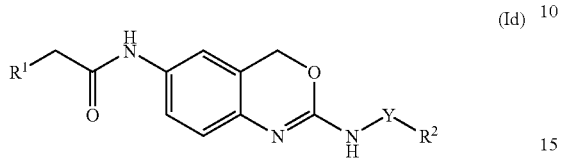

wherein $R^1$ is halo;

$C_{1-7}$-alkoxy;

heterocycloalkyl; or heteroaryl;

wherein each of said heterocycloalkyl and heteroaryl is optionally substituted by one or more $C_{1-7}$-alkyl, $C_{1-7}$-alkoxy, $C_{1-7}$-haloalkyl and $C_{1-7}$-hydroxyalkyl;

Y is a bond, —CH$_2$— or —CH$_2$—CH$_2$—O—;

$R^2$ is cycloalkyl;

aryl;

heteroaryl; or 5- or 6-membered cycloalkyl or heterocycloalkyl, anellated with a benzo ring;

wherein each of said cycloalkyl, aryl, heteroaryl, 5- or 6-membered cycloalkyl or heterocycloalkyl anellated with a benzo ring is optionally substituted by one or more halo, $C_{1-7}$-alkyl, $C_{1-7}$-alkoxy and cyclopropyl;

or a pharmaceutically acceptable salt thereof.

16. The compound of claim 15 wherein:

$R^1$ is halo;

methoxy;

imidazolyl; or heterocycloalkyl, selected from the group consisting of 9-methyl-3-oxa-7,9-diaza-bicyclo[3.3.1]non-7-yl, 9-methyl-3-oxa-9-aza-bicyclo[3.3.1]non-7-yl,

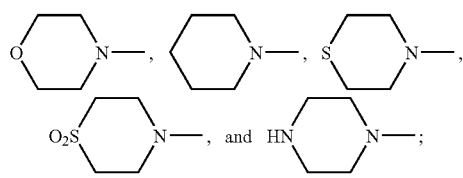

wherein each of said heterocycloalkyl is optionally substituted by one or more $C_{1-7}$-alkyl, $C_{1-7}$-alkoxy, $C_{1-7}$-haloalkyl and $C_{1-7}$-hydroxyalkyl;

Y is a bond, —CH$_2$— or —CH$_2$—CH$_2$—O—;

$R^2$ is cyclooctyl;

phenyl, optionally substituted by one or more $C_{1-7}$-alkoxy and cyclopropyl;

furanyl, optionally substituted by methyl; or a 5- or 6-membered cycloalkyl or heterocycloalkyl, anellated with a benzo ring, selected from the group consisting of

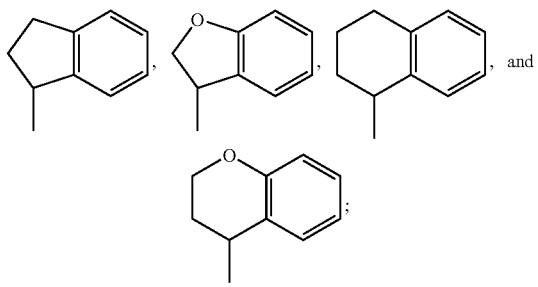

wherein each of said 5- or 6-membered cycloalkyl or heterocycloalkyl anellated with a benzo ring is optionally substituted by one or more halo and $C_{1-7}$-alkoxy;

or a pharmaceutically acceptable salt thereof.

17. The compound of claim 16 selected from the group consisting of:

N-[2-((R)-Indan-1-ylamino)-4H-benzo[d][1,3]oxazin-6-yl]-2-(4-methyl-piperazin-1yl)-acetamide, rac-2-Chloro-N-[2-(4-methoxy-2,3-dihydro-benzofuran-3-ylamino)-4H-benzo[d][1,3]oxazin-6-yl]-acetamide, rac-N-[2-(4-Methoxy-2,3-dihydro-benzofuran-3-ylamino)-4H-benzo[d][1,3]oxazin-6-yl]-2-(4-methyl-piperazin-1-yl)-acetamide, rac-2-(4-Isopropyl-piperazin-1-yl)-N-[2-(4-methoxy-2,3-dihydro-benzofuran-3-ylamino)-4H-benzo[d][1,3]oxazin-6-yl]-acetamide, rac-N-[2-(4-Methoxy-2,3-dihydro-benzofuran-3-ylamino)-4H-benzo[d][1,3]oxazin-6-yl]-2-morpholin-4-yl-acetamide, rac-2-Methoxy-N-[2-(4-methoxy-2,3-dihydro-benzofuran-3-ylamino)-4H-benzo[d][1,3]oxazin-6-yl]-acetamide, N-[2-((R)-Indan-1-ylamino)-4H-benzo[d][1,3]oxazin-6-yl]-2-methoxy-acetamide, rac-N-[2-(5-Fluoro-indan-1-ylamino)-4H-benzo[d][1,3]oxazin-6-yl]-2-methoxy-acetamide, rac-2-Methoxy-N-[2-(7-methoxy-indan-1-ylamino)-4H-benzo[d][1,3]oxazin-6-yl]-acetamide, and N-[2-(2-Methoxy-benzylamino)-4H-benzo[d][1,3]oxazin-6-yl]-2-(4-methyl-piperazin-1-yl) -acetamide.

18. The compound of claim 16 selected from the group consisting of:

2-[4-(2-Hydroxy-ethyl)-piperazin-1-yl]-N-[2-(2-methoxy-benzylamino)-4H-benzo[d][1,3]oxazin-6-yl]-acetamide, 2-(4-Isopropyl-piperazin-1-yl)-N-[2-(2-methoxy-benzylamino)-4H-benzo[d][1,3]oxazin-6-yl]-acetamide, N-[2-((R)-Indan-1-ylamino)-4H-benzo[d][1,3]oxazin-6-yl]-2-morpholin-4-yl-acetamide, 2-(4-Methyl-piperazin-1-yl)-N-{2-[(R)-(1,2,3,4-tetrahydro-naphthalen-1-yl)amino]-4H-benzo[d][1,3]oxazin-6-yl}-acetamide, 2-Morpholin-4-yl-N-{2-[(R)-(1,2,3,4-tetrahydro-naphthalen-1-yl)amino]-4H-benzo[d][1,3]oxazin-6-yl}-acetamide, rac-N-[2-(6-Fluoro-2,3-dihydro-benzofuran-3-ylamino)-4H-benzo[d][1,3]oxazin-6-yl]-2-(4-methyl-piperazin-1-yl)-acetamide, rac-N-[2-(6-Fluoro-2,3-dihydro-benzofuran-3-ylamino)-4H-benzo[d][1,3]oxazin-6-yl]-2-morpholin-4-yl-acetamide, rac-N-[2-(7-Methoxy-indan-1-ylamino)-4H-benzo[d][1,3]oxazin-6-yl]-2-morpholin-4-yl-acetamide, rac-N-[2-(5-Fluoro-indan-1-ylamino)-4H-benzo[d][1,3]
oxazin-6-yl]-2-morpholin-4-yl-acetamide, and
N-[2-((R)-Indan-1-ylamino)-4H-benzo[d][1,3]oxazin-6-
yl]-2-thiomorpholin-4-yl-acetamide.

19. The compound of claim 16 selected from the group consisting of:
2-(1,1-Dioxo-1$\lambda^6$-thiomorpholin-4-yl)-N-[2-((R)-indan-1-ylamino)-4H-benzo[d][1,3]oxazin-6-yl]-acetamide,
2-Imidazol-1-yl-N-[2-((R)-indan-1-ylamino)-4H-benzo[d][1,3]oxazin-6-yl]-acetamide,
N-[2-((R)-Indan-1-ylamino)-4H-benzo[d][1,3]oxazin-6-yl]-2-[4-(2,2,2-trifluoro-ethyl)-piperazin-1-yl]-acetamide,
N-{2-[(5-Methyl-furan-2-ylmethyl)-amino]-4H-benzo[d][1,3]oxazin-6-yl}-2-(4-methyl-piperazin-1-yl)-acetamide,
N-{2-[(5-Methyl-furan-2-ylmethyl)-amino]-4H-benzo[d][1,3]oxazin-6-yl}-2-morpholin-4-yl-acetamide,
rac-N-[2-(7-Methoxy-indan-1-ylamino)-4H-benzo[d][1,3]oxazin-6-yl]-2-(4-methyl-piperazin-1-yl)-acetamide,
N-(2-Cycloheptylamino-4H-benzo[d][1,3]oxazin-6-yl)-2-(4-methyl-piperazin-1-yl)-acetamide,
2-(3-Hydroxymethyl-4-methyl-piperazin-1-yl)-N-[2-(7-methoxy-indan-1-ylamino)-4H-benzo[d][1,3]oxazin-6-yl]-acetamide,
rac-N-[2-(Chroman-4-ylamino)-4H-benzo[d][1,3]oxazin-6-yl]-2-(4-methyl-piperazin-1-yl)-acetamide, and
rac-N-[2-(Chroman-4-ylamino)-4H-benzo[d][1,3]oxazin-6-yl]-2-morpholin-4-yl-acetamide.

20. The compound of claim 16 selected from the group consisting of:
2-(4-Methyl-piperazin-1-yl)-N-[2-(2-phenoxy-ethylamino)-4H-benzo[d][1,3]oxazin-6-yl]-acetamide,
2-Morpholin-4-yl-N-[2-(2-phenoxy-ethylamino)-4H-benzo[d][1,3]oxazin-6-yl]-acetamide,
N-[2-(3-Cyclopropyl-phenylamino)-4H-benzo[d][1,3]oxazin-6-yl]-2-(4-methyl-piperazin-1-yl)-acetamide,
N-[2-(7-Methoxy-indan-1-ylamino)-4H-benzo[d][1,3]oxazin-6-yl]-2-(3-methoxymethyl-4-methyl-piperazin-1-yl)-acetamide,
N-[2-((R)-Indan-1-ylamino)-4H-benzo[d][1,3]oxazin-6-yl]-2-(3-methoxymethyl-4-methyl-piperazin-1-yl)-acetamide,
N-(2-Cyclooctylamino-4H-benzo[d][1,3]oxazin-6-yl)-2-(4-methyl-piperazin-1-yl)-acetamide,
endo-N-[2-((R)-Indan-1-ylamino)-4H-benzo[d][1,3]oxazin-6-yl]-2-(9-methyl-3-oxa-9-aza-bicyclo[3.3.1]non-7-yl)-acetamide,
2-((3SR,5SR)-3,5-Bis-(methoxymethyl)-4-methyl-piperazin-1-yl)-N-[2-((R)-indan-1-ylamino)-4H-benzo[d][1,3]oxazin-6-yl]-acetamide, and
N-[2-((R)-Indan-1-ylamino)-4H-benzo[d][1,3]oxazin-6-yl]-2-(9-methyl-3-oxa-7,9-diaza-bicyclo[3.3.1]non-7-yl)-acetamide.

21. The compound of claim 1, wherein X is a bond, —CH$_2$—, —CH$_2$—NH—C(O)—, —NH—, —NH—C(O)—, —NH—C(O)—CH$_2$—, —NH—C(O)—CH$_2$—NH—, —NH—CH$_2$—, —NH—S(O)$_2$— or —NR$^a$—C(O)—NR$^b$—, wherein R$^a$ and R$^b$ are either H or C$_{1-7}$ alkyl.

22. The compound of claim 21, wherein X is a bond, —NH—, —NH—C(O)—, —NH—C(O)—CH$_2$—, —NH—CH$_2$—, —NH—S(O)$_2$— or —NR$^a$—C(O)—NR$^b$—, wherein R$^a$ and R$^b$ are either H or methyl.

23. The compound of claim 1, wherein R$^1$ is:
halo;
C$_{1-7}$-alkyl, optionally substituted by OH or C$_{1-7}$ alkoxy;
C$_{1-7}$-alkoxy;
—NR$^a$R$^b$, wherein R$^a$ and R$^b$ are either H or C$_{1-7}$ alkyl;
—C(NH$_2$)N(OH);
cyano;
nitro;
cycloalkyl;
heterocycloalkyl, optionally substituted by one or more C$_{1-7}$-alkyl, C$_{1-7}$-haloalkyl, C$_{1-7}$-hydroxyalkyl, C$_{1-7}$-alkoxy-alkyl, or 5- to 9-membered monocyclic or bicyclic heterocycloalkyl;
aryl, optionally substituted by one or more halo;
heteroaryl, optionally substituted by one or more C$_{1-7}$-alkyl, C$_{1-7}$-haloalkyl, or 3- to 7-membered monocyclic cycloalkyl; or
vinyl; optionally substituted by phenyl or a 5- or 6-membered monocyclic heteroaryl.

24. The compound of claim 23, wherein R$^1$ is:
halo;
C$_{1-7}$-alkyl;
—NR$^a$R$^b$, wherein R$^a$ and R$^b$ are either H or C$_{1-7}$ alkyl;
cycloalkyl;
heterocycloalkyl, optionally substituted by one or more C$_{1-7}$-alkyl; or
heteroaryl, optionally substituted by one or more C$_{1-7}$-alkyl, 3- to 7-membered monocyclic cycloalkyl.

25. The compound of claim 24, wherein R$^1$ is isopropyl, NH$_2$, cyclopropyl, piperazinyl substituted by methyl, [1,3,4]oxadiazolyl substituted by methyl or cyclopropyl, pyridinyl or thiazolyl.

26. The compound of claim 1, wherein Y is a bond, CH$_2$— or —CH$_2$—CH$_2$—O—.

27. The compound of claim 26, wherein Y is a bond.

28. The compound of claim 1, wherein R$^2$ is:
cycloalkyl;
aryl, optionally substituted by one or more C$_{1-7}$-alkoxy or 3- to 7-membered monocyclic cycloalkyl;
heteroaryl, optionally substituted by one or more C$_{1-7}$-alkyl; or
5- or 6-membered cycloalkyl or heterocycloalkyl, anellated with a benzo ring, optionally substituted by one or more halo, C$_{1-7}$-alkyl or C$_{1-7}$-alkoxy.

29. The compound of claim 28, wherein R$^2$ is:
cycloalkyl; or
5- or 6-membered cycloalkyl, anellated with a benzo ring, optionally substituted by one or more halo or C$_{1-7}$-alkoxy.

30. The compound of claim 29, wherein R$^2$ is cycloheptyl, cyclooctyl, 1,2,3,4-tetrahydro-naphthalenyl substituted by one methoxy, indanyl optionally substituted by one fluoro or methoxy.

31. The compound of claim 1, wherein R$^2$ is

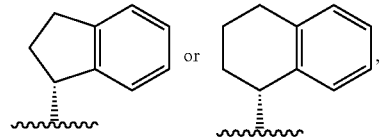

each optionally substituted by one or more halo or C$_{1-7}$-alkoxy, and wherein R$^2$ is present as (R)-stereoisomer.

32. The compound of claim 1 selected from the group consisting of:
(2-Methoxy-benzyl)-(6-nitro-4H-benzo[d][1,3]oxazin-2-yl)-amine,
(R)—N$^2$-Indan-1-yl-4H-benzo[d][1,3]oxazine-2,6-diamine, N-[2-((R)-Indan-1-ylamino)-4H-benzo[d][1,3]oxazin-6-yl]-2-(4-methyl-piperazin-1-yl)-acetamide,
$N^2$-(2-Methoxy-benzyl)-4H-benzo[d][1,3]oxazine-2,6-diamine,
rac-(4-Methoxy-2,3-dihydro-benzofuran-3-yl)-(6-nitro-4H-benzo[d][1,3]oxazin-2-yl)-amine,
rac-$N^2$-(4-Methoxy-2,3-dihydro-benzofuran-3-yl)-4H-benzo[d][1,3]oxazine-2,6-diamine,
Cyclopropanecarboxylic acid [2-(2-methoxy-benzylamino)-4H-benzo[d][1,3]oxazin-6-yl]-amide,
rac-2-Chloro-N-[2-(4-methoxy-2,3-dihydro-benzofuran-3-ylamino)-4H-benzo[d][1,3]oxazin-6-yl]-acetamide,
rac-N-[2-(4-Methoxy-2,3-dihydro-benzofuran-3-ylamino)-4H-benzo[d][1,3]oxazin-6-yl]-2-(4-methyl-piperazin-1-yl)-acetamide, and
rac-$N^2$-(7-Methoxy-indan-1-yl)-4H-benzo[d][1,3]oxazine-2,6-diamine.

33. The compound of claim 1 selected from the group consisting of:
rac-$N^2$-(5-Fluoro-indan-1-yl)-4H-benzo[d][1,3]oxazine-2,6-diamine,
rac-2-(4-Isopropyl-piperazin-1-yl)-N-[2-(4-methoxy-2,3-dihydro-benzofuran-3-ylamino)-4H-benzo[d][1,3]oxazin-6-yl]-acetamide,
rac-N-[2-(4-Methoxy-2,3-dihydro-benzofuran-3-ylamino)-4H-benzo[d][1,3]oxazin-6-yl]-2-morpholin-4-yl-acetamide,
rac-1-(1-Isopropyl-piperidin-4-yl)-3-[2-(4-methoxy-2,3-dihydro-benzofuran-3-ylamino)-4H-benzo[d][1,3]oxazin-6-yl]-urea,
rac-1-(1-Isopropyl-piperidin-4-yl)-3-[2-(4-methoxy-2,3-dihydro-benzofuran-3-ylamino)-4H-benzo[d][1,3]oxazin-6-yl]-1-methyl-urea, rac-1-Isopropyl-3-[2-(4-methoxy-2,3-dihydro-benzofuran-3-ylamino)-4H-benzo[d][1,3]oxazin-6-yl]-urea,
rac-2-Methoxy-N-[2-(4-methoxy-2,3-dihydro-benzofuran-3-ylamino)-4H-benzo[d][1,3]oxazin-6-yl]-acetamide,
Cyclopropanecarboxylic acid [2-((R)-indan-1-ylamino)-4H-benzo[d][1,3]oxazin-6-yl]-amide,
N-[2-((R)-Indan-1-ylamino)-4H-benzo[d][1,3]oxazin-6-yl]-2-methoxy-acetamide, and
rac-Cyclopropanecarboxylic acid [2-(5-fluoro-indan-1-ylamino)-4H-benzo[d][1,3]oxazin-6-yl]-amide.

34. The compound of claim 1 selected from the group consisting of:
rac-N-[2-(5-Fluoro-indan-1-ylamino)-4H-benzo[d][1,3]oxazin-6-yl]-2-methoxy-acetamide,
rac-$N^2$-(8-Methoxy-1,2,3,4-tetrahydro-naphthalen-1-yl)-4H-benzo[d][1,3]oxazine-2,6-diamine,
rac-Cyclopropanecarboxylic acid [2-(8-methoxy-1,2,3,4-tetrahydro-naphthalen-1-ylamino)-4H-benzo[d][1,3]oxazin-6-yl]-amide,
rac-2-Methoxy-N-[2-(7-methoxy-indan-1-ylamino)-4H-benzo[d][1,3]oxazin-6-yl]-acetamide,
Cyclopropanecarboxylic acid [2-(7-methoxy-indan-1-ylamino)-4H-benzo[d][1,3]oxazin-6-yl]-amide,
N-[2-(2-Methoxy-benzylamino)-4H-benzo[d][1,3]oxazin-6-yl]-2-(4-methyl-piperazin-1-yl)-acetamide,
N,N-(Dimethyl)-N'-{2-((R)-indan-1-ylamino)-4H-benzo[d][1,3]oxazin-6-yl}-sulfamide,
2-[4-(2-Hydroxy-ethyl)-piperazin-1-yl]-N-[2-(2-methoxy-benzylamino)-4H-benzo[d][1,3]oxazin-6-yl]-acetamide,
2-(4-Isopropyl-piperazin-1-yl)-N-[2-(2-methoxy-benzylamino)-4H-benzo[d][1,3]oxazin-6-yl]-acetamide, and Piperidine-1-sulfonic acid [2-((R)-indan-1-ylamino)-4H-benzo[d][1,3]oxazin-6-yl]-amide.

35. The compound of claim 1 selected from the group consisting of:
Morpholine-4-sulfonic acid [2-((R)-indan-1-ylamino)-4H-benzo[d][1,3]oxazin-6-yl]-amide,
(6-Bromo-4H-benzo[d][1,3]oxazin-2-yl)-(R)-indan-1-yl-amine,
(R)—$N^2$-(1,2,3,4-Tetrahydro-naphthalen-1-yl)-4H-benzo[d][1,3]oxazine-2,6-diamine,
rac-$N^2$-(6-Fluoro-2,3-dihydro-benzofuran-3-yl)-4H-benzo[d][1,3]oxazine-2,6-diamine,
$N^2$—(R)-Indan-1-yl-$N^6$-(6-trifluoromethyl-pyridin-2-yl)-4H-benzo[d][1,3]oxazine-2,6-diamine,
N-[2-((R)-Indan-1-ylamino)-4H-benzo[d][1,3]oxazin-6-yl]-2-morpholin-4-yl-acetamide,
2-(4-Methyl-piperazin-1-yl)-N-{2-[(R)-(1,2,3,4-tetrahydro-naphthalen-1-yl)amino]-4H-benzo[d][1,3]oxazin-6-yl}-acetamide,
2-Morpholin-4-yl-N-{2-[(R)-(1,2,3,4-tetrahydro-naphthalen-1-yl)amino]-4H-benzo[d][1,3]oxazin-6-yl}-acetamide,
2-(2-Methoxy-ethylamino)-N-{2-[(R)-(1,2,3,4-tetrahydro-naphthalen-1-yl)amino]-4H-benzo[d][1,3]oxazin-6-yl}-acetamide, and
2-(2-Hydroxy-2-methyl-propylamino)-N-{2-[(R)-(1,2,3,4-tetrahydro-naphthalen-1-yl)amino]-4H-benzo[d][1,3]oxazin-6-yl}-acetamide.

36. The compound of claim 1 selected from the group consisting of:
rac-N-[2-(6-Fluoro-2,3-dihydro-benzofuran-3-ylamino)-4H-benzo[d][1,3]oxazin-6-yl]-2-(2-methoxy-ethylamino)-acetamide,
rac-N-[2-(6-Fluoro-2,3-dihydro-benzofuran-3-ylamino)-4H-benzo[d][1,3]oxazin-6-yl]-2-(2-hydroxy-2-methyl-propylamino)-acetamide,
rac-N-[2-(6-Fluoro-2,3-dihydro-benzofuran-3-ylamino)-4H-benzo[d][1,3]oxazin-6-yl]-2-(4-methyl-piperazin-1-yl)-acetamide,
rac-N-[2-(6-Fluoro-2,3-dihydro-benzofuran-3-ylamino)-4H-benzo[d][1,3]oxazin-6-yl]-2-morpholin-4-yl-acetamide,
$N^2$—(R)-Indan-1-yl-$N^6$-(4-trifluoromethyl-pyrimidin-2-yl)-4H-benzo[d][1,3]oxazine-2,6-diamine,
$N^6$-(4,6-Dimethyl-pyrimidin-2-yl)-$N^2$—(R)-indan-1-yl-4H-benzo[d][1,3]oxazine-2,6-diamine,
N-[2-((R)-Indan-1-ylamino)-4H-benzo[d][1,3]oxazin-6-yl]-acetamide,
rac-N,N-(Dimethyl)-N'-{2-(4-methoxy-2,3-dihydro-benzofuran-3-ylamino)-4H-benzo[d][1,3]oxazin-6-yl}-sulfamide,
Piperidine-1-sulfonic acid [2-(4-methoxy-2,3-dihydro-benzofuran-3-ylamino)-4H-benzo[d][1,3]oxazin-6-yl]-amide, and
N-[2-(4-Methoxy-2,3-dihydro-benzofuran-3-ylamino)-4H-benzo[d][1,3]oxazin-6-yl]-acetamide.

37. The compound of claim 1 selected from the group consisting of:
N-[2-(7-Methoxy-indan-1-ylamino)-4H-benzo[d][1,3]oxazin-6-yl]-acetamide,
rac-(6-Bromo-4H-benzo[d][1,3]oxazin-2-yl)-(5-fluoro-indan-1-yl)-amine,
rac-(6-Bromo-4H-benzo[d][1,3]oxazin-2-yl)-(4-methoxy-2,3-dihydro-benzofuran-3-yl)-amine,
rac-N-[2-(7-Methoxy-indan-1-ylamino)-4H-benzo[d][1,3]oxazin-6-yl]-2-morpholin-4-yl-acetamide, rac-N-[2-(5-Fluoro-indan-1-ylamino)-4H-benzo[d][1,3]
oxazin-6-yl]-2-morpholin-4-yl-acetamide,
rac-N$^2$-(5-Fluoro-indan-1-yl)-N$^6$-(6-trifluoromethyl-pyridin-2-yl)-4H-benzo[d][1,3]oxazine-2,6-diamine,
rac-N$^2$-(5-Fluoro-indan-1-yl)-N$^6$-(4-trifluoromethyl-pyrimidin-2-yl)-4H-benzo[d][1,3]oxazine-2,6-diamine,
rac-N$^2$-(4-Methoxy-2,3-dihydro-benzofuran-3-yl)-N$^6$-(6-trifluoromethyl-pyridin-2-yl)-4H-benzo[d][1,3]oxazine-2,6-diamine,
rac-N$^2$-(4-Methoxy-2,3-dihydro-benzofuran-3-yl)-N$^6$-(4-trifluoromethyl-pyrimidin-2-yl)-4H-benzo[d][1,3]oxazine-2,6-diamine, and
rac-N,N-(Dimethyl)-N'-{2-(7-Methoxy-indan-1-ylamino)-4H-benzo[d][1,3]oxazin-6-yl}-sulfamide.

38. The compound of claim 1 selected from the group consisting of:
rac-Piperidine-1-sulfonic acid [2-(7-methoxy-indan-1-ylamino)-4H-benzo[d][1,3]oxazin-6-yl]-amide,
rac-Morpholine-4-sulfonic acid [2-(7-methoxy-indan-1-ylamino)-4H-benzo[d][1,3]oxazin-6-yl]-amide,
rac-N,N-(Dimethyl)-N'-{2-(5-Fluoro-indan-1-ylamino)-4H-benzo[d][1,3]oxazin-6-yl}-sulfamide,
N-[2-((R)-Indan-1-ylamino)-4H-benzo[d][1,3]oxazin-6-yl]-2-thiomorpholin-4-yl-acetamide,
2-(1,1-Dioxo-1λ$^6$-thiomorpholin-4-yl)-N-[2-((R)-indan-1-ylamino)-4H-benzo[d][1,3]oxazin-6-yl]-acetamide,
2-Imidazol-1-yl-N-[2-((R)-indan-1-ylamino)-4H-benzo[d][1,3]oxazin-6-yl]-acetamide,
2-(2-Hydroxy-2-methyl-propylamino)-N-[2-((R)-indan-1-ylamino)-4H-benzo[d][1,3]oxazin-6-yl]-acetamide,
N-[2-((R)-Indan-1-ylamino)-4H-benzo[d][1,3]oxazin-6-yl]-2-(2-methoxy-ethylamino)-acetamide,
N-[2-((R)-Indan-1-ylamino)-4H-benzo[d][1,3]oxazin-6-yl]-2-[4-(2,2,2-trifluoro-ethyl)-piperazin-1-yl]-acetamide, and
4-Methyl-piperazine-1-sulfonic acid {2-[(R)-(1,2,3,4-tetrahydro-naphthalen-1-yl)amino]-4H-benzo[d][1,3]oxazin-6-yl}-amide.

39. The compound of claim 1 selected from the group consisting of:
4-Methyl-piperazine-1-sulfonic acid [2-((R)-indan-1-ylamino)-4H-benzo[d][1,3]oxazin-6-yl]-amide,
2-((exo)-8-Isopropyl-8-aza-bicyclo[3.2.1]oct-3-ylamino)-N-{2-[(R)-(1,2,3,4-tetrahydro-naphthalen-1-yl)amino]-4H-benzo[d][1,3]oxazin-6-yl}-acetamide,
rac-(6-Bromo-4H-benzo[d][1,3]oxazin-2-yl)-(7-methoxy-indan-1-yl)-amine,
rac-N$^2$-Chroman-4-yl-4H-benzo[d][1,3]oxazine-2,6-diamine,
N-[2-((R)-Indan-1-ylamino)-4H-benzo[d][1,3]oxazin-6-yl]-2-((exo)-8-isopropyl-8-aza-bicyclo[3.2.1]oct-3-ylamino)-acetamide,
N$^2$-(5-Methyl-furan-2-ylmethyl)-4H-benzo[d][1,3]oxazine-2,6-diamine,
N-[2-((R)-Indan-1-ylamino)-4H-benzo[d][1,3]oxazin-6-yl]-methanesulfonamide,
Cyclopropanesulfonic acid [2-((R)-indan-1-ylamino)-4H-benzo[d][1,3]oxazin-6-yl]-amide,
rac-N$^2$-(7-Methoxy-indan-1-yl)-N$^6$-(6-trifluoromethyl-pyridin-2-yl)-4H-benzo[d][1,3]oxazine-2,6-diamine, and
rac-N$^2$-(7-Methoxy-indan-1-yl)-N$^6$-(4-trifluoromethyl-pyrimidin-2-yl)-4H-benzo[d][1,3]oxazine-2,6-diamine.

40. The compound of claim 1 selected from the group consisting of:
Cyclopropanecarboxylic acid {2-[(5-methyl-furan-2-ylmethyl)-amino]-4H-benzo[d][1,3]oxazin-6-yl}-amide,
N-[2-((R)-Indan-1-ylamino)-4H-benzo[d][1,3]oxazin-6-yl]-benzenesulfonamide,
N-{2-[(5-Methyl-furan-2-ylmethyl)-amino]-4H-benzo[d][1,3]oxazin-6-yl}-2-(4-methyl-piperazin-1-yl)-acetamide,
N-{2-[(5-Methyl-furan-2-ylmethyl)-amino]-4H-benzo[d][1,3]oxazin-6-yl}-2-morpholin-4-yl-acetamide,
rac-N-[2-(7-Methoxy-indan-1-ylamino)-4H-benzo[d][1,3]oxazin-6-yl]-2-(4-methyl-piperazin-1-yl)-acetamide,
N$^2$-(2-Phenoxy-ethyl)-4H-benzo[d][1,3]oxazine-2,6-diamine,
N$^2$—(R)-Indan-1-yl-N$^6$-pyridin-3-ylmethyl-4H-benzo[d][1,3]oxazine-2,6-diamine,
N$^2$—(R)-Indan-1-yl-N$^6$-thiazol-2-ylmethyl-4H-benzo[d][1,3]oxazine-2,6-diamine,
rac-Cyclopropanecarboxylic acid [2-(chroman-4-ylamino)-4H-benzo[d][1,3]oxazin-6-yl]-amide, and
rac-N,N-(Dimethyl)-N'-{2-(Chroman-4-ylamino)-4H-benzo[d][1,3]oxazin-6-yl}-sulfamide.

41. The compound of claim 1 selected from the group consisting of:
N$^2$-Cycloheptyl-4H-benzo[d][1,3]oxazine-2,6-diamine,
N-(2-Cycloheptylamino-4H-benzo[d][1,3]oxazin-6-yl)-2-(4-methyl-piperazin-1-yl)-acetamide,
N$^6$-Benzyl-N$^2$-cycloheptyl-4H-benzo[d][1,3]oxazine-2,6-diamine,
Cyclopropanecarboxylic acid (2-cycloheptylamino-4H-benzo[d][1,3]oxazin-6-yl)-amide,
Cyclopropanecarboxylic acid [2-(2-phenoxy-ethylamino)-4H-benzo[d][1,3]oxazin-6-yl]-amide,
Cyclopropanesulfonic acid (2-cycloheptylamino-4H-benzo[d][1,3]oxazin-6-yl)-amide,
N$^2$-Cycloheptyl-N$^6$-thiazol-2-ylmethyl-4H-benzo[d][1,3]oxazine-2,6-diamine,
N,N-(Dimethyl)-N'-{2-cycloheptylamino-4H-benzo[d][1,3]oxazin-6-yl-}-sulfamide,
N-(2-Cycloheptylamino-4H-benzo[d][1,3]oxazin-6-yl)-benzenesulfonamide, and
N$^2$-(7-Methoxy-indan-1-yl)-N$^6$-(5-methyl-[1,3,4]oxadiazol-2-yl)-4H-benzo[d][1,3]oxazine-2,6-diamine.

42. The compound of claim 1 selected from the group consisting of:
rac-N-[2-(7-Methoxy-indan-1-ylamino)-4H-benzo[d][1,3]oxazin-6-yl]-methanesulfonamide,
rac-Cyclopropanesulfonic acid [2-(7-methoxy-indan-1-ylamino)-4H-benzo[d][1,3]oxazin-6-yl]-amide,
rac-N-[2-(7-Methoxy-indan-1-ylamino)-4H-benzo[d][1,3]oxazin-6-yl]-benzenesulfonamide,
N$^2$-Cycloheptyl-N$^6$-(1H-imidazol-2-ylmethyl)-4H-benzo[d][1,3]oxazine-2,6-diamine,
rac-N$^2$-(5-Fluoro-indan-1-yl)-N$^6$-(5-methyl-[1,3,4]oxadiazol-2-yl)-4H-benzo[d][1,3]oxazine-2,6-diamine,
rac-N$^2$-(4-Methoxy-2,3-dihydro-benzofuran-3-yl)-N$^6$-(5-methyl-[1,3,4]oxadiazol-2-yl)-4H-benzo[d][1,3]oxazine-2,6-diamine,
Cyclopropanesulfonic acid [2-(2-phenoxy-ethylamino)-4H-benzo[d][1,3]oxazin-6-yl]-amide,
N-[2-(2-Phenoxy-ethylamino)-4H-benzo[d][1,3]oxazin-6-yl]-benzenesulfonamide,
N,N-(Dimethyl)-N'-{2-(2-Phenoxy-ethylamino)-4H-benzo[d][1,3]oxazin-6-yl}-sulfamide, and N6-(5-Cyclopropyl-[1,3,4]oxadiazol-2-yl)-N2-(7-methoxy-indan-1-yl)-4H-benzo[d][1,3]oxazine-2,6-diamine.

43. The compound of claim 1 selected from the group consisting of:
N6-(2-tert-Butyl-2H-tetrazol-5-yl)-N2-(7-methoxy-indan-1-yl)-4H-benzo[d][1,3]oxazine-2,6-diamine,
Cyclopropanesulfonic acid [2-(4-methoxy-2,3-dihydro-benzofuran-3-ylamino)-4H-benzo[d][1,3]oxazin-6-yl]-amide,
N-[2-(4-Methoxy-2,3-dihydro-benzofuran-3-ylamino)-4H-benzo[d][1,3]oxazin-6-yl]-methanesulfonamide,
N-[2-(4-Methoxy-2,3-dihydro-benzofuran-3-ylamino)-4H-benzo[d][1,3]oxazin-6-yl]-benzenesulfonamide,
2-(3-Hydroxymethyl-4-methyl-piperazin-1-yl)-N-[2-(7-methoxy-indan-1-ylamino)-4H-benzo[d][1,3]oxazin-6-yl]-acetamide,
2-((R)-Indan-1-ylamino)-4H-benzo[d][1,3]oxazine-6-carbonitrile,
N2—(R)-Indan-1-yl-N6-(5-methyl-[1,3,4]oxadiazol-2-yl)-4H-benzo[d][1,3]oxazine-2,6-diamine,
N2-(3-Cyclopropyl-phenyl)-4H-benzo[d][1,3]oxazine-2,6-diamine,
rac-N-[2-(Chroman-4-ylamino)-4H-benzo[d][1,3]oxazin-6-yl]-2-(4-methyl-piperazin-1-yl)-acetamide, and
rac-N-[2-(Chroman-4-ylamino)-4H-benzo[d][1,3]oxazin-6-yl]-2-morpholin-4-yl-acetamide.

44. The compound of claim 1 selected from the group consisting of:
2-(4-Methyl-piperazin-1-yl)-N-[2-(2-phenoxy-ethylamino)-4H-benzo[d][1,3]oxazin-6-yl]-acetamide,
2-Morpholin-4-yl-N-[2-(2-phenoxy-ethylamino)-4H-benzo[d][1,3]oxazin-6-yl]-acetamide,
1-(2-Cycloheptylamino-4H-benzo[d][1,3]oxazin-6-yl)-3-(1-isopropyl-piperidin-4-yl)-urea,
N2-(3-Cyclopropyl-phenyl)-N6-(1H-imidazol-2-ylmethyl)-4H-benzo[d][1,3]oxazine-2,6-diamine,
N-[2-(3-Cyclopropyl-phenylamino)-4H-benzo[d][1,3]oxazin-6-yl]-2-(4-methyl-piperazin-1-yl)-acetamide,
N2-(3-Cyclopropyl-phenyl)-N6-thiazol-2-ylmethyl-4H-benzo[d][1,3]oxazine-2,6-diamine,
Cyclopropanecarboxylic acid [2-(3-cyclopropyl-phenylamino)-4H-benzo[d][1,3]oxazin-6-yl]-amide,
(6-Aminomethyl-4H-benzo[d][1,3]oxazin-2-yl)-(R)-indan-1-yl-amine,
N-Hydroxy-2-((R)-indan-1-ylamino)-4H-benzo[d][1,3]oxazine-6-carboxamidine, and
N2-(2,2-Dimethyl-2,3-dihydro-benzofuran-7-yl)-N6-(1H-imidazol-2-ylmethyl)-4H-benzo[d][1,3]oxazine-2,6-diamine.

45. The compound of claim 1 selected from the group consisting of:
4-Fluoro-N-[2-((R)-indan-1-ylamino)-4H-benzo[d][1,3]oxazin-6-ylmethyl]-benzamide,
(R)-Indan-1-yl-[6-(5-methyl-[1,2,4]oxadiazol-3-yl)-4H-benzo[d][1,3]oxazin-2-yl]-amine,
(R)-Indan-1-yl-(6-vinyl-4H-benzo[d][1,3]oxazin-2-yl)-amine,
N'-{2-[(3-cyclopropylphenyl)amino]-4H-benzo[d][1,3]oxazin-6-yl}-N,N-dimethylsulfamide,
N6-Benzyl-N2-(3-cyclopropyl-phenyl)-4H-benzo[d][1,3]oxazine-2,6-diamine,
1-[2-(3-Cyclopropyl-phenylamino)-4H-benzo[d][1,3]oxazin-6-yl]-3-(1-isopropyl-piperidin-4-yl)-urea,
N2—(R)-Indan-1-yl-N6-(5-trifluoromethyl-[1,3,4]oxadiazol-2-yl)-4H-benzo[d][1,3]oxazine-2,6-diamine,
1-[2-(2,2-Dimethyl-2,3-dihydro-benzofuran-7-ylamino)-4H-benzo[d][1,3]oxazin-6-yl]-3-isopropyl-urea,
(R)-Indan-1-yl-[6-((E)-styryl)-4H-benzo[d][1,3]oxazin-2-yl]-amine, and
rac-2-(4-Methoxy-2,3-dihydro-benzofuran-3-ylamino)-4H-benzo[d][1,3]oxazine-6-carbonitrile.

46. The compound of claim 1 selected from the group consisting of:
rac-2-(7-Methoxy-indan-1-ylamino)-4H-benzo[d][1,3]oxazine-6-carbonitrile,
(R)-Indan-1-yl-[6-((E)-2-pyridin-3-yl-vinyl)-4H-benzo[d][1,3]oxazin-2-yl]-amine,
N2-(7-Methoxy-indan-1-yl)-N6-(5-trifluoromethyl-[1,3,4]oxadiazol-2-yl)-4H-benzo[d][1,3]oxazine-2,6-diamine,
N2-(4-Methoxy-2,3-dihydro-benzofuran-3-yl)-N6-(5-trifluoromethyl-[1,3,4]oxadiazol-2-yl)-4H-benzo[d][1,3]oxazine-2,6-diamine,
N-[2-(7-Methoxy-indan-1-ylamino)-4H-benzo[d][1,3]oxazin-6-yl]-2-(3-methoxymethyl-4-methyl-piperazin-1-yl)-acetamide,
N-[2-((R)-Indan-1-ylamino)-4H-benzo[d][1,3]oxazin-6-yl]-2-(3-methoxymethyl-4-methyl-piperazin-1-yl)-acetamide,
N2-(5-Fluoro-indan-1-yl)-N6-(5-trifluoromethyl-[1,3,4]oxadiazol-2-yl)-4H-benzo[d][1,3]oxazine-2,6-diamine,
Cyclopropanesulfonic acid [2-(3-cyclopropyl-phenylamino)-4H-benzo[d][1,3]oxazin-6-yl]-amide,
N-[2-(3-Cyclopropyl-phenylamino)-4H-benzo[d][1,3]oxazin-6-yl]-benzenesulfonamide, and
1-[2-(3-Cyclopropyl-phenylamino)-4H-benzo[d][1,3]oxazin-6-yl]-3-isopropyl-urea.

47. The compound of claim 1 selected from the group consisting of:
(6-Cyclopropyl-4H-benzo[d][1,3]oxazin-2-yl)-(R)-indan-1-yl-amine,
N2-Cyclooctyl-4H-benzo[d][1,3]oxazine-2,6-diamine,
1-(2-Cycloheptylamino-4H-benzo[d][1,3]oxazin-6-yl)-3-isopropyl-urea,
Cyclopropanecarboxylic acid (2-cyclooctylamino-4H-benzo[d][1,3]oxazin-6-yl)-amide,
N-(2-Cyclooctylamino-4H-benzo[d][1,3]oxazin-6-yl)-2-(4-methyl-piperazin-1-yl)-acetamide,
endo-N-[2-((R)-Indan-1-ylamino)-4H-benzo[d][1,3]oxazin-6-yl]-2-(9-methyl-3-oxa-9-aza-bicyclo[3.3.1]non-7-yl)-acetamide,
2-((3SR,5SR)-3,5-Bis-(methoxymethyl)-4-methyl-piperazin-1-yl)-N-[2-((R)-indan-1-ylamino)-4H-benzo[d][1,3]oxazin-6-yl]-acetamide, and
N-[2-((R)-Indan-1-ylamino)-4H-benzo[d][1,3]oxazin-6-yl]-2-(9-methyl-3-oxa-7,9-diaza-bicyclo[3.3.1]non-7-yl)-acetamide.

48. The compound of claim 1, selected from the group consisting of:
Cyclopropanecarboxylic acid [2-((R)-indan-1-ylamino)-4H-benzo[d][1,3]oxazin-6-yl]-amide,
(R)—N2-Indan-1-yl-4-H-benzo[d][1,3]oxazine-2,6-diamine,
Cyclopropanecarboxylic acid [2-(7-methoxy-indan-1-ylamino)-4H-benzo[d][1,3]oxazin-6-yl]-amide,
N2—(R)-Indan-1-yl-N6-thiazol-2-ylmethyl-4H-benzo[d][1,3]oxazine-2,6-diamine,
N2-(7-Methoxy-indan-1-yl)-4H-benzo[d][1,3]oxazine-2,6-diamine,
N2-(5-Fluoro-indan-1-yl)-4H-benzo[d][1,3]oxazine-2,6-diamine, Cyclopropanecarboxylic acid (2-cyclooctylamino-4H-benzo[d][1,3]oxazin-6-yl)-amide,
Cyclopropanecarboxylic acid [2-(5-fluoro-indan-1-ylamino)-4H-benzo[d][1,3]oxazin-6-yl]-amide,
N2—(R)-Indan-1-yl-N6-(5-methyl-[1,3,4]oxadiazol-2-yl)-4H-benzo[d][1,3]oxazine-2,6diamine,
N-[2-(7-Methoxy-indan-1-ylamino)-4H-benzo[d][1,3]oxazin-6-yl]-2-(4-methyl-piperazin-1-yl)-acetamide,
$N^6$-(5-Cyclopropyl-[1,3,4]oxadiazol-2-yl)-$N^2$-(7-methoxy-indan-1-yl)-4H-benzo[d][1,3]oxazine-2,6-diamine,
$N^2$—(R)-Indan-1-yl-$N^6$-pyridin-3-ylmethyl-4H-benzo[d][1,3]oxazine-2,6-diamine,
Cyclopropanesulfonic acid [2-((R)-indan-1-ylamino)-4H-benzo[d][1,3]oxazin-6-yl]-amide,
N-[2-((R)-Indan-1-ylamino)-4H-benzo[d][1,3]oxazin-6-yl]-2-(4-methyl-piperazin-1-yl)-acetamide,
Cyclopropanecarboxylic acid [2-(8-methoxy-1,2,3,4-tetrahydro-naphthalen-1-ylamino)-4H-benzo[d][1,3]oxazin-6-yl]-amide, and
1-(2-Cycloheptylamino-4H-benzo[d][1,3]oxazin-6-yl)-3-isopropyl-urea,
or a pharmaceutically acceptable salt or ester thereof.

49. A pharmaceutical composition comprising a therapeutically effective amount of a compound of formula I

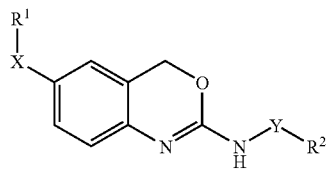
(I)

wherein
X is a bond, —NH—, —NH—S(O)$_2$—, —NH—CH$_2$—, —CH$_2$—, —NH—C(O)—, —CH$_2$—NH—C(O)—, —NH—C(O)—CH$_2$—, —NH—C(O)—CH$_2$—NH—, —NR$^a$—C(O)—NR$^b$—, or —NH—S(O)$_2$—NH—;
R$^1$ is halo;
C$_{1-7}$-alkyl, optionally substituted by OH, C$_{1-7}$ alkoxy or CN;
C$_{1-7}$-alkoxy;
—NR$^a$R$^b$;
—C(NH$_2$)N(OH);
cyano;
nitro;
cycloalkyl;
heterocycloalkyl;
aryl;
heteroaryl; or
vinyl;
wherein each of said cycloalkyl, heterocycloalkyl, aryl and heteroaryl is optionally substituted by one or more halo, cyano, nitro, C$_{1-7}$-alkyl, C$_{1-7}$-haloalkyl, C$_{1-7}$-hydroxyalkyl, C$_{1-7}$-cyanoalkyl, C$_{1-7}$-alkoxy, C$_{1-7}$-alkoxy-alkyl, —NR$^a$R$^b$, or 3- to 7-membered monocyclic cycloalkyl; and
wherein said vinyl is optionally substituted by phenyl or a 5- or 6-membered monocyclic heteroaryl;
Y is a bond, —CH$_2$— or —CH$_2$—CH$_2$—O—;
R$^2$ is cycloalkyl;
heterocycloalkyl;
aryl;
heteroaryl; or
5- or 6-membered cycloalkyl or heterocycloalkyl, anellated with a benzo ring;
wherein each of said cycloalkyl, heterocycloalkyl, aryl, heteroaryl, 5- or 6-membered cycloalkyl or heterocycloalkyl anellated with a benzo ring is optionally substituted by one or more halo, hydroxyl, C$_{1-7}$-alkyl, C$_{1-7}$-alkoxy, or 3- to 7-membered monocyclic cycloalkyl; and
R$^a$ and R$^b$ are each independently hydrogen or C$_{1-7}$-alkyl;
or a pharmaceutically acceptable salt or ester thereof and a pharmaceutically acceptable carrier.

* * * * *